United States Patent
Yagi et al.

(10) Patent No.: US 10,326,083 B2
(45) Date of Patent: Jun. 18, 2019

(54) COMPOUND AND ORGANIC PHOTOELECTRIC DEVICE, IMAGE SENSOR AND ELECTRONIC DEVICE INCLUDING THE SAME

(71) Applicant: Samsung Electronics Co., Ltd., Suwon-si, Gyeonggi-do (KR)

(72) Inventors: Tadao Yagi, Hwaseong-si (KR); Xavier Bulliard, Seongnam-si (KR); Hyesung Choi, Seoul (KR); Rie Sakurai, Suwon-si (KR); Hiromasa Shibuya, Seongnam-si (KR); Youn Hee Lim, Hwaseong-si (KR); Sung Young Yun, Suwon-si (KR); Gae Hwang Lee, Seongnam-si (KR); Kwang Hee Lee, Hwaseong-si (KR); Dong-Seok Leem, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/591,259

(22) Filed: May 10, 2017

(65) Prior Publication Data

US 2017/0331050 A1  Nov. 16, 2017

(30) Foreign Application Priority Data

May 10, 2016 (KR) ........................ 10-2016-0057212

(51) Int. Cl.
| | | |
|---|---|---|
| H01L 51/00 | (2006.01) | |
| H01L 51/44 | (2006.01) | |
| H01L 51/42 | (2006.01) | |
| C07D 421/04 | (2006.01) | |
| C07D 513/04 | (2006.01) | |
| C07D 471/04 | (2006.01) | |
| C07D 421/14 | (2006.01) | |
| C07D 421/06 | (2006.01) | |
| H01L 27/30 | (2006.01) | |
| C07D 421/00 | (2006.01) | |

(52) U.S. Cl.
CPC ........ *H01L 51/0072* (2013.01); *C07D 421/00* (2013.01); *C07D 421/04* (2013.01); *C07D 421/06* (2013.01); *C07D 421/14* (2013.01); *C07D 471/04* (2013.01); *C07D 513/04* (2013.01); *H01L 27/307* (2013.01); *H01L 51/0053* (2013.01); *H01L 51/0061* (2013.01); *H01L 51/0062* (2013.01); *H01L 51/0067* (2013.01); *H01L 51/0071* (2013.01); *H01L 51/424* (2013.01); *H01L 51/441* (2013.01); *H01L 51/447* (2013.01)

(58) Field of Classification Search
CPC .......... H01L 51/0072; H01L 51/447; H01L 51/441; H01L 51/424; H01L 51/0071; H01L 51/0067; H01L 51/0062; H01L 51/0053; H01L 51/0061; H01L 27/307; C07D 421/04; C07D 513/04; C07D 421/14; C07D 421/06
See application file for complete search history.

(56) References Cited

U.S. PATENT DOCUMENTS

| | | | |
|---|---|---|---|
| 6,300,612 B1 | 10/2001 | Yu | |
| 7,129,466 B2 | 10/2006 | Iwasaki | |
| 7,973,307 B2 | 7/2011 | Rand et al. | |
| 8,035,708 B2 | 10/2011 | Takizawa et al. | |
| 8,426,727 B2 | 4/2013 | Pfeiffer et al. | |
| 8,525,577 B2 | 9/2013 | Yofu et al. | |
| 9,070,887 B2 | 6/2015 | Yofu et al. | |
| 2004/0192942 A1 | 9/2004 | Huang | |
| 2007/0012955 A1 | 1/2007 | Ihama | |
| 2011/0074491 A1 | 3/2011 | Yofu et al. | |
| 2012/0313088 A1 | 12/2012 | Yofu et al. | |

(Continued)

FOREIGN PATENT DOCUMENTS

| | | |
|---|---|---|
| CN | 102675898 A | 9/2012 |
| DE | 87576 A | 2/1972 |

(Continued)

OTHER PUBLICATIONS

Jeux, et al. "Miniaturization of molecular conjugated systems for organic solar cells: towards pigmy donors," RCS Adv. vol. 3, pp. 5811-5814 (2013).

(Continued)

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

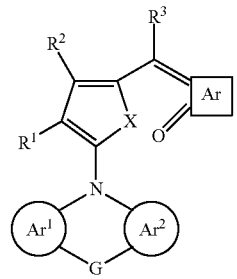

In Chemical Formula 1, each substituent is the same as defined in the detailed description.

23 Claims, 10 Drawing Sheets

(56) References Cited

U.S. PATENT DOCUMENTS

| | | | |
|---|---|---|---|
| 2013/0299799 | A1 | 11/2013 | Yofu et al. |
| 2016/0100153 | A1 | 4/2016 | Jeon et al. |
| 2016/0126470 | A1 | 5/2016 | Ro et al. |
| 2016/0149132 | A1 | 5/2016 | Lim et al. |
| 2017/0148994 | A1 | 5/2017 | Choi et al. |
| 2017/0331050 | A1* | 11/2017 | Yagi .................... C07D 421/04 |

FOREIGN PATENT DOCUMENTS

| | | |
|---|---|---|
| EP | 0193885 A1 | 9/1986 |
| EP | 0637774 A1 | 2/1995 |
| JP | 06-143839 A | 5/1994 |
| JP | 2005-123033 A | 5/2005 |
| JP | 5520560 B2 | 6/2014 |
| KR | 2012-0122847 A | 11/2012 |
| KR | 2016-0041379 A | 4/2016 |
| KR | 2016-0052448 A | 5/2016 |
| KR | 2016-0062708 A | 6/2016 |
| KR | 2017-0060488 A | 6/2017 |
| WO | WO-2014/056886 A1 | 4/2014 |

OTHER PUBLICATIONS

Ihama, et al. "CMOS Image Sensor with a Thin Overlaid Panchromatic Organic Photoconductive Layer for Sensors with Reduced Pixel Size," IDW '09, INP1-4, pp. 2123-2126.

Aihara, et al. "Stacked Image Sensor with Green- and Red-Sensitive Organic Photoconductive Films Applying Zinc Oxide Thin-Film Transistors to a Signal Readout Circuit," IEEE Transactions on Electron Devices, vol. 56, No. 11, pp. 2570-2576 (2009).

Seo, et al. "Color Sensors with Three Vertically Stacked Organic Photodetectors," Japanese Journal of Applied Physics, vol. 46, No. 49, pp. L1240-L1242 (2007).

Chun, et al. "The effects of the molecular structure if the chromophore on the photorefractive properties of the polymer systems with low glass transition temperatures," J. Mater. Chem., vol. 12, pp. 858-862 (2002).

CAPLUS Abstract (XP-002771879) for Guo, et al. "Acceptors/linkers effects on dye sensitized solar cell: Theoretical investigations of structure-property relationship for design of efficient dye sensitizers," Journal of Theoretical and Computational Chemistry, vol. 13, No. 7, pp. 1-3 (2014).

Kim, et al. "Synthesis and Photovoltaic Performance of Long Wavelength Absorbing Organic Dyes for Dye-Sensitized Solar Cells," Molecular Crystals and Liquid Crystals, vol. 551, No. 1, pp. 283-294 (2011).

CAPLUS Abstract (XP-002771880) for Hamada, et al. "Dye-sensitized photoelectric converter, photoelectrochemical cell, and dye solution for photoelectric converter," Jpn. Kokail Tokkyo Koho, pp. 1-2 (2012).

Yang, et al. "Synthesis and Photovoltaic Properties of Organic Photosensitizers Based on Phenothiazine Chromophore for Application of Dye-Sensitized Solar Cells," Molecular Crystals and Liquid Crystals, vol. 538, No. 1, pp. 149-156 (2011).

Extended European Search Report dated Jul. 19, 2017 issued in corresponding European Application No. 17170200.4.

* cited by examiner

COMPOUND AND ORGANIC PHOTOELECTRIC DEVICE, IMAGE SENSOR AND ELECTRONIC DEVICE INCLUDING THE SAME

CROSS-REFERENCE TO RELATED APPLICATION

This application claims priority to Korean Patent Application No. 10-2016-0057212, filed in the Korean Intellectual Property Office on May 10, 2016, and all the benefits accruing therefrom under 35 U.S.C. § 119, the entire contents of which are incorporated herein by reference.

BACKGROUND

1. Field

Example embodiments relate to a compound and an organic photoelectric device, an image sensor, and an electronic device including the same.

2. Description of Related Art

A photoelectric device may convert light into an electrical signal using photoelectric effects. A photoelectric device may include a photodiode, a phototransistor, etc. A photoelectric device may be applied to an image sensor, a solar cell, an organic light emitting diode, etc.

An image sensor including a photodiode requires relatively high resolution and thus a smaller pixel. At present, a silicon photodiode is widely used. In some cases, a silicon photodiode may have deteriorated sensitivity because of a relatively small absorption area due to relatively small pixels. Accordingly, an organic material that is capable of replacing silicon has been researched.

An organic material may have a relatively high extinction coefficient and may selectively absorb light in a particular wavelength region depending on a molecular structure, and thus may simultaneously replace a photodiode and a color filter and resultantly improve sensitivity and contribute to relatively high integration.

SUMMARY

Some example embodiments provide a compound that selectively absorbs light in a green wavelength region.

Some example embodiments also provide an organic photoelectric device capable of selectively absorbing light in a green wavelength region and improving efficiency.

Some example embodiments also provide an image sensor including the organic photoelectric device.

Some example embodiments also provide an electronic device including the image sensor.

According to some example embodiments, a compound includes a structure represented by Chemical Formula 1.

[Chemical Formula 1]

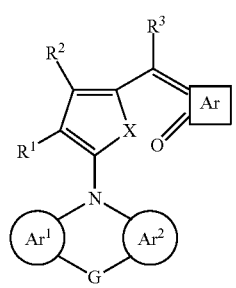

In Chemical Formula 1,

Ar may be one of a substituted or unsubstituted 5-membered aromatic ring, a substituted or unsubstituted 6-membered aromatic ring, and a combination thereof in a condensed ring, X may be one of Se, Te, O, S(=O), S(=O)$_2$, NR$^a$, and SiR$^b$R$^c$ (wherein each of R$^a$, R$^b$, and R$^c$ may be independently one of hydrogen and a substituted or unsubstituted C1 to C10 alkyl group), each of R$^1$ to R$^3$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, each of Ar$^1$ and Ar$^2$ may be independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, and G may be one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ may be independently one of hydrogen, a halogen, a substituted or unsubstituted C1 to C10 alkyl group, and a substituted or unsubstituted C6 to C10 aryl group, and R$^m$ and R$^n$ may be linked to each other to provide a fused ring or R$^m$ and R$^n$ may not be linked together to provide a fused ring, and n may be an integer of 1, or 2).

In some example embodiments, in Chemical Formula 1, at least one of Ar$^1$ and Ar$^2$ may include a heteroatom at 1 position, and the heteroatom may be one of nitrogen (N), sulfur (S), and selenium (Se).

In some example embodiments, structure may be represented by one of Chemical Formula 2-1 to Chemical Formula 2-5.

[Chemical Formula 2-1]

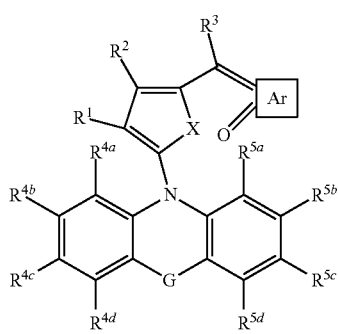

[Chemical Formula 2-2]

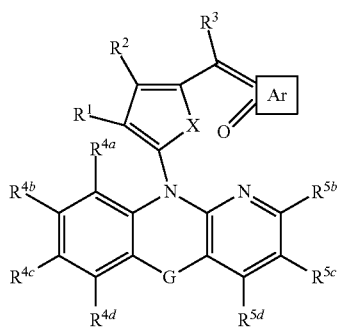

-continued

[Chemical Formula 2-3]

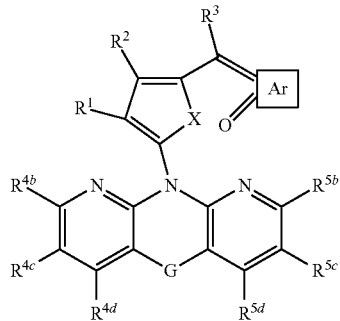

[Chemical Formula 2-4]

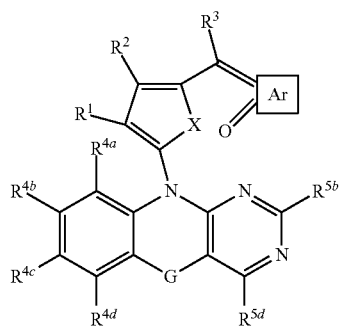

[Chemical Formula 2-5]

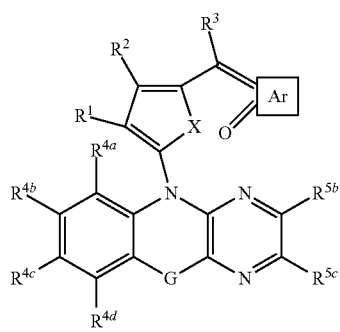

In Chemical Formula 2-1 to Chemical Formula 2-5,

Ar, X, $R^1$ to $R^3$, and G may be the same as in Chemical Formula 1, and $R^{4a}$ to $R^{4d}$ and $R^{5a}$ to $R^{5d}$ may be independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof. Two adjacent groups of $R^{4a}$ to $R^{4d}$ may be linked with each other to provide a 5-membered aromatic ring or a 6-membered aromatic ring, or two adjacent groups of $R^{4a}$ to $R^{4d}$ may not be linked with each other to provide a 5-membered aromatic ring or a 6-membered aromatic ring. Two adjacent groups of $R^{5a}$ to $R^{5d}$ may be linked with each other to provide a 5-membered aromatic ring or a 6-membered aromatic ring, or two adjacent groups of $R^{5a}$ to $R^{5d}$ may not be linked with each other to provide a 5-membered aromatic ring or a 6-membered aromatic ring.

In some example embodiments, in Chemical Formula 1 and Chemical Formulae 2-1 to 2-5, a ring group represented by Ar and bound to a methine group may be represented by Chemical Formula 3.

[Chemical Formula 3]

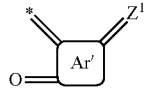

In Chemical Formula 3,

Ar' may be one of a substituted or unsubstituted 5-membered aromatic ring, a substituted or unsubstituted 6-membered aromatic ring, and combination thereof in a condensed ring, and $Z^1$ may be one of O or $CR^bR^c$, wherein each of $R^b$ and $R^c$ may be independently one of hydrogen, a substituted or unsubstituted C1 to C10 alkyl group, a cyano group, or a cyano-containing group, provided that at least one of $R^b$ and $R^c$ may be a cyano group or a cyano-containing group.

In some example embodiments, in Chemical Formula 1 and Chemical Formulae 2-1 to 2-5, a ring group represented by Ar and bound to a methine group may be represented by one of Chemical Formulae 4-1 to 4-4.

[Chemical Formula 4-1]

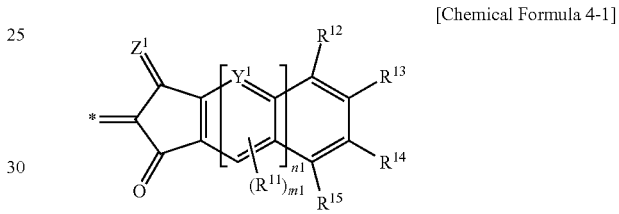

In Chemical Formula 4-1, $Z^1$ may be O or $CR^bR^c$, wherein each of $R^b$ and $R^c$ may be independently one of hydrogen, a substituted or unsubstituted C1 to C10 alkyl group, a cyano group, or a cyano-containing group, provided that at least one of $R^b$ and $R^c$ may be a cyano group or a cyano-containing group, $Y^1$ may be one of N and $CR^d$, wherein $R^d$ may be one of hydrogen and a substituted or unsubstituted C1 to C10 alkyl group, each of $R^{11}$, $R^{12}$, $R^{13}$, $R^{14}$, and $R^{15}$ may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, or $R^{12}$ and $R^{13}$ may be (or may not be) independently linked with each other to provide an aromatic ring or $R^{14}$ and $R^{15}$ may be (or may not be) independently linked with each other to provide an aromatic ring, m1 may be 0 or 1, n1 may be 0 or 1, and

* indicates a linking position with a methine group.

[Chemical Formula 4-2]

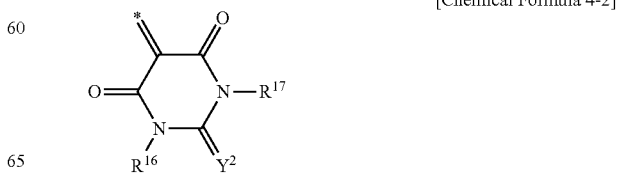

In Chemical Formula 4-2, $Y^2$ may be one of O, S, Se, Te, and $C(R^e)(CN)$ (wherein $R^e$ may be one of hydrogen, a cyano group (—CN), and a C1 to C10 alkyl group), $R^{16}$ and $R^{17}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), and a combination thereof, and

* indicates a linking position with a methine group.

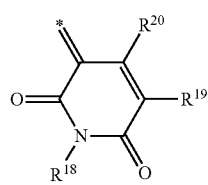

[Chemical Formula 4-3]

In Chemical Formula 4-3, $R^{18}$ to $R^{20}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and

* indicates a linking position with a methine group.

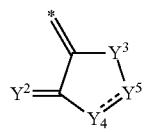

[Chemical Formula 4-4]

In Chemical Formula 4-4, $Y^2$ may be one of O, S, Se, Te, and $C(R^e)(CN)$ (wherein $R^e$ may be one of hydrogen, a cyano group (—CN), and a C1 to C10 alkyl group), $Y^3$ may be one of O, S, Se, and Te, $Y^4$ may be N or $NR^f$, $Y^5$ may be one of $CR^g$, C=O, C=S, $C=(CR^h)(CN)$, and a group represented by Chemical Formula 4-4', when $Y^2$ is not O, $Y^5$ is C=O and when $Y^5$ is not C=O, $Y^2$ is O, $R^f$, $R^g$, and $R^h$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, if $Y^5$ is $CR^g$ or $C=(CR^h)(CN)$, $Y^4$ and $Y^5$ may be linked with each other to provide a $Y^4$-$Y^5$-containing fused ring with the ring structure of Chemical Formula 4-4 and bound to the methine group, or $Y^4$ and $Y^5$ may not be part of a $Y^4$-$Y^5$-containing fused ring with the ring structure of Chemical Formula 4-4 and bound to the methine group, and

* indicates a linking position with a methine group.

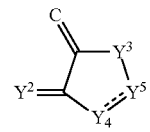

[Chemical Formula 4-4']

In Chemical Formula 4-4', $Y^2$, $Y^3$, $Y^4$, and $Y^5$ are the same as in Chemical Formula 4-4.

In some example embodiments, the structure may be represented by one of Chemical Formulae 5-1 to 5-4.

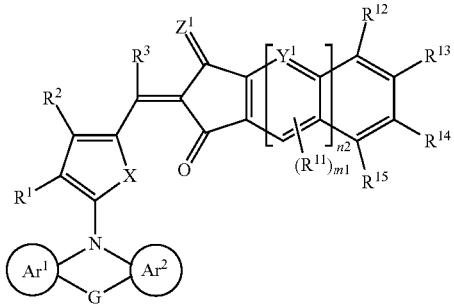

[Chemical Formula 5-1]

In Chemical Formula 5-1,

X may be one of Se, Te, O, S(=O), $S(=O)_2$, $NR^a$, and $SiR^bR^c$ (wherein each of $R^a$, $R^b$, and $R^c$ may be independently one of hydrogen and a substituted or unsubstituted C1 to C10 alkyl group), each of $R^1$ to $R^3$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, each of $Ar^1$ and $Ar^2$ may be independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, G may be one of a direct bond, —$(CR^dR^e)_n$—, —O—, —S—, —Se—, —N=, —$NR^f$—, —$SiR^gR^h$—, —$GeR^iR^j$—, and —$(C(R^m)=C(R^n))$— (wherein each of $R^d$, $R^e$, $R^f$, $R^g$, $R^h$, $R^i$, $R^j$, $R^m$, and $R^n$ may be independently one of hydrogen, a halogen, a substituted or unsubstituted C1 to C10 alkyl group, and a substituted or unsubstituted C6 to C10 aryl group, and optionally $R^m$ and $R^n$ may be linked to each other to provide a fused ring, and n may be an integer of 1, or 2), $Z^1$ may be O or $CR^bR^c$ wherein each of $R^b$ and $R^c$ may be independently one of hydrogen, a substituted or unsubstituted C1 to C10 alkyl group, a cyano group, or a cyano-containing group, provided that at least one of $R^b$ and $R^c$ may be a cyano group or a cyano-containing group, $Y^1$ may be one of N and $CR^d$, wherein $R^d$ may be one of hydrogen and a substituted or unsubstituted C1 to C10 alkyl group, each of $R^{11}$, $R^{12}$, $R^{13}$, $R^{14}$, and $R^{15}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof or $R^{12}$ and $R^{13}$ (or $R^{14}$ and $R^{15}$) may be independently linked with each other to provide an aromatic ring, m1 may be 0 or 1, and n2 may be 0 or 1.

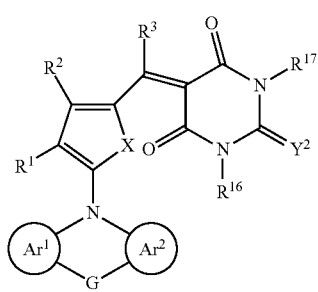

[Chemical Formula 5-2]

In Chemical Formula 5-2,

X may be one of Se, Te, O, S(=O), S(=O)$_2$, NR$^a$, and SiR$^b$R$^c$ (wherein each of R$^a$, R$^b$, and R$^c$ may be independently one of hydrogen and a substituted or unsubstituted C1 to C10 alkyl group), each of Ar$^1$ and Ar$^2$ may be independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, G may be one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ may be independently one of hydrogen, a halogen, a substituted or unsubstituted C1 to C10 alkyl group, and a substituted or unsubstituted C6 to C10 aryl group, and optionally R$^m$ and R$^n$ may be linked to each other to provide a fused ring, and n may be an integer of 1, or 2), Y$^2$ may be one of O, S, Se, Te, and C(R$^e$)(CN) (wherein R$^e$ may be one of hydrogen, a cyano group (—CN), and a C1 to C10 alkyl group), and each of R$^1$, R$^2$, R$^3$, R$^{16}$, and R$^{17}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof.

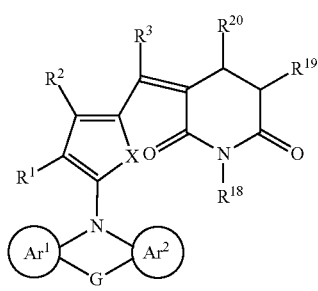

[Chemical Formula 5-3]

In Chemical Formula 5-3,

X may be one of Se, Te, O, S(=O), S(=O)$_2$, NR$^a$, and SiR$^b$R$^c$ (wherein each of R$^a$, R$^b$, and R$^c$ may be independently one of hydrogen and a substituted or unsubstituted C1 to C10 alkyl group), each of R$^1$, R$^2$, R$^3$, R$^{18}$, R$^{19}$, and R$^{20}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, each of Ar$^1$ and Ar$^2$ may be independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, and G may be one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ may be independently one of hydrogen, a halogen, a substituted or unsubstituted C1 to C10 alkyl group, and a substituted or unsubstituted C6 to C10 aryl group, and optionally R$^m$ and R$^n$ may be linked to each other to provide a fused ring, and n may be an integer of 1, or 2).

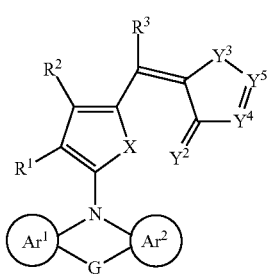

[Chemical Formula 5-4]

In Chemical Formula 5-4,

X may be one of Se, Te, O, S(=O), S(=O)$_2$, NR$^a$, and SiR$^b$R$^c$ (wherein each of R$^a$, R$^b$, and R$^c$ may be independently one of hydrogen and a substituted or unsubstituted C1 to C10 alkyl group), Y$^2$ may be one of O, S, Se, Te, and C(R$^e$)(CN) (wherein R$^e$ may be one of hydrogen, a cyano group (—CN), and a C1 to C10 alkyl group), Y$^3$ may be one of O, S, Se, and Te, Y$^4$ may be N or NR$^f$, Y$^5$ may be one of CR$^g$, C=O, C=S, C=(CR$^h$)(CN), and a group represented by Chemical Formula 4-4', when Y$^2$ is not O, Y$^5$ is C=O and when Y$^5$ is not C=O, Y$^2$ is O, each of R$^1$, R$^2$, R$^3$, R$^f$, R$^g$, and R$^h$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and if Y$^5$ is CR$^g$ or C=(CR$^h$)(CN), Y$^4$ and Y$^5$ may be linked with each other to provide a Y$^4$-Y$^5$-containing fused ring with of the ring structure of Chemical Formula 5-4, or Y$^4$ and Y$^5$ may not be linked with each other.

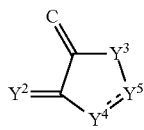

[Chemical Formula 4-4']

In Chemical Formula 4-4',
Y², Y³, Y⁴, and Y⁵ are the same as in Chemical Formula 4-4.

In some example embodiments, the compound may have a maximum absorption wavelength ($\lambda_{max}$) in a wavelength region of greater than or equal to about 510 nm and less than about 560 nm, for example about 520 nm to about 555 nm in a thin film state.

In some example embodiments, the compound may exhibit a light absorption curve having a full width at half maximum (FWHM) of about 50 nm to about 120 nm, in a thin film state.

In some example embodiments, a difference between a melting point of the compound and a temperature (deposition temperature) at which 10 wt % of an initial weight of the compound may be lost may be greater than or equal to about 3° C.

According to some example embodiments, an organic photoelectric device may include a first electrode and a second electrode facing each other and an active layer between the first electrode and the second electrode, and the active layer may include the compound represented by Chemical Formula 1.

In some example embodiments, the active layer the structure of the compound may be represented by one of Chemical Formula 2-1 to Chemical Formula 2-5.

In some example embodiments, the ring group represented by Ar and bound to a methine group may be represented by Chemical Formula 3.

In some example embodiments, the active layer may have a maximum absorption wavelength ($\lambda_{max}$) in a wavelength region of greater than or equal to about 510 nm and less than about 560 nm, for example about 520 nm to about 555 nm.

In some example embodiments, the active layer may exhibit a light absorption curve having a full width at half maximum (FWHM) of about 50 nm to about 120 nm, in a thin film state.

According to some example embodiments, an image sensor may include the organic photoelectric device.

In some example embodiments, the image sensor may include a semiconductor substrate integrated with a plurality of first photo-sensing devices sensing light in a blue wavelength region and a plurality of second photo-sensing devices sensing light in a red wavelength region, and the organic photoelectric device on the semiconductor substrate for selectively sensing light in a green wavelength region.

In some example embodiments, the first photo-sensing device and the second photo-sensing device may be stacked in a vertical direction in the semiconductor substrate.

In some example embodiments, the image sensor may further include a color filter layer between the semiconductor substrate and the organic photoelectric device, and the color filter may include a blue filter for selectively absorbing light in a blue wavelength region and a red filter for selectively absorbing light in a red wavelength region.

In some example embodiments, the image sensor may include a green photoelectric device, a blue photoelectric device for selectively absorbing light in a blue wavelength region, and a red photoelectric device for selectively absorbing light in a red wavelength region that may be stacked. The organic photoelectric device may be the green photoelectric device.

According to some example embodiments, an electronic device includes the image sensor.

According to some example embodiments, a compound includes a structure represented by Chemical Formula 1.

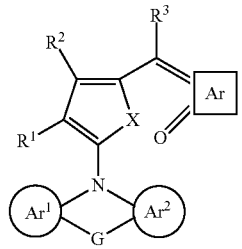

[Chemical Formula 1]

In Chemical Formula 1,
Ar may be one of a substituted or unsubstituted 5-membered aromatic ring, a substituted or unsubstituted 6-membered aromatic ring, and a combination thereof in a condensed ring, X may be one of Se, Te, O, S(=O), S(=O)₂, NR$^a$, and SiR$^b$R$^c$ (wherein each of R$^a$, R$^b$, and R$^c$ may be independently one of hydrogen and a substituted or unsubstituted C1 to C10 alkyl group), each of R¹ to R³ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, each of Ar¹ and Ar² may be independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, and G may be one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ may be independently one of hydrogen, a halogen, a substituted or unsubstituted C1 to C10 alkyl group, and a substituted or unsubstituted C6 to C10 aryl group, and n may be an integer of 1 or 2).

In some example embodiments, structure may be represented by one of Chemical Formula 2-1 to Chemical Formula 2-5.

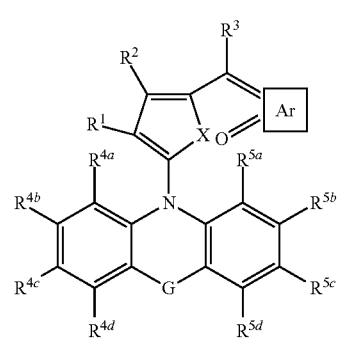

[Chemical Formula 2-1]

-continued

[Chemical Formula 2-2]

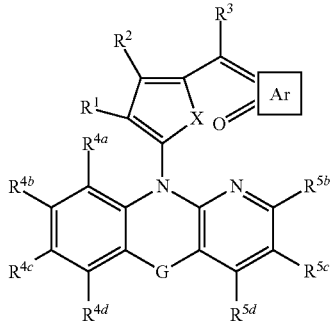

[Chemical Formula 2-3]

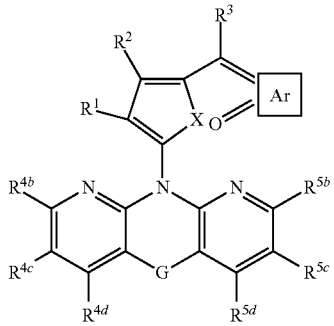

[Chemical Formula 2-4]

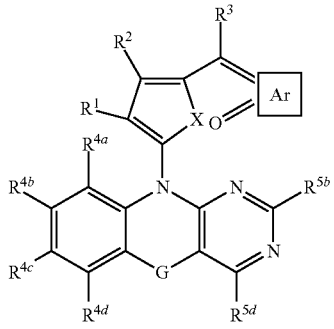

[Chemical Formula 2-5]

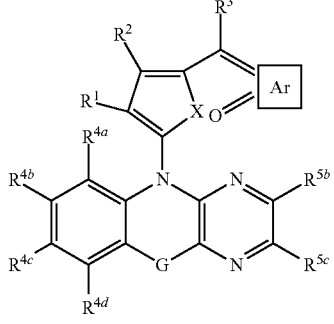

In Chemical Formula 2-1 to Chemical Formula 2-5,

Ar, X, $R^1$ to $R^3$, and G may be the same as in Chemical Formula 1, and $R^{4a}$ to $R^{4d}$ and $R^{5a}$ to $R^{5d}$ may be independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof.

In example embodiments, the structure may be represented by one of Chemical Formulae 5-1 to 5-4:

[Chemical Formula 5-1]

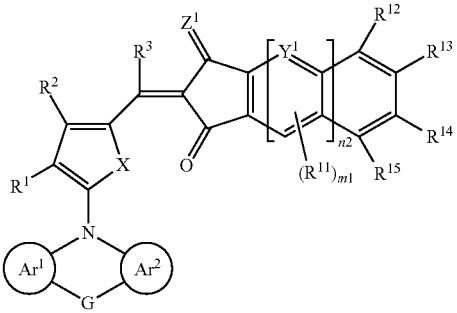

In Chemical Formula 5-1, $Z^1$ may be O or $CR^b R^c$ wherein each of $R^b$ and $R^c$ may be independently one of hydrogen, a substituted or unsubstituted C1 to C10 alkyl group, a cyano group, or a cyano-containing group, provided that at least one of $R^b$ and $R^c$ may be a cyano group or a cyano-containing group, $Y^1$ may be one of N and $CR^d$, wherein $R^d$ may be one of hydrogen and a substituted or unsubstituted C1 to C10 alkyl group, each of $R^{11}$, $R^{12}$, $R^{13}$, $R^{14}$, and $R^{15}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, or $R^{12}$ and $R^{13}$ (or $R^{14}$ and $R^{15}$) may be independently linked with each other to provide an aromatic ring, m1 may be 0 or 1, and n2 may be 0 or 1.

[Chemical Formula 5-2]

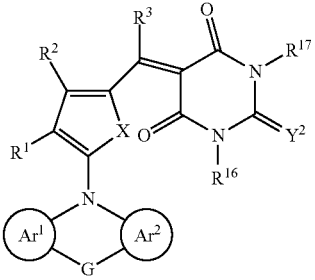

In Chemical Formula 5-2, $Y^2$ may be one of O, S, Se, Te, and $C(R^e)(CN)$ (wherein $R^e$ may be one of hydrogen, a cyano group (—CN), and a C1 to C10 alkyl group), and each of $R^{16}$ and $R^{17}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof.

[Chemical Formula 5-3]

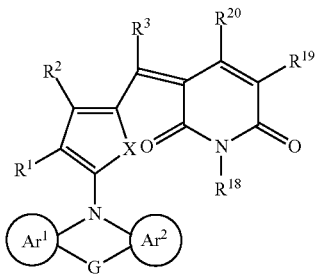

In Chemical Formula 5-3,
each of $R^{18}$, $R^{19}$, and $R^{20}$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof.

[Chemical Formula 5-4]

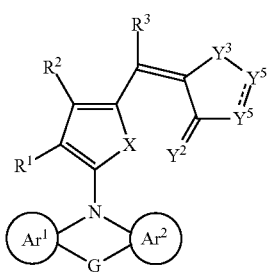

In Chemical Formula 5-4,
$Y^2$ may be one of O, S, Se, Te, and $C(R^e)(CN)$ (wherein $R^e$ may be one of hydrogen, a cyano group (—CN), and a C1 to C10 alkyl group),
$Y^3$ may be one of O, S, Se, and Te,
$Y^4$ may be N or $NR^f$,
$Y^5$ may be one of $CR^g$, C=O, C=S, $C=(CR^h)(CN)$, and a group represented by Chemical Formula 4-4',
when $Y^2$ is not O, $Y^5$ is C=O and when $Y^5$ is not C=O, $Y^2$ is O,
each of $R^f$, $R^g$, and $R^h$ may be independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and
if $Y^5$ is $CR^g$ or $C=(CR^h)(CN)$, $Y^4$ and $Y^5$ are linked with each other to provide a $Y^4$-$Y^5$-containing fused ring with the ring structure of Chemical Formula 5-4, or $Y^4$ and $Y^5$ are not part of a $Y^4$-$Y^5$-containing fused ring with the ring structure of Chemical Formula 5-4.

[Chemical Formula 4-4']

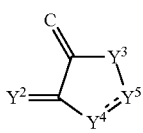

In Chemical Formula 4-4',
$Y^2$, $Y^3$, $Y^4$, and $Y^5$ are the same as in Chemical Formula 4-4.

In some example embodiments, an organic photoelectric device may include a first electrode and a second electrode facing each other, and an active layer between the first electrode and the second electrode. The active layer may include the compound.

In some example embodiments, an image sensor may include the organic photoelectric device on a semiconductor substrate.

DETAILED DESCRIPTION

Figure 1:
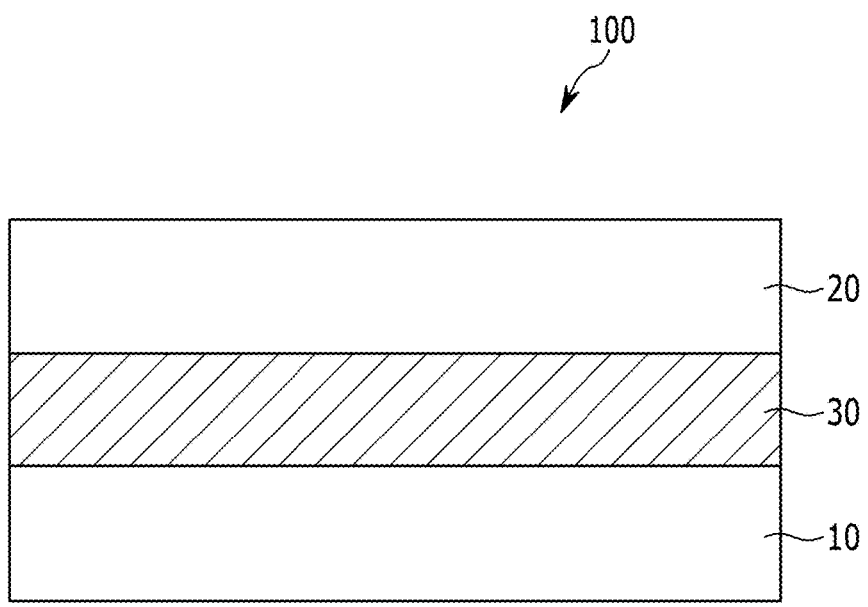
FIG. 1 is a cross-sectional view showing an organic photoelectric device according to some example embodiments.

Some example embodiments will hereinafter be described in detail, and may be easily performed by a person having an ordinary skill in, the related art. However, this disclosure may be embodied in many different forms and is not to be construed as limited to the presented embodiments.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, when specific definition is not otherwise provided, the term "substituted" refers to replacement of a hydrogen valence halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when specific definition is not otherwise provided, the term "hetero" refers to one including 1 to 3 heteroatoms selected from N, O, S, P, and Si.

As used herein, the term "alkyl group" for example refers to a methyl group, an ethyl group, a propyl group, an isopropyl group, an n-butyl group, an isobutyl group, a t-butyl group, a pentyl group, a hexyl group, and the like.

As used herein, the term "cycloalkyl group" for example refers to a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be a monocyclic, polycyclic or fused ring polycyclic (e.g., rings sharing adjacent pairs of carbon atoms) functional group.

As used herein, when a definition is not otherwise provided, the term "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as a dicyanoalkenyl group represented by $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10. Specific examples of the cyano-containing group may be a dicyanomethyl group, a dicyanovinyl group, a cyanoethynyl group, and the like As used herein, when a definition is not otherwise provided, the term "combination thereof" refers to at least two substituents bound to each other by a single bond or a C1 to C10 alkylene group, or at least two fused substituents.

As used herein, the term "5-membered aromatic ring" refers to a 5-membered ring group (e.g., C5 aryl group) having a conjugation structure or a 5-membered heterocyclic group (e.g., C2 to C4 heteroaryl group) having a conjugation structure. As used herein, the term "6-membered aromatic ring" refers to a 6-membered ring group (e.g., C6 aryl group) having a conjugation structure or a 6-membered heterocyclic group (e.g., C2 to C5 heteroaryl groups) having a conjugation structure, but is not limited thereto. The aromatic ring may include the 5-membered aromatic ring or the 6-membered aromatic ring, but is not limited thereto.

Hereinafter, a compound according to some example embodiments is described. The compound is represented by Chemical Formula 1.

[Chemical Formula 1]

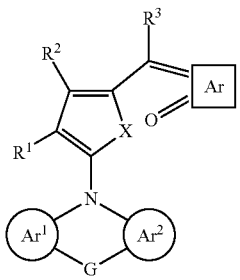

In Chemical Formula 1,

Ar is one of a substituted or unsubstituted 5-membered aromatic ring, a substituted or unsubstituted 6-membered aromatic ring, and a condensed ring of two or more of the foregoing rings, X is one of Se, Te, O, S(=O), S(=O)$_2$, NR$^a$, and SiR$^b$R$^c$ (wherein each of R$^a$, R$^b$, and R$^c$ are independently one of hydrogen and a substituted or unsubstituted C1 to C10 alkyl group), each of R$^1$ to R$^3$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, each of Ar$^1$ and Ar$^2$ are independently one of a substituted or unsubstituted C6 to C30 arylene group and a substituted or unsubstituted C3 to C30 heteroarylene group, a substituted or unsubstituted C6 to C30 arene group, and a substituted or unsubstituted C3 to C30 heteroarene group, and G is one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, and a substituted or unsubstituted C6 to C10 aryl group, and optionally R$^m$ and R$^n$ are linked to each other to provide a fused ring, and n is an integer of 1, or 2). The fused ring may be a 5-membered or 6-membered aromatic ring or a hetero aromatic ring.

The compound represented by Chemical Formula 1 includes an electron donor moiety of an N-containing hetero aromatic ring, a linker of an X-containing 5-membered ring and a methine group, and an electron acceptor moiety represented by Ar.

Ar$^1$ and Ar$^2$ of the N-containing hetero aromatic ring are linked by G and thereby provides one conjugation structure overall to improve thermal stability of the compound. Such a conjugation structure may be formed by fusing three to four 5-membered or 6-membered aromatic rings, but is not limited thereto.

Ar$^1$ and Ar$^2$ may be a substituted or unsubstituted C6 to C30 arylene group or a substituted or unsubstituted C3 to C30 heteroarylene group that is formed by fusing aromatic rings, For example, Ar$^1$ and Ar$^2$ may be a substituted or unsubstituted C6 to C20 arylene group or a substituted or unsubstituted C3 to C20 heteroarylene group. Ar$^1$ and Ar$^2$ may be a substituted or unsubstituted C6 to C30 arene group, and a substituted or unsubstituted C3 to C30 heteroarene group.

In some example embodiments, the arylene group may be selected from a phenylene group, a naphthalene group, and an anthracene group, for example the arylene group may be selected from a pyrrolyl group, a prazolyl group, an imidazolyl group, an oxazolyl group, an isoxazolyl group, a thiazolyl group, an isothiazolyl group, a pyridinyl group, a pyridazinyl group, a pyrimidinyl group, a pyrazinyl group, an indolyl group, a quinolinyl group, an isoquinolinyl group, an naphthyridinyl group, a cinnolinyl group, a quinazolinyl group, a phthalazinyl group, a benzotriazinyl group, a pyridopyrazinyl group, a pyridopyrimidinyl group, a pyridopyridazinyl group, a thienyl group, a benzothienyl group, a selenophenyl group, and a benzoselenophenyl group.

In Chemical Formula 1, an intramolecular interaction between X and oxygen (O) of a carbonyl group of the electron acceptor moiety may be increased and thereby an absorption intensity in a specific wavelength may be improved.

In Chemical Formula 1, at least one of $Ar^1$ and $Ar^2$ may include a heteroatom selected from nitrogen (N), sulfur (S), and selenium (Se) at No. 1 position. In this case, X, oxygen (O) of a carbonyl group of the electron acceptor moiety, and the heteroatom at No. 1 position in at least one of $Ar^1$ and $Ar^2$ increase an intramolecular interaction and thereby improve an absorption intensity in a specific wavelength.

The compound represented by Chemical Formula 1 may be represented by one of Chemical Formula 2-1 to Chemical Formula 2-5.

[Chemical Formula 2-1]

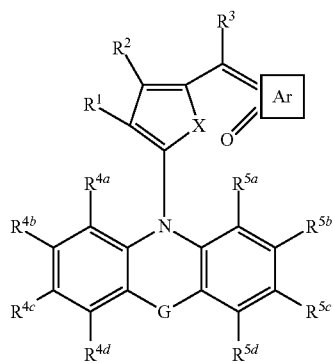

In Chemical Formula 2-1,

Ar, X, $R^1$ to $R^3$, and G are the same as in Chemical Formula 1, each of $R^{4a}$ to $R^{4d}$ and $R^{5a}$ to $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof, or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

[Chemical Formula 2-2]

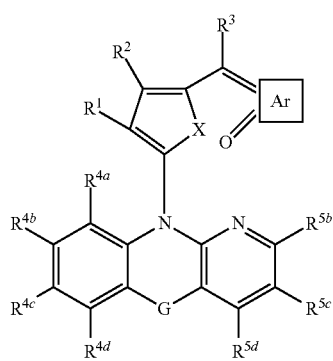

In Chemical Formula 2-2,

Ar, X, $R^1$ to $R^3$, and G are the same as in Chemical Formula 1, and $R^{4a}$ to $R^{4d}$ and $R^{5a}$ to $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof, or optionally two adjacent groups of $R^{4a}$ to $R^{4d}$ are linked with each other to provide a 5-membered aromatic ring or a 6-membered aromatic ring and optionally two adjacent groups of $R^{5a}$ to $R^{5d}$ are linked with each other to provide a 5-membered aromatic ring or a 6-membered aromatic ring.

[Chemical Formula 2-3]

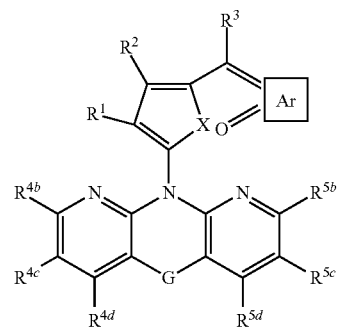

In Chemical Formula 2-3,

Ar, X, $R^1$ to $R^3$, and G are the same as in Chemical Formula 1, and $R^{4b}$ to $R^{4d}$ and $R^{5b}$ to $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof or optionally two adjacent groups of $R^{4b}$ to $R^{4d}$ are linked with each other to provide a 5-membered aromatic ring or a 6-membered aromatic ring and optionally two adjacent groups of $R^{5b}$ to $R^{5d}$ are linked with each other to provide a 5-membered aromatic ring or a 6-membered aromatic ring.

[Chemical Formula 2-4]

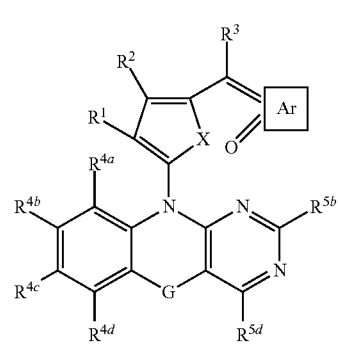

In Chemical Formula 2-4,

Ar, X, $R^1$ to $R^3$, and G are the same as in Chemical Formula 1, $R^{4a}$ to $R^{4d}$ and $R^{5b}$ and $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof, or optionally two adjacent groups of $R^{4a}$ to $R^{4d}$ are linked with each other to provide a 5-membered aromatic ring or a 6-membered aromatic ring.

[Chemical formula 2-5]

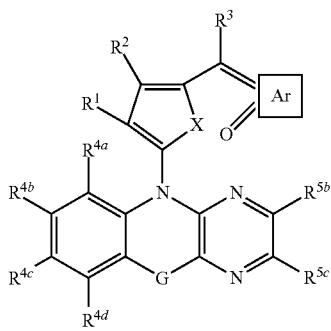

In Chemical Formula 2-5,

Ar, X, $R^1$ to $R^3$, and G are the same as in Chemical Formula 1, $R^{4a}$ to $R^{4d}$ and $R^{5b}$ and $R^{5c}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof, or optionally two adjacent groups of $R^{4a}$ to $R^{4d}$ are linked with each other to provide a 5-membered aromatic ring or a 6-membered aromatic ring and optionally $R^{5b}$ and $R^{5c}$ are linked with each other to provide a 5-membered aromatic ring or a 6-membered aromatic ring.

In Chemical Formulae 1 and 2-1 to 2-5, a ring group represented by Ar is an electron acceptor moiety including at least one carbonyl group.

For example, in Chemical Formulae 1 and 2-1 to 2-5, the ring group represented by Ar bound to the methine group may include one or two carbonyl groups.

For example, in Chemical Formulae 1 and 2-1 to 2-5, the ring group represented by Ar bound to the methine group may include at least one carbonyl group and at least one cyano-containing moiety.

In Chemical Formulae 1 and 2-1 to 2-5, the ring group represented by Ar and bound to a methine group may be represented by Chemical Formula 3.

[Chemical Formula 3]

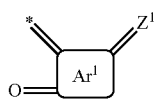

In Chemical Formula 3,

Ar' is one of a substituted or unsubstituted 5-membered aromatic ring, a substituted or unsubstituted 6-membered aromatic ring, and a condensed ring of two or more of the foregoing rings, and $Z^1$ is O or $CR^bR^c$, wherein each of $R^b$ and $R^c$ are independently one of hydrogen, a substituted or unsubstituted C1 to C10 alkyl group, a cyano group, or a cyano-containing group, provided that at least one of $R^b$ and $R^c$ is a cyano group or a cyano-containing group.

For example, the ring group represented by Ar and bound to a methine group may be a condensed ring of a substituted or unsubstituted 5-membered aromatic ring and a substituted or unsubstituted 6-membered aromatic ring.

In Chemical Formula 1 and Chemical Formulae 2-1 to 2-5, the ring group represented by Ar bound to the methine group may be a ring group represented by one of Chemical Formulae 4-1 to 4-4.

[Chemical Formula 4-1]

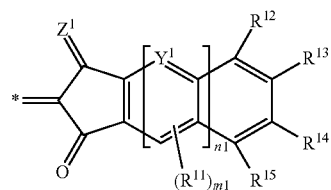

In Chemical Formula 4-1, $Z^1$ is O or $CR^bR^c$ wherein each of $R^b$ and $R^c$ are independently one of hydrogen, a substituted or unsubstituted C1 to C10 alkyl group, a cyano group, or a cyano-containing group, provided that at least one of $R^b$ and $R^c$ is a cyano group or a cyano-containing group, $Y^1$ is one of N and $CR^d$, wherein $R^d$ is one of hydrogen and a substituted or unsubstituted C1 to C10 alkyl group, $R^{11}$, $R^{12}$, $R^{13}$, $R^{14}$, and $R^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, or $R^{12}$ and $R^{13}$ are independently linked with each other to provide an aromatic ring and $R^{14}$ and $R^{15}$ are independently linked with each other to provide an aromatic ring, m1 is 0 or 1, n1 is 0 or 1, and

* indicates a linking position with a methine group.

[Chemical Formula 4-2]

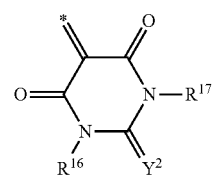

In Chemical Formula 4-2, $Y^2$ is one of O, S, Se, Te, and $C(R^e)(CN)$ wherein $R^e$ is one of hydrogen, a cyano group (—CN), and a C1 to C10 alkyl group, $R^{16}$ and $R^{17}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), and a combination thereof, and

* indicates a linking position with a methine group.

[Chemical Formula 4-3]

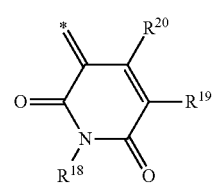

In Chemical Formula 4-3, $R^{18}$ to $R^{20}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and

* indicates a linking position with a methine group.

[Chemical Formula 4-4]

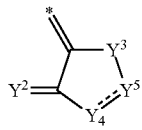

In Chemical Formula 4-4, $Y^2$ is one of O, S, Se, Te, and $C(R^e)(CN)$ (wherein $R^e$ is one of hydrogen, a cyano group (—CN), and a C1 to C10 alkyl group), $Y^3$ is one of O, S, Se, and Te, $Y^4$ is N or $NR^f$, $Y^5$ is one of $CR^g$, C=O, C=S, C=$(CR^h)(CN)$, and a group represented by Chemical Formula 4-4', when $Y^2$ is not O, $Y^5$ is C=O and when $Y^5$ is not C=O, $Y^2$ is O, $R^f$, $R^g$, and $R^h$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and if $Y^5$ is $CR^g$ or C=$(CR^h)(CN)$, $Y^4$ and $Y^5$ may be linked with each other to provide a $Y^4$-$Y^5$-containing fused ring with of the ring structure of Chemical Formula 5-4, or $Y^4$ and $Y^5$ may not be linked with each other, and

* indicates a linking position with a methine group.

[Chemical Formula 4-4']

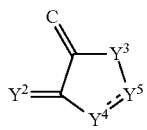

In Chemical Formula 4-4', $Y^2$, $Y^3$, $Y^4$, and $Y^5$ are the same as in Chemical Formula 4-4.

The ring group represented by Chemical Formula 4-1 may be for example a ring group represented by Chemical Formula 4-1-1, 4-1-2, or 4-1-3.

[Chemical Formula 4-1-1]

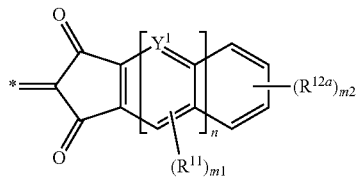

[Chemical Formula 4-1-2]

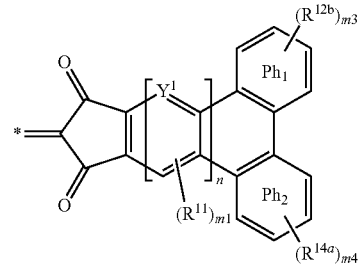

[Chemical Formula 4-1-3]

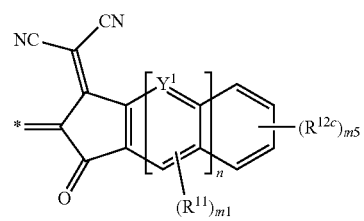

In Chemical Formulae 4-1-1, 4-1-2, and 4-1-3, $Y^1$, $R^{11}$, m1, and n are the same as in Chemical Formula 4-1, $R^{12a}$, $R^{12b}$, $R^{12c}$, and $R^{14a}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, m2, m3, m4, and m5 are independently an integer ranging from 0 to 4, and Ph1 and Ph2 denote a fused phenylene ring, provided that one of Ph1 and Ph2 may be optionally omitted.

The ring group represented by Chemical Formula 4-2 may be for example a ring group represented by Chemical Formula 4-2-1 or 4-2-2.

[Chemical Formula 4-2-1]

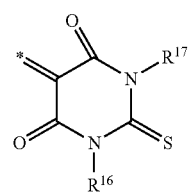

[Chemical Formula 4-2-2]

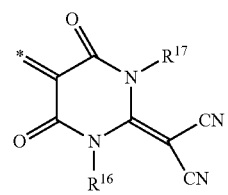

In Chemical Formulae 4-2-1 and 4-2-2, $R^{16}$ and $R^{17}$ are the same as in Chemical Formula 4-2.

The ring group represented by Chemical Formula 4-3 may be for example a ring group represented by Chemical Formula 4-3-1 or 4-3-2.

[Chemical Formula 4-3-1]

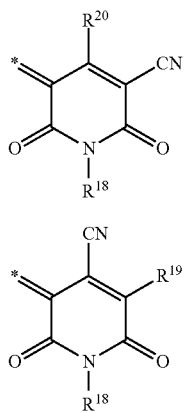

[Chemical Formula 4-3-2]

In Chemical Formulae 4-3-1 and 4-3-2, $R^{18}$ to $R^{20}$ are the same as in Chemical Formula 4-3

The ring group represented by Chemical Formula 4-4 may be for example a ring group represented by Chemical Formula a 4-4-1, 4-4-2, 4-4-3, or 4-4-4.

[Chemical Formula 4-4-1]

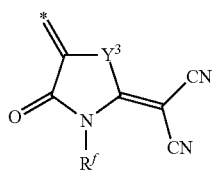

[Chemical Formula 4-4-2]

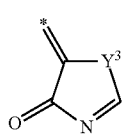

[Chemical Formula 4-4-3]

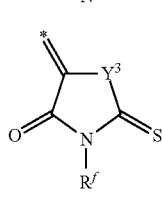

[Chemical Formula 4-4-4]

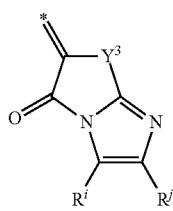

In Chemical Formulae 4-4-1, 4-4-2, 4-4-3, and 4-4-4, $Y^3$ and $R^f$ are the same as in Chemical Formula 4-4, and in Chemical Formula 4-4-4, $R^i$ and $R^j$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, or optionally $R^i$ and $R^j$ are linked with each other to provide a fused ring. The fused ring may be a 5-membered or 6-membered aromatic ring or a hetero aromatic ring.

The compound may be a compound represented by one of Chemical Formulae 5-1 to 5-4.

[Chemical Formula 5-1]

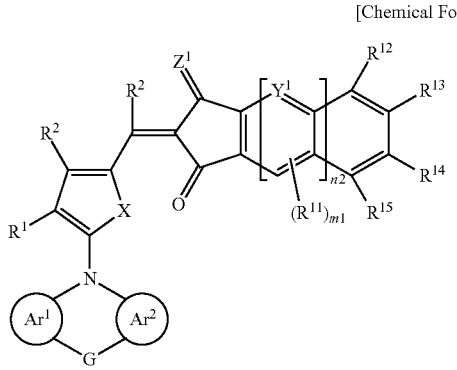

In Chemical Formula 5-1,

X is one of Se, Te, O, S(=O), S(=O)$_2$, NR$^a$, and SiR$^b$R$^c$ (wherein each of R$^a$, R$^b$, and R$^c$ are independently one of hydrogen and a substituted or unsubstituted C1 to C10 alkyl group), each of $R^1$ to $R^3$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, each of Ar$^1$ and Ar$^2$ are independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, and G is one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, and a substituted or unsubstituted C6 to C10 aryl group, and optionally R$^m$ and R$^n$ are linked to each other to provide a fused ring, and n is an integer of 1, or 2), $Z^1$ is O or CR$^b$R$^c$ wherein each of R$^b$ and R$^c$ are independently one of hydrogen, a substituted or unsubstituted C1 to C10 alkyl group, a cyano group, or a cyano-containing group, provided that at least one of R$^b$ and R$^c$ is a cyano group or a cyano-containing group, $Y^1$ is one of N and CR$^d$, wherein R$^d$ is one of hydrogen and a substituted or unsubstituted C1 to C10 alkyl group, $R^{11}$, $R^{12}$, $R^{13}$, $R^{14}$, and $R^{15}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof or $R^{12}$ and $R^{13}$ are independently linked with each other to provide an aromatic ring and $R^{14}$ and $R^{15}$ are independently linked with each other to provide an aromatic ring, m1 is 0 or 1, and n2 is 0 or 1.

[Chemical Formula 5-2]

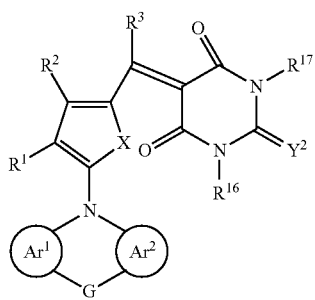

In Chemical Formula 5-2,

X is one of Se, Te, O, S(=O), S(=O)$_2$, NR$^a$, and SiR$^b$R$^c$ (wherein each of R$^a$, R$^b$, and R$^c$ are independently one of hydrogen and a substituted or unsubstituted C1 to C10 alkyl group), each of Ar$^1$ and Ar$^2$ are independently one of a substituted or unsubstituted C6 to C30 arylene group, a substituted or unsubstituted C3 to C30 heteroarylene group, a substituted or unsubstituted C6 to C30 arene group, and a substituted or unsubstituted C3 to C30 heteroarene group, G is one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))— (wherein each of R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, and a substituted or unsubstituted C6 to C10 aryl group, and optionally R$^m$ and R$^n$ are linked to each other to provide a fused ring, and n is an integer of 1, or 2), Y$^2$ is one of O, S, Se, Te, and C(R$^e$)(CN) (wherein R$^e$ is one of hydrogen, a cyano group (—CN), and a C1 to C10 alkyl group), and each of R$^1$, R$^2$, R$^3$, R$^{16}$, and R$^{17}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof.

[Chemical Formula 5-3]

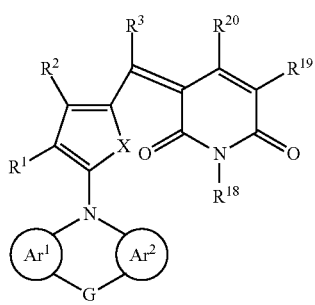

In Chemical Formula 5-3,

X is one of Se, Te, O, S(=O), S(=O)$_2$, NR$^a$, and SiR$^b$R$^c$ (wherein each of R$^a$, R$^b$, and R$^c$ are independently one of hydrogen and a substituted or unsubstituted C1 to C10 alkyl group), each of R$^1$, R$^2$, R$^3$, R$^{18}$, R$^{19}$, and R$^{20}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, each of Ar$^1$ and Ar$^2$ are independently one of a substituted or unsubstituted C6 to C30 arylene group and a substituted or unsubstituted C3 to C30 heteroarylene group, a substituted or unsubstituted C6 to C30 arene group, and a substituted or unsubstituted C3 to C30 heteroarene group, and G is one of a direct bond, —(CR$^d$R$^e$)$_n$—, —O—, —S—, —Se—, —N=, —NR$^f$—, —SiR$^g$R$^h$—, —GeR$^i$R$^j$—, and —(C(R$^m$)=C(R$^n$))—. (wherein each of R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, and a substituted or unsubstituted C6 to C10 aryl group, and optionally R$^m$ and R$^n$ are linked to each other to provide a fused ring, and n is an integer of 1, or 2).

[Chemical Formula 5-4]

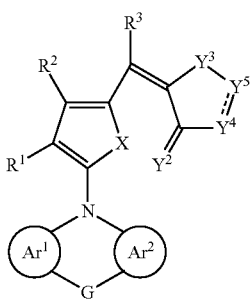

X is one of Se, Te, O, S(=O), S(=O)$_2$, NR$^a$, and SiR$^b$R$^c$ (wherein each of R$^a$, R$^b$, and R$^c$ are independently one of hydrogen and a substituted or unsubstituted C1 to C10 alkyl group), Y$^2$ is one of O, S, Se, Te, and C(R$^e$)(CN) (wherein R$^e$ is one of hydrogen, a cyano group (—CN), and a C1 to C10 alkyl group), Y$^3$ is one of O, S, Se, and Te, Y$^4$ is N or NR$^f$, Y$^5$ is one of CR$^g$, C=O, C=S, C=(CR$^h$)(CN), and a group represented by Chemical Formula 4-4', when Y$^2$ is not O, Y$^5$ is C=O and when Y$^5$ is not C=O, Y$^2$ is O, each of R$^1$, R$^2$, R$^3$, R$^f$, R$^g$, and R$^h$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, and if Y$^5$ is CR$^g$ or C=(CR$^h$)(CN), Y$^4$ and Y$^5$ may be linked with each other to provide a Y$^4$-Y$^5$-containing fused ring with of the ring structure of Chemical Formula 5-4, or Y$^4$ and Y$^5$ may not be linked with each other.

[Chemical Formula 4-4']

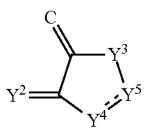

In Chemical Formula 4-4,
$Y^2$, $Y^3$, $Y^4$, and $Y^5$ are the same as in Chemical Formula 4-4.
The compound of Chemical Formula 1 may be, for example one of compounds represented by Chemical Formulae 6-1, Chemical Formula 6-2, Chemical Formula 6-3, and Chemical Formula 6-4, but is not limited thereto.
[Chemical Formula 6-1]
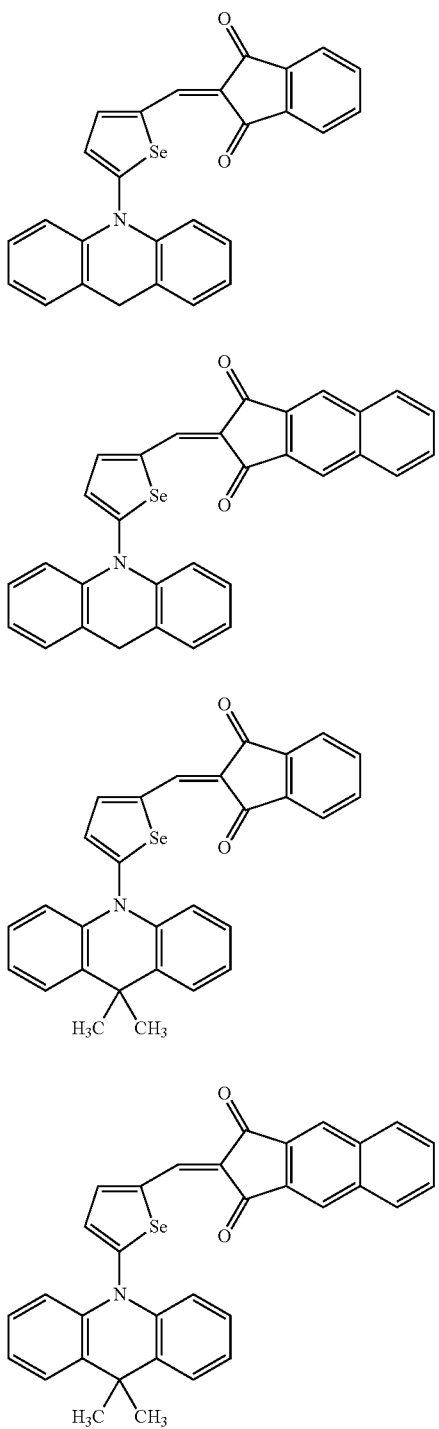
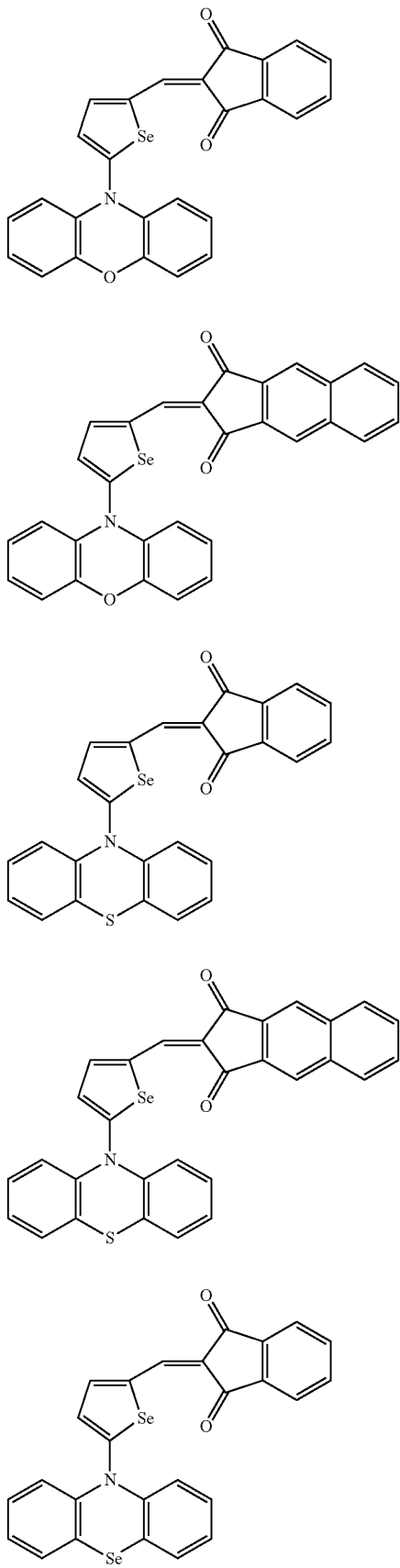

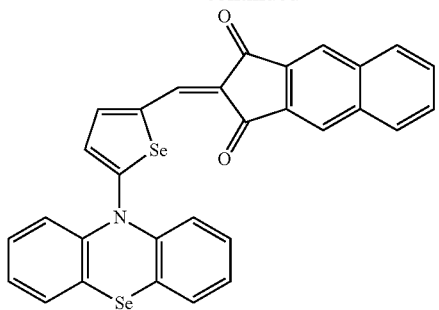
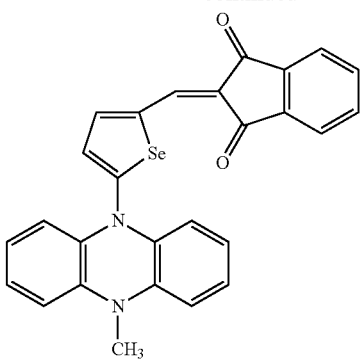
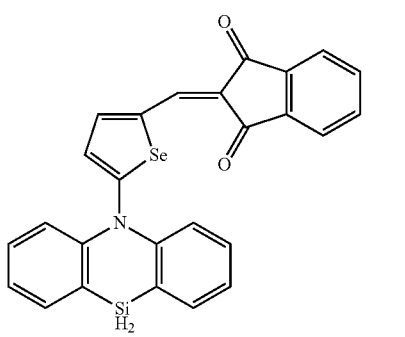
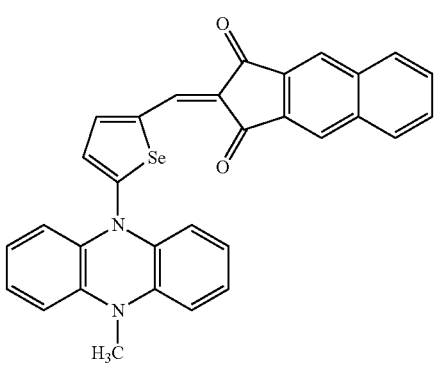
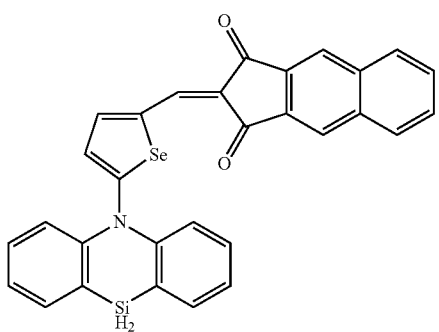
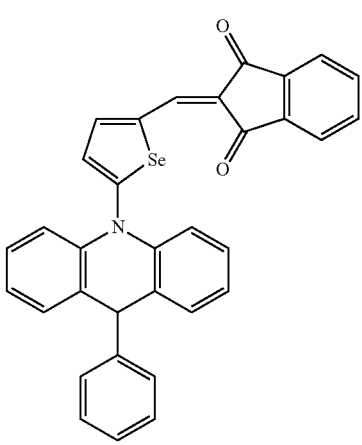
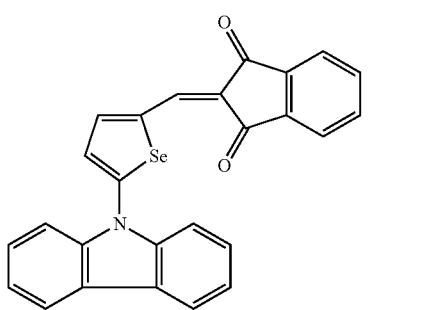
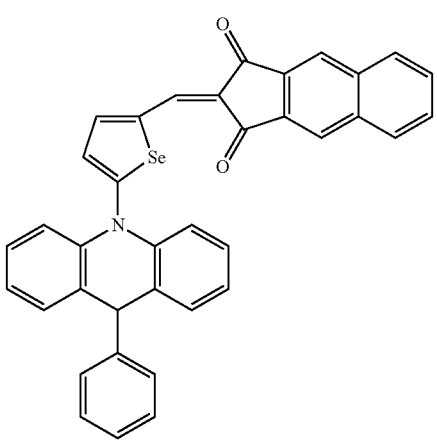
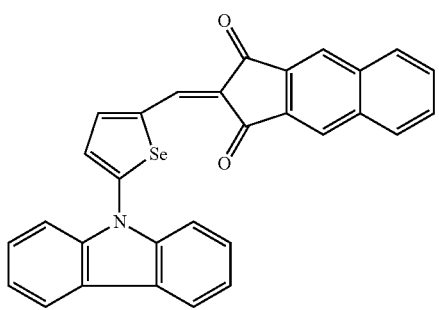

31
-continued
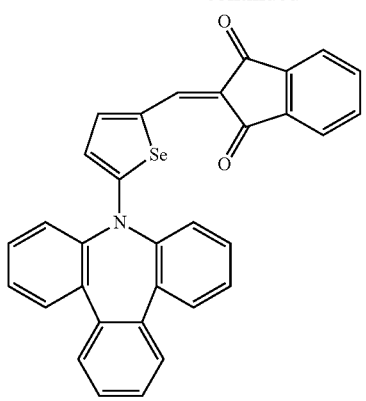
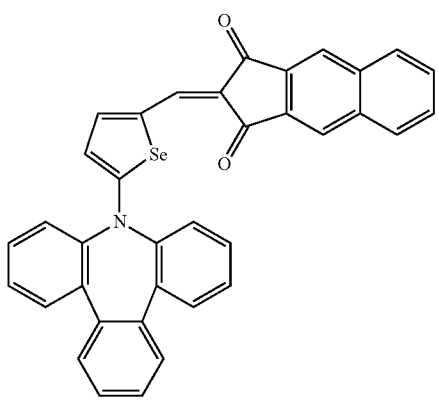
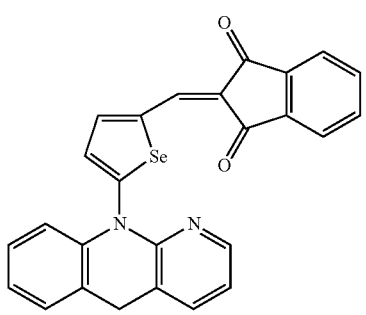
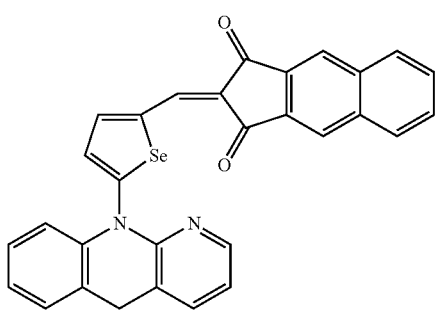
32
-continued
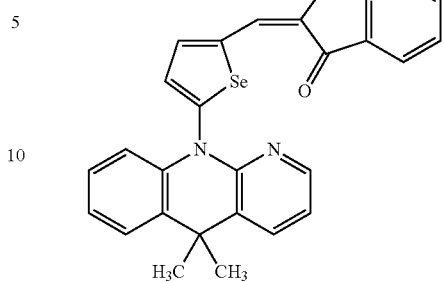
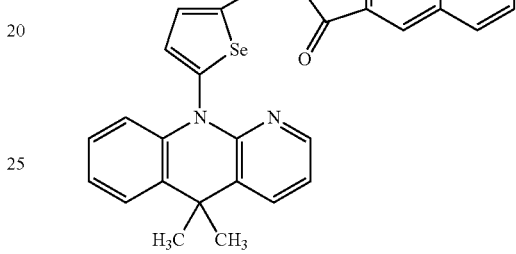
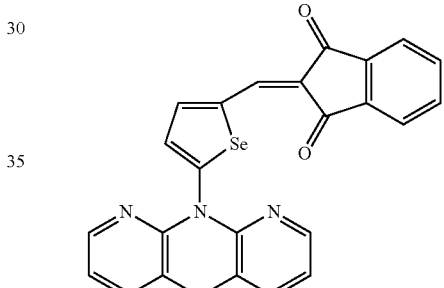
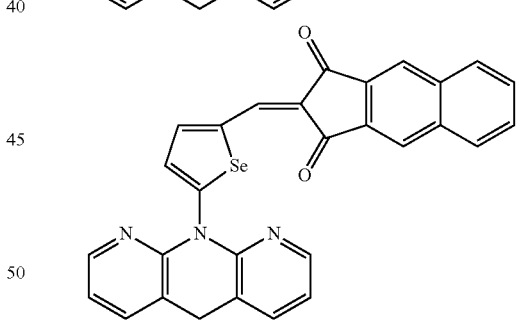
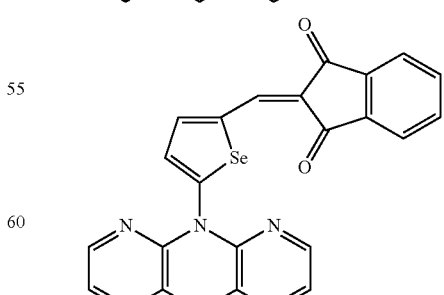
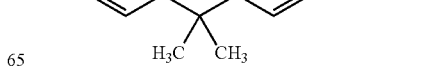

33
-continued
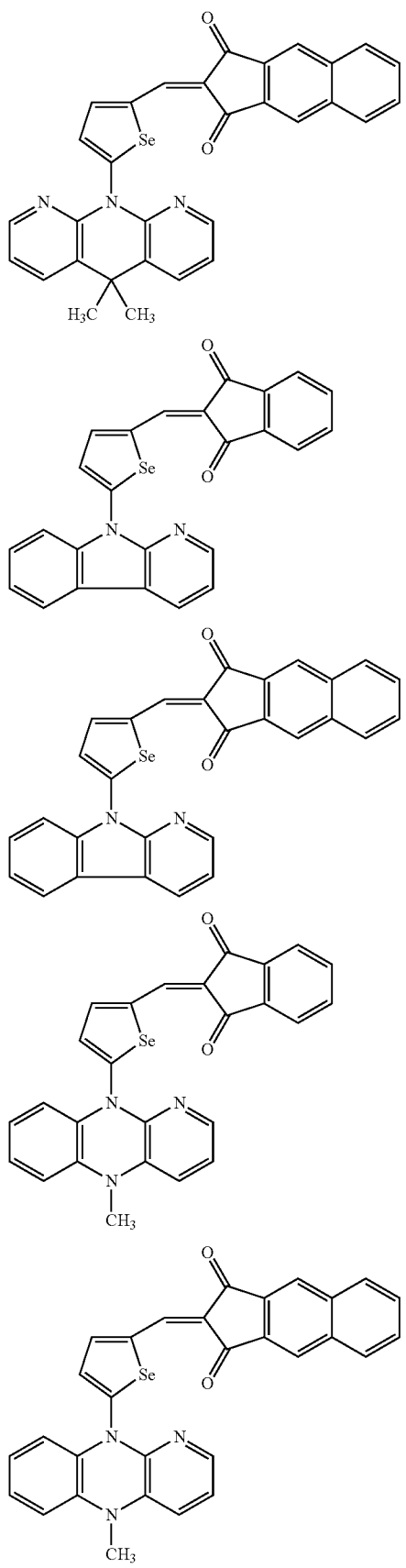
34
-continued
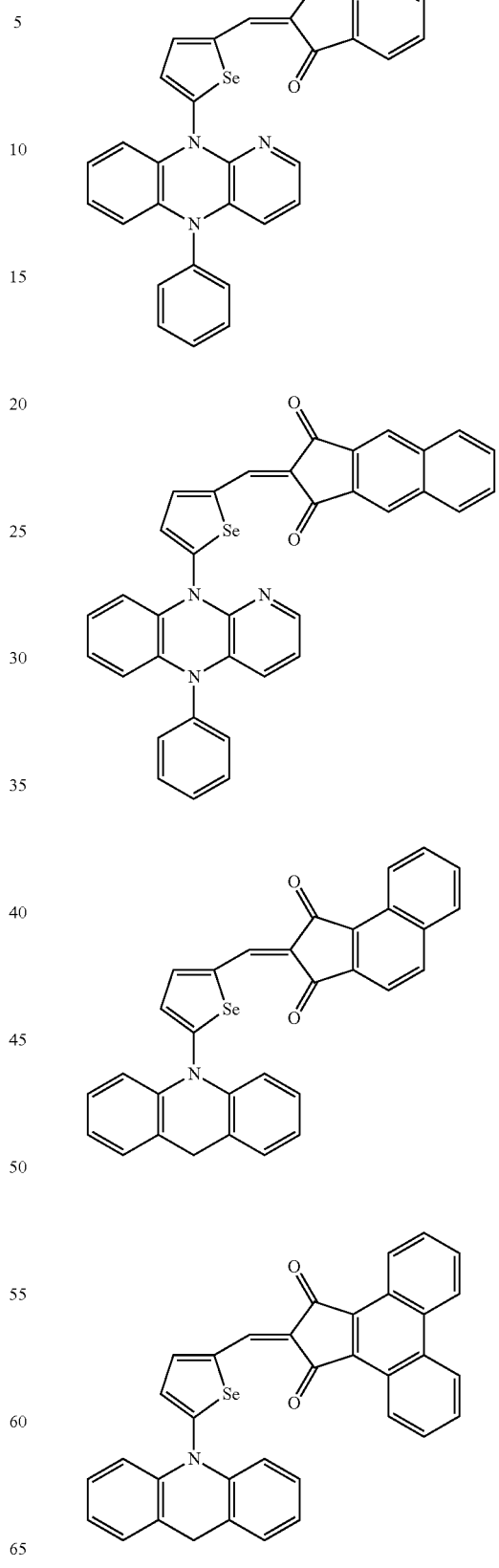

-continued
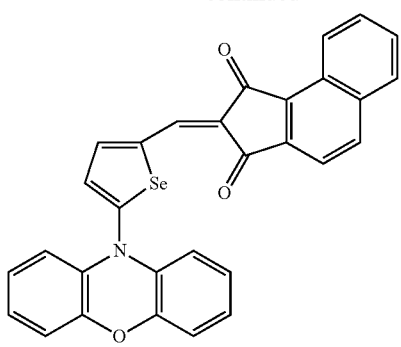
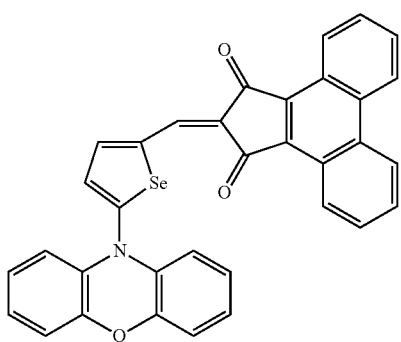
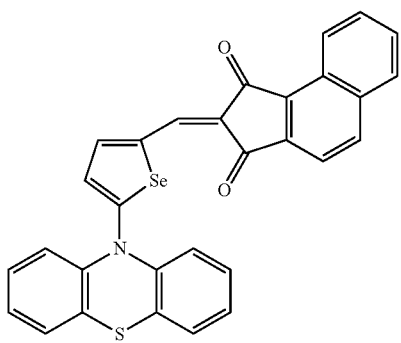
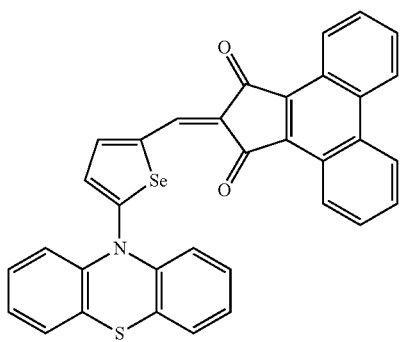
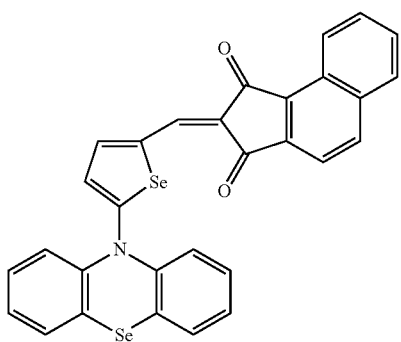
-continued
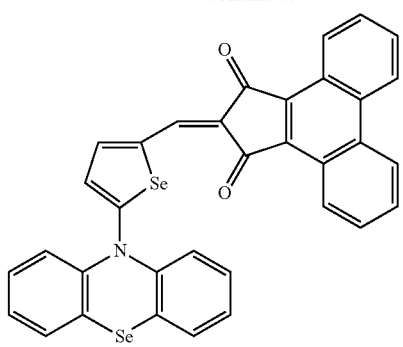
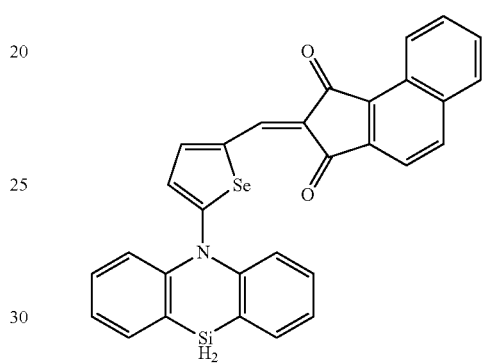
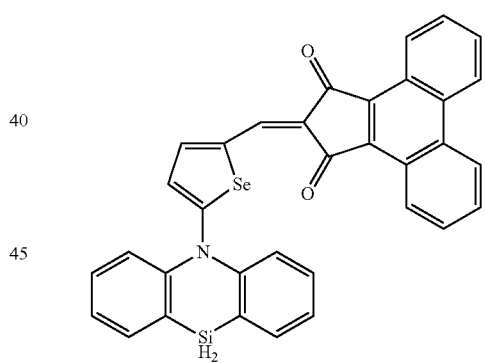
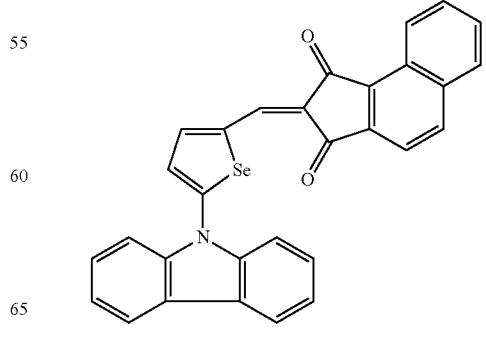

-continued

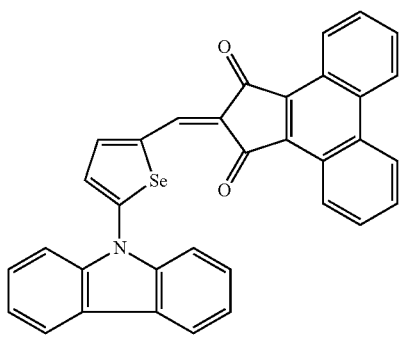

In Chemical Formula 6-1, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6-2]

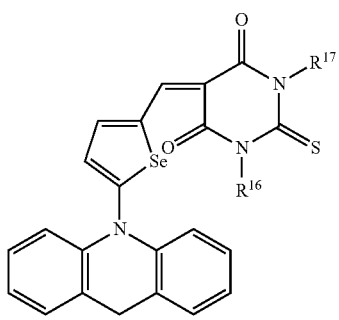

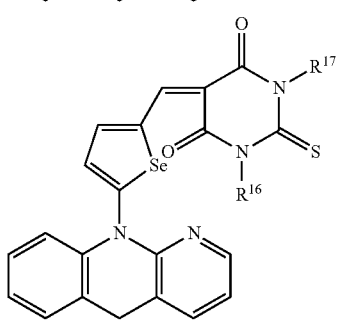

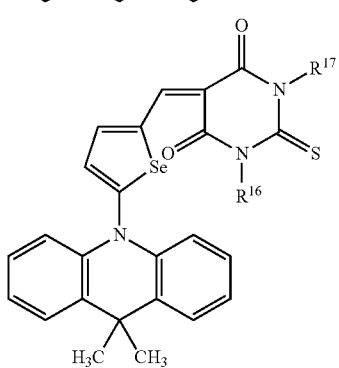

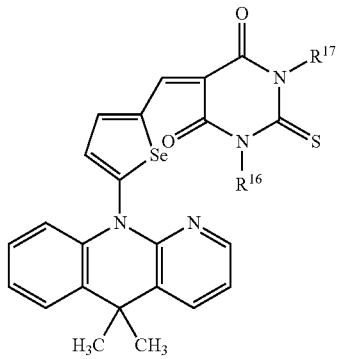

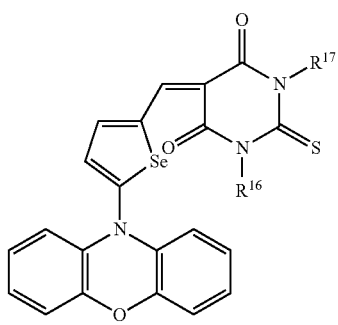

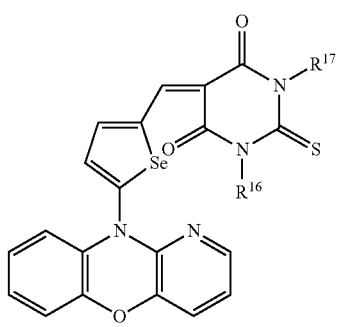

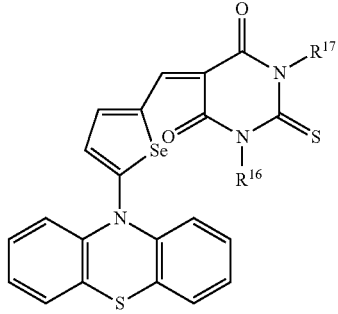

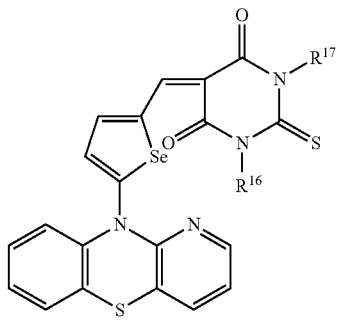

-continued
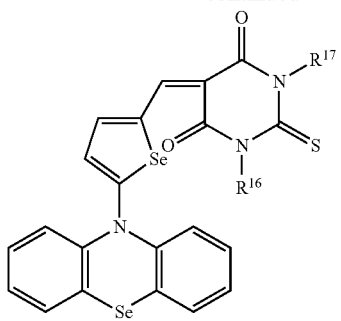
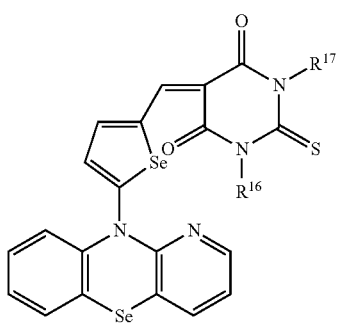
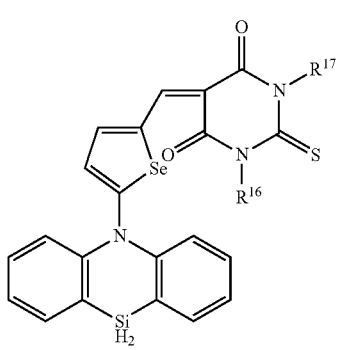
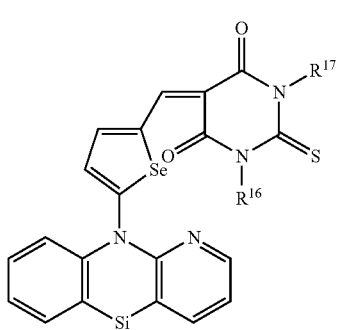
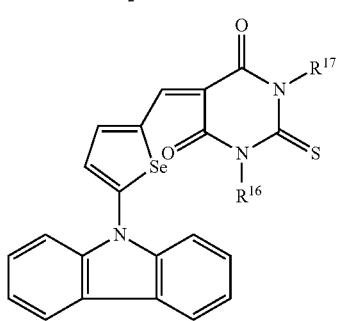
-continued
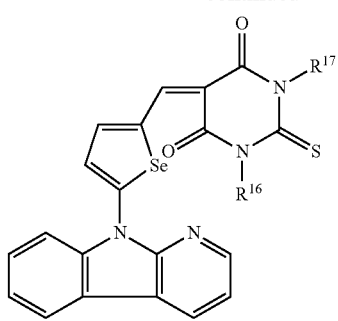
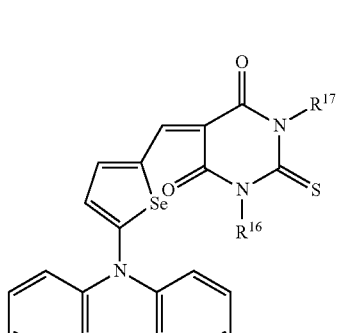
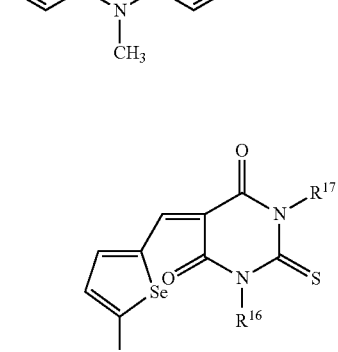
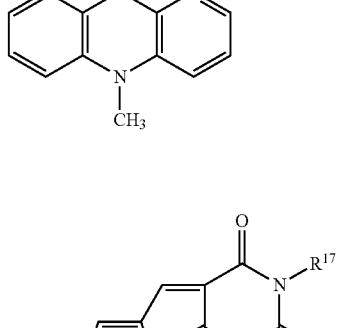
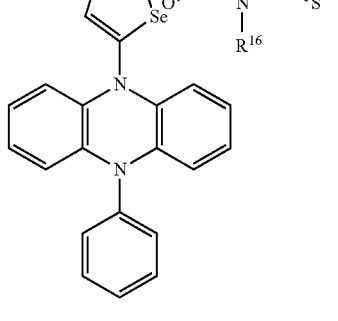

[Chemical Formula 6-3]

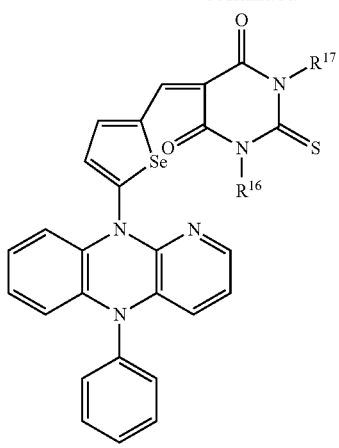
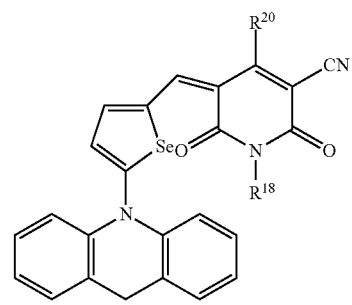
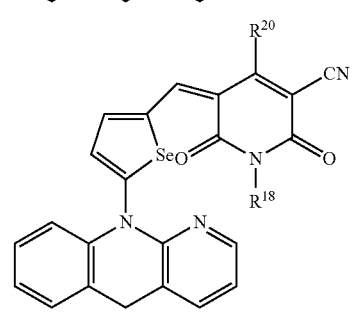
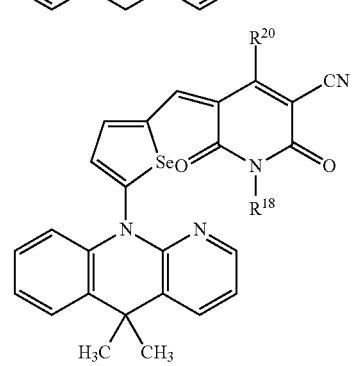
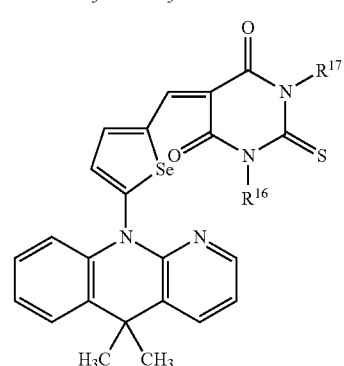
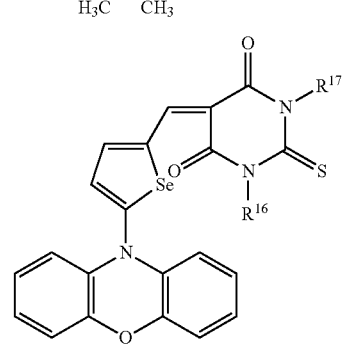

In Chemical Formula 6-2, $R^{16}$ and $R^{17}$ are the same as in Chemical Formula 5-2, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

43
-continued

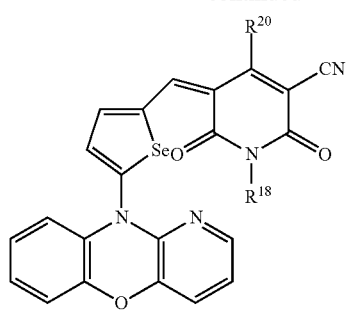

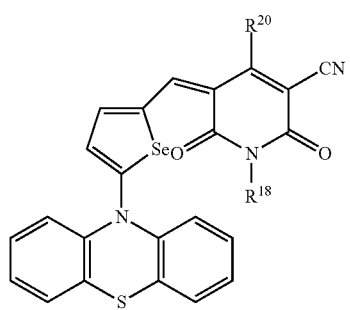

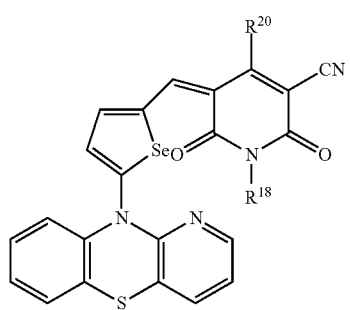

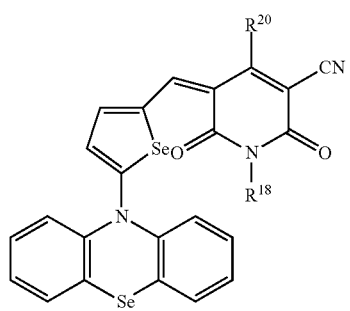

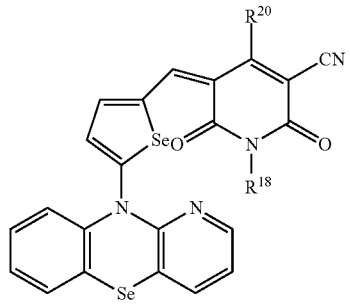

44
-continued

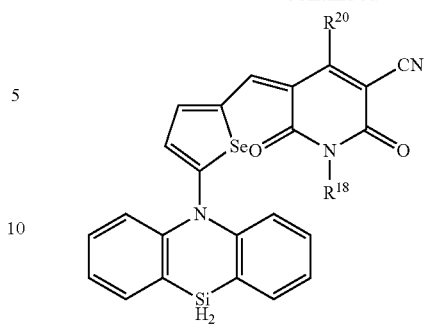

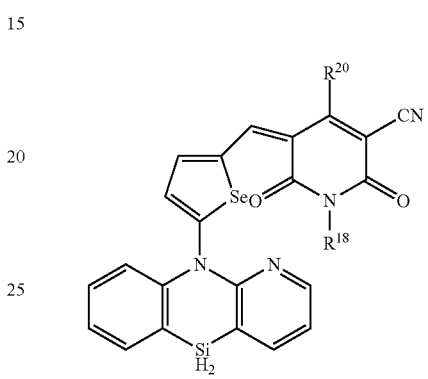

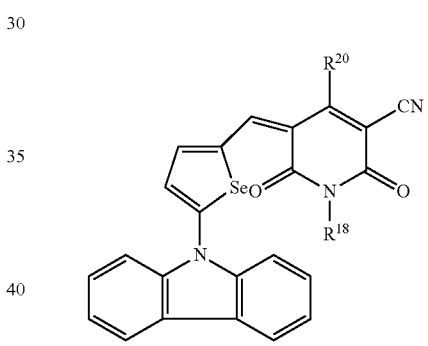

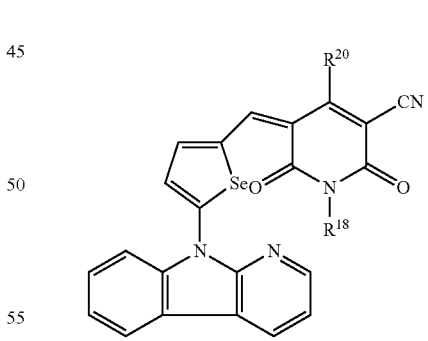

In Chemical Formula 6-3, $R^{18}$ and $R^{20}$ are the same as in Chemical Formula 4-3, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6-4]
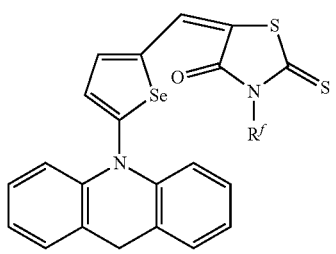
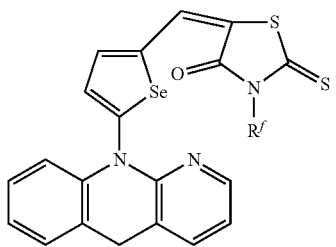
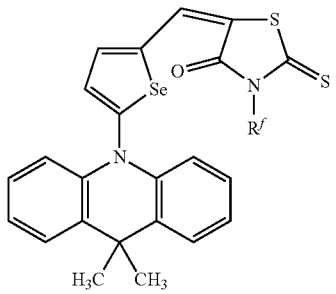
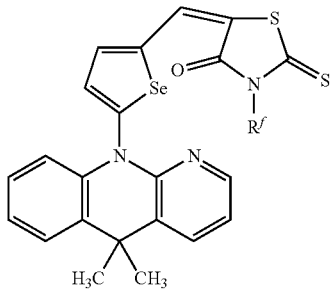
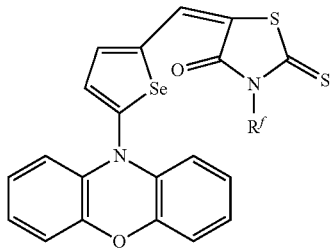
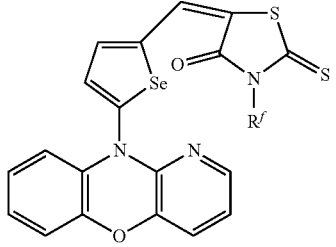
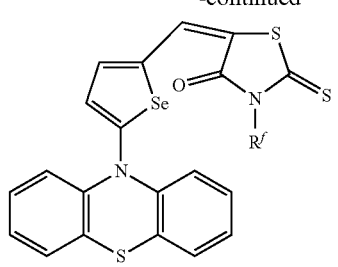
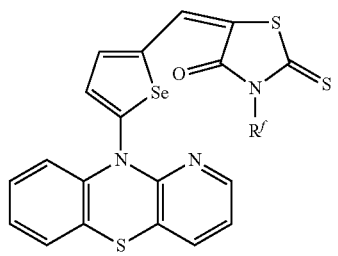
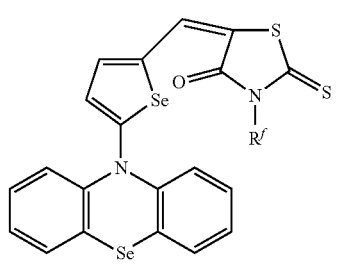
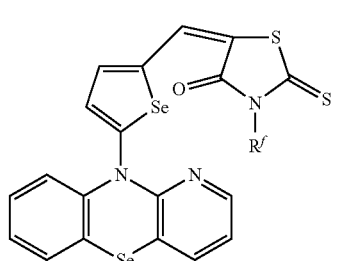
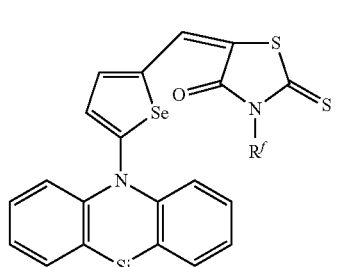
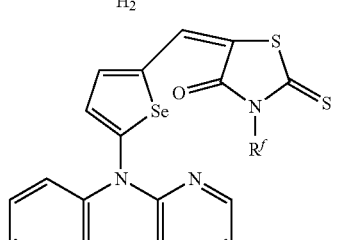

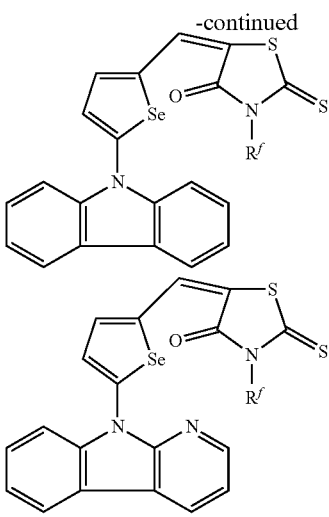

In Chemical Formula 6-4,

R$^f$ is the same as in Chemical Formula 4-4, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br or I), a cyano group (—CN), a cyano-containing group, and a combination thereof.

The compound is a compound selectively absorbing light in a green wavelength region, and may have a maximum absorption wavelength ($\lambda_{max}$) in a wavelength region of greater than or equal to about 510 nm and less than about 560 nm, for example about 520 nm to about 555 nm. Particularly, when it has a maximum absorption wavelength ($\lambda_{max}$) in a wavelength region of about 520 nm to about 555 nm, a color difference (ΔE*ab) may be reduced.

The compound may exhibit a light absorption curve having a full width at half maximum (FWHM) of about 50 nm to about 120 nm, in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound has, for example, greater than or equal to about 10° C. a higher melting point than the deposition temperature and thus may be desirably used for the deposition.

Specifically, a donor/acceptor-type material represented by Chemical Formula 1 may be thermally decomposed at its melting point (Tm). Accordingly, when the material has a lower Tm than a sublimation temperature (Ts) at which the material is vacuum-deposited to form a film, the material may be decomposed before sublimated (deposited) and not be used to manufacture a device. Since this material is not be appropriate for manufacturing a stable image sensor, Tm should be higher than Ts, and desirably, Tm−Ts≥10° C.

In addition, a micro lens array (MLA) needs to be formed to concentrate light after manufacturing an organic photoelectric device during manufacture of an image sensor. This micro lens array requires a relatively high temperature (about 160° C.), and this heat treatment may deteriorate performance of the organic photoelectric device. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be limited and/or prevented from the deterioration by the heat treatment. The compound has a cross-linking structure at a donor region and may be suppressed from the thermal agitation of molecules and stably maintained during the MLA heat treatment and thus secure process stability.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.0 eV to about 5.8 eV and an energy bandgap ranging from about 1.9 eV to about 2.3 eV, the LUMO level of the compound is in a range of about 3.9 eV to about 2.7 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiment, in view of a thin film formation, a stably depositable compound is desirable and thus the compound has a molecular weight of about 300 to about 1500. However, even though the compound has a molecular weight out of the range, a depositable compound may be used without limitation. In addition, when the compound is formed to form a thin film using a coating process, a compound that is dissolved in a solvent and coated may be used without limitation.

The compound may be a p-type semiconductor compound.

Hereinafter, an organic photoelectric device including the compound according to some example embodiments is described with reference to drawings.

FIG. 1 is a cross-sectional view showing an organic photoelectric device according to some example embodiments.

Referring to FIG. 1, an organic photoelectric device 100 according to some example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 500 nm and less than about 600 nm, for example about 520 nm to about 555 nm.

The active layer 30 may exhibit a light absorption curve having a relatively narrow full width at half maximum (FWHM) of about 50 nm to about 120 nm, for example about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$ when including the compound Chemical Formula 0.1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine or the sub-phthalocyanine derivative may be represented by Chemical Formula 7.

[Chemical Formula 7]

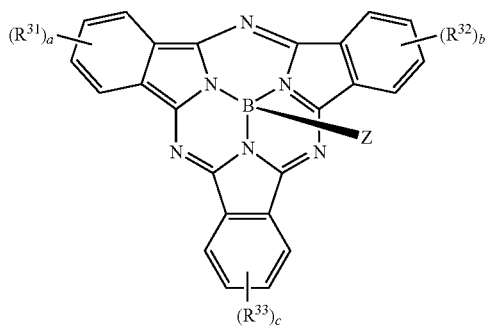

In Chemical Formula 7, $R^{31}$ to $R^{33}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, and a combination thereof, a, b, and c are integers ranging from 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group where at least one of hydrogen is replaced by F, Cl, Br, or I.

The thiophene derivative may be for example represented by Chemical Formula 8 or 9, but is not limited thereto.

[Chemical Formula 8]

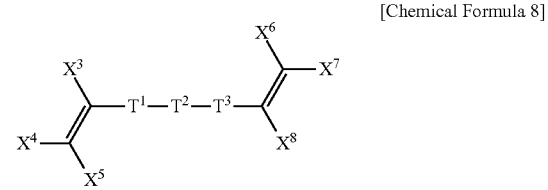

[Chemical Formula 9]

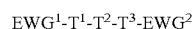

In Chemical Formulae 8 and 9, $T^1$, $T^2$, and $T^3$ are aromatic rings including substituted or unsubstituted thiophene moieties, $T^1$, $T^2$, and $T^3$ are independently present or are fused to each other, $X^3$ to $X^8$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are independently electron withdrawing groups.

For example, in Chemical Formula 8, at least one of $X^3$ to $X^8$ is an electron withdrawing group, for example a cyano-containing group.

The active layer 30 may further include a second p-type semiconductor compound selectively absorbing green light. The p-type semiconductor compound may be a compound represented by Chemical Formula 10.

[Chemical Formula 10]

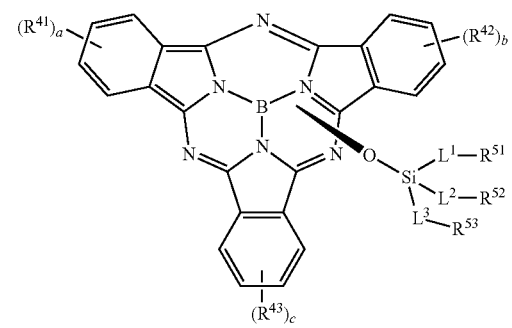

In Chemical Formula 10, $R^{41}$ to $R^{43}$ are independently one of hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, thiol group, a substituted or unsubstituted C6 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are independently a single bond, a substituted or unsubstituted C1 to C30 alkylene group, a substituted or unsubstituted C6 to C30 arylene group, divalent substituted or unsubstituted C3 to C30 heterocyclic group, or a combination thereof, $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light in a desired (and/or alternatively predetermined) wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the organic photoelectric device.

Hereinafter, an organic photoelectric device according to some example embodiments is described with reference to FIG. 2.

Figure 2:
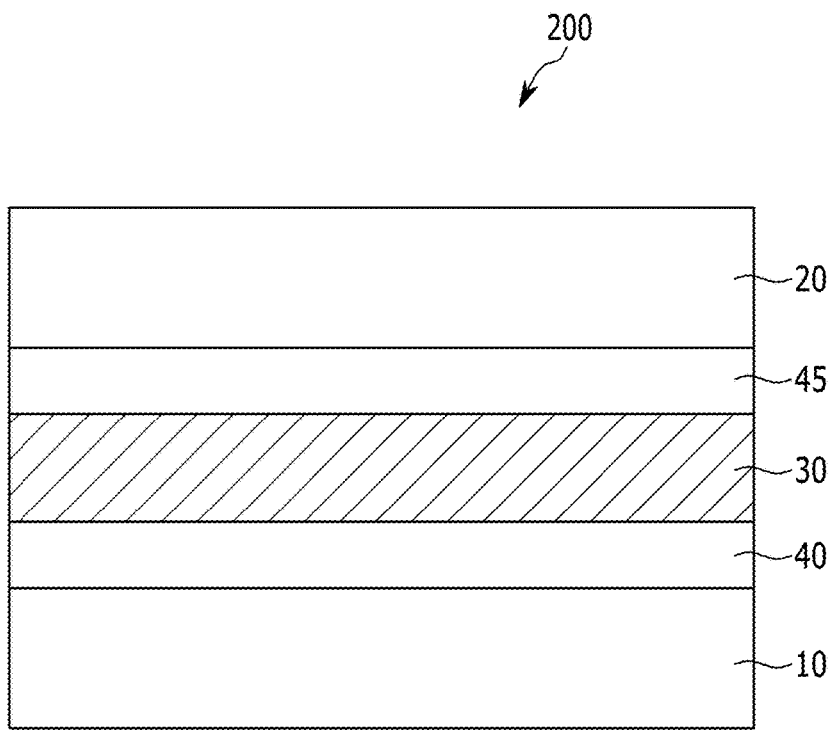
FIG. 2 is a cross-sectional view showing an organic photoelectric device according to some example embodiments.

FIG. 2 is a cross-sectional view showing an organic photoelectric device according to some example embodiments.

Referring to FIG. 2, an organic photoelectric device 200 according to the present embodiment includes a first electrode 10 and a second electrode 20 facing each other, and an active layer 30 between the first electrode 10 and the second electrode 20, like the above embodiment.

However, the organic photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
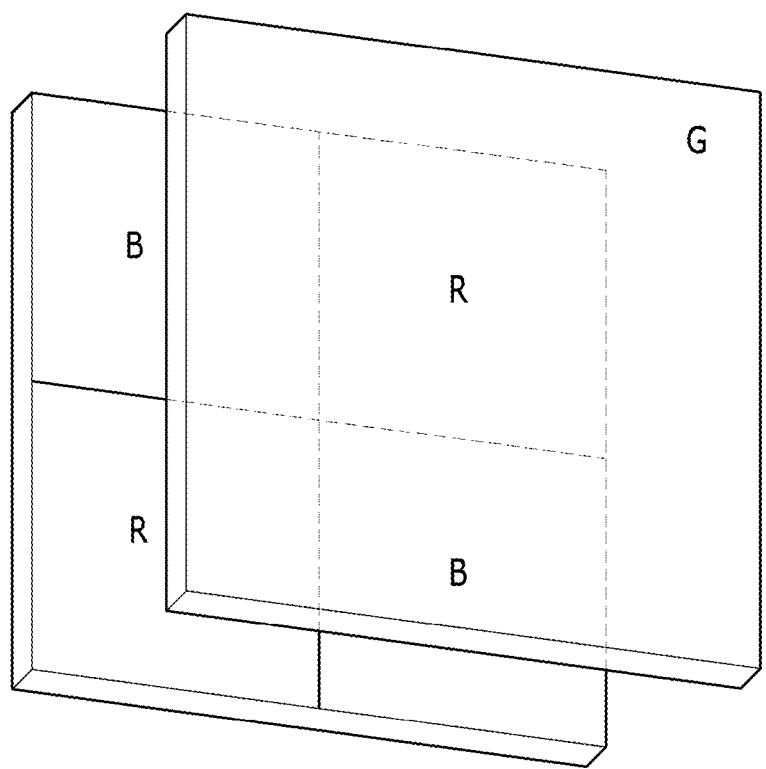
FIG. 3 is a schematic top plan view showing an organic CMOS image sensor according to some example embodiments.
Figure 4:
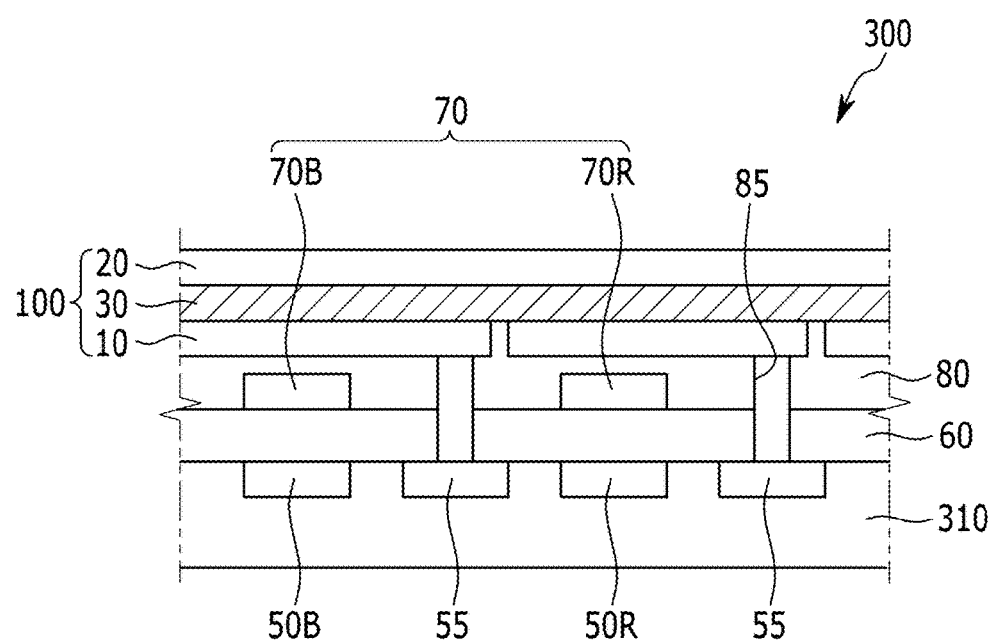
FIG. 4 is a cross-sectional view showing the organic CMOS image sensor of FIG. 3.

FIG. 3 is a schematic top plan view showing an organic CMOS image sensor according to some example embodiments, and FIG. 4 is a cross-sectional view showing the organic CMOS image sensor of FIG. 3.

Referring to FIGS. 3 and 4, an organic CMOS image sensor 300 according to some example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
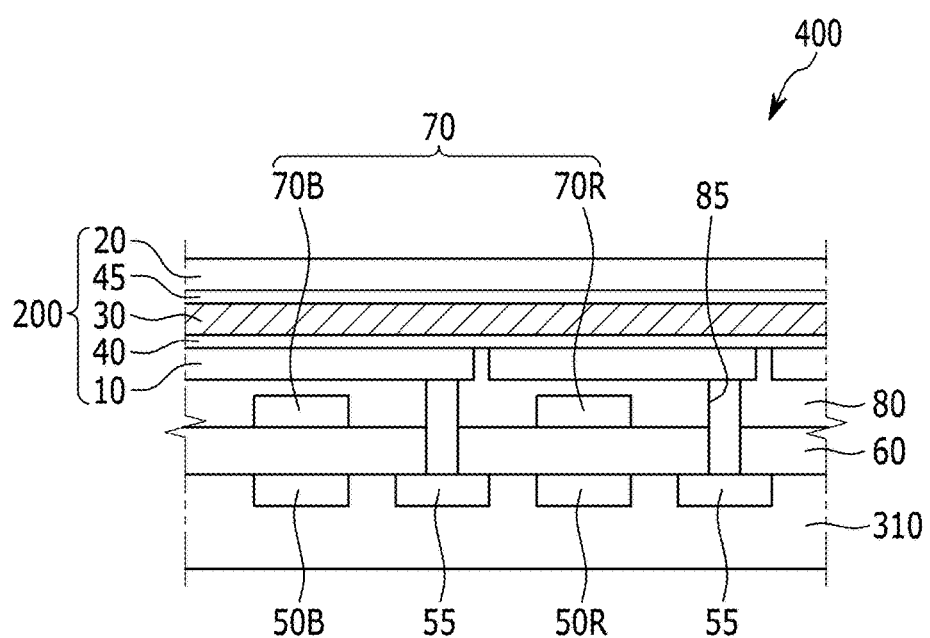
FIG. 5 is a schematic cross-sectional view showing an organic CMOS image sensor according to some example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
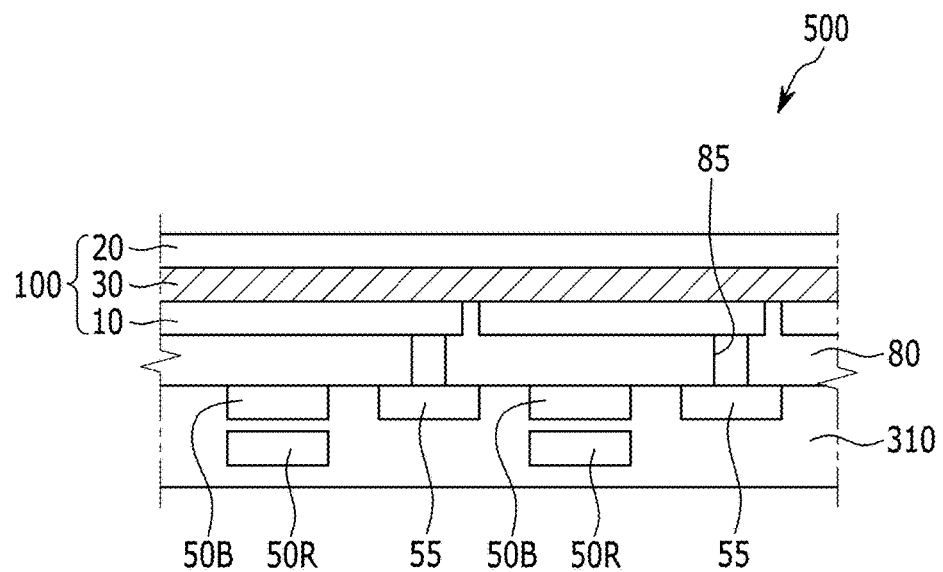
FIG. 6 is a schematic cross-sectional view showing an organic CMOS image sensor according to some example embodiments.

FIG. 6 is a cross-sectional view showing the organic CMOS image sensor according to some example embodiments.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
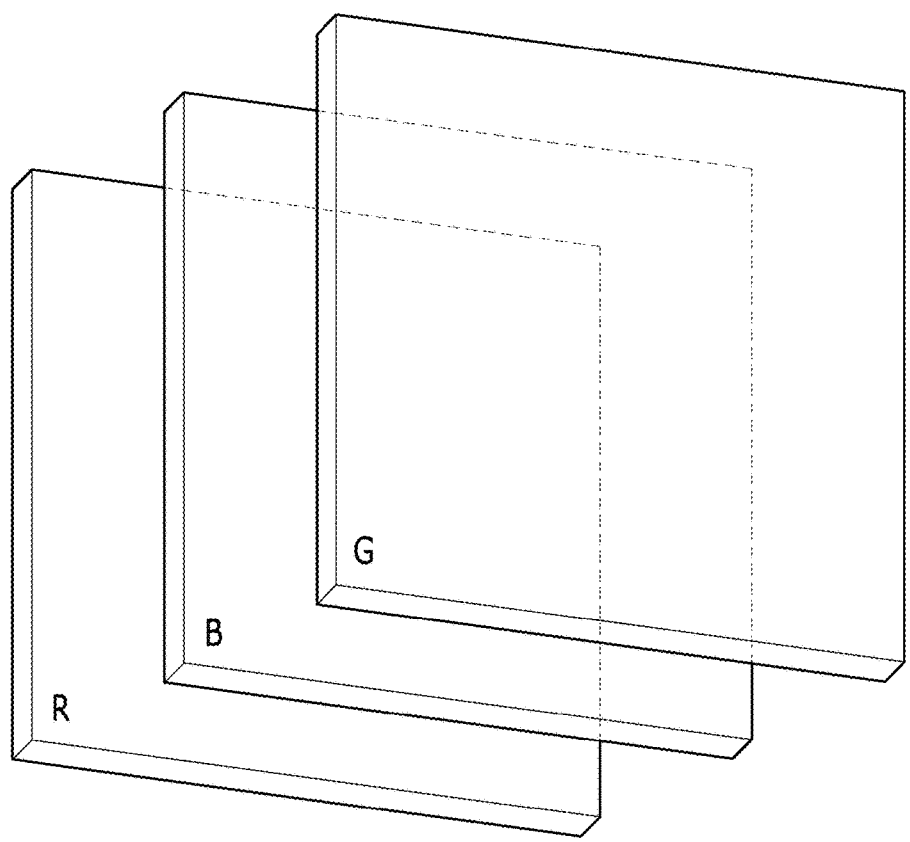
FIG. 7 is a schematic view showing an organic CMOS image sensor according to some example embodiments.

FIG. 7 is a schematic view showing an organic CMOS image sensor according to some example embodiments.

Referring to FIG. 7, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Me., USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart.

The ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2} \qquad \text{[Equation 1]}$$

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high color reproducibility at high sensitivity, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Hereinafter, the embodiments are illustrated in more detail with reference to examples. However, these examples are non-limiting, and inventive concepts are not limited thereto.

Synthesis Example 1-1: Synthesis of Compound Represented by Chemical Structure 1-1 (5-((5-(5,5-dimethylbenzo[b][1,8]naphthyridin-10(5H)-yl)selenophen-2-yl)methylene)-1,3-dimethyl-2-thioxodihydropyrimidine-4,6(1H,5H)-dione)

[Chemical Structure 1-1]

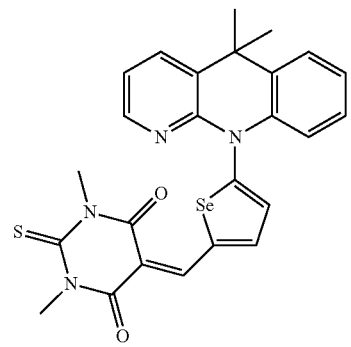

[Reaction Scheme 1-1]

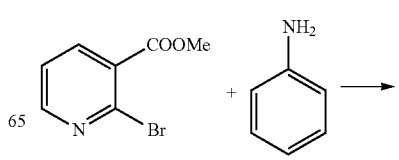

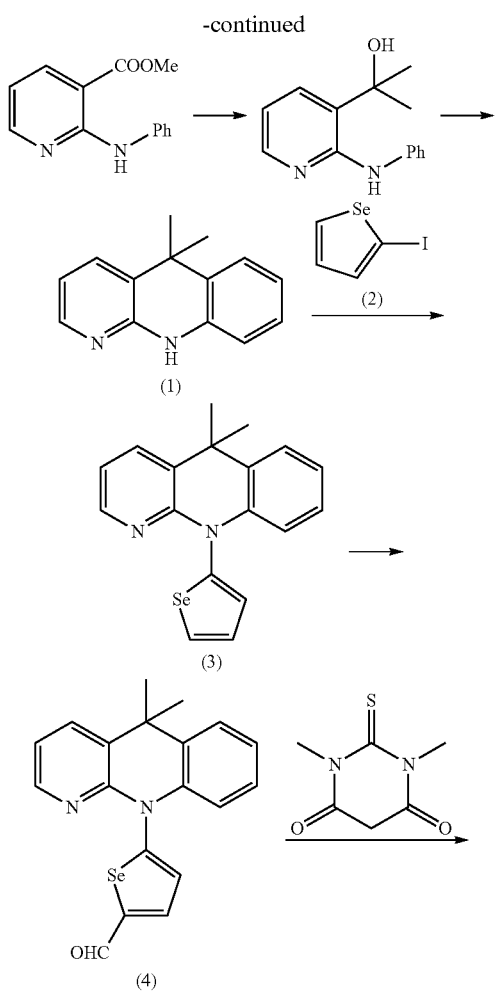

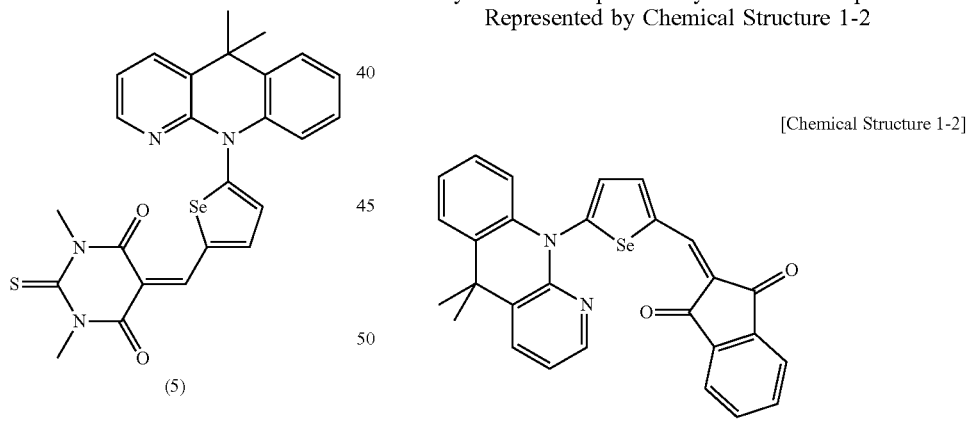

Pd(dba)$_2$, 5 mol % of P(tBu)$_3$, and 0.37 g (3.89 mmol) of NaOtBu. A product obtained therefrom was separated and purified through silica gel column chromatography (a volume ratio of toluene:hexane=1:4) to obtain 0.78 g of Compound (3) (Yield=65%).

(iv) Synthesis of Compound (4)

0.16 ml of phosphoryl chloride is added in a dropwise fashion to 0.5 ml of N,N-dimethylformamide at −15° C., and the mixture is stirred at room temperature (24° C.) for 2 hours. The resultant is slowly added in a dropwise fashion to 10 ml of dichloromethane and 0.46 g (1.54 mmol) of Compound (3) at −15° C., and the obtained mixture is stirred at room temperature for 30 minutes and concentrated under a reduced pressure. Subsequently, 5 ml of water was added thereto, a sodium hydroxide aqueous solution is added thereto until pH becomes 14, and the resulting mixture is stirred at room temperature (24° C.) for 2 hours. An organic layer extracted with ethyl acetate is washed with a sodium chloride aqueous solution and dried by adding anhydrous magnesium sulfate thereto. A product obtained therefrom is separated and purified through silica gel column chromatography (a volume ratio of hexane:dichloromethane=3:2) to obtain 0.48 g of Compound (4) (Yield: 85%).

(v) Synthesis of Compound Represented by Chemical Structure 1-1 (Compound (5))

0.40 g (1.09 mmol) of Compound (4) is suspended in ethanol, 0.23 g (1.3 mmol) of 1,3-dimethyl-2-thiobarbituric acid synthesized according to a method described in J. Pharmacol, 1944, 82, 292, p. 4417 is added thereto, and the mixture is reacted at 50° C. for 2 hours to obtain 0.51 g of a compound represented by Chemical Structure 1-1 (Yield: 95%). The compound is sublimated and purified up to purity of 99.5%.

$^1$H NMR ppm (CDCl3) 8.67 (s)-1H, 8.59 (dd)-1H, 8.18 (d)-1H, 7.81 (dd)-1H, 7.76 (m)-1H, 7.55 (m)-1H, 7.48 (d)-1H, 7.22 (m)-2H, 7.26 (m)-1H, 3.88 (s)-3H, 3.83 (s)-3H, 1.61 (s)-6H.

Synthesis Example 1-2: Synthesis of Compound Represented by Chemical Structure 1-2

[Chemical Structure 1-2]

(i) Synthesis of Compound (1)

Compound (1) is synthesized according to Reaction Scheme 1-1 in a method described in Heterocycles (2008), 75, (11), 2735-2744 and Pharmazie (1984), 39, (10), 671-2.

(ii) Synthesis of Compound (2)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(iii) Synthesis of Compound (3)

1 g (3.89 mmol) of 2-iodoselenophene and 0.74 g (3.54 mmol) of Compound (1) are heated and refluxed for 2 hours in 6 ml of anhydrous toluene under presence of 5 mol % of

[Reaction Scheme 1-2]

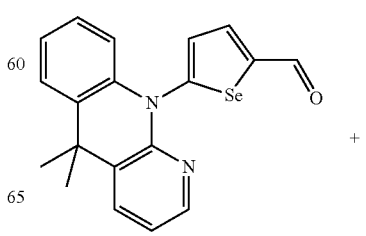

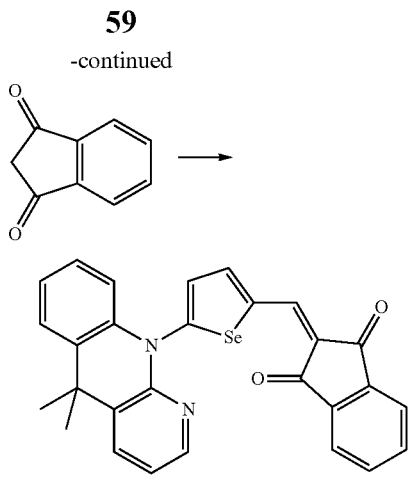

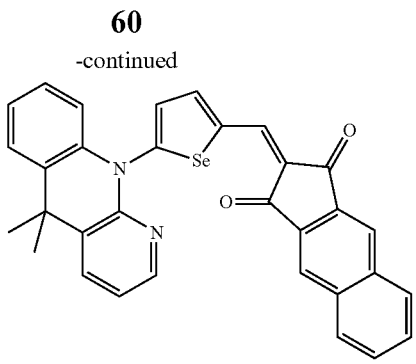

0.40 g (1.09 mmol) of Compound (4) is suspended in ethanol, 0.23 g (1.3 mmol) of 1,3-indandione is added thereto, and the mixture is reacted at 50° C. for 2 hours to obtain 0.51 g of a compound represented by Chemical Structure 1-2 (Yield: 95%).

$^1$H NMR ppm (CDCl3) 8.32 (s)-1H, 8.02 (dd)-1H, 7.72 (m)-4H, 7.37 (dd)-1H, 7.19-7.14 (m)-4H, 6.95 (m)-1H, 6.67 (t)-1H, 6.59 (s)-1H, 1.67 (s)-6H.

Synthesis Example 1-3: Synthesis of Compound Represented by Chemical Structure 1-3

[Chemical Structure 1-3]

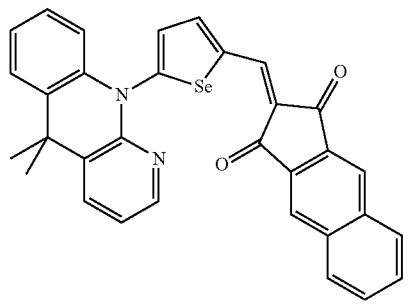

[Reaction Scheme 1-3]

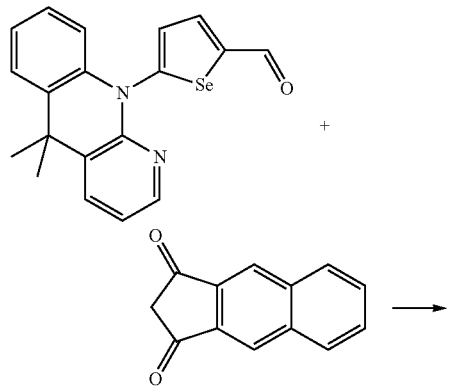

0.40 g (1.09 mmol) of Compound (4) is suspended in ethanol, 0.23 g (1.3 mmol) of 1,3-indandione is added thereto, and the mixture is reacted at 50° C. for 2 hours to obtain 0.51 g of Compound represented by Chemical Structure 1-3 (Yield: 90%).

$^1$H NMR ppm (CDCl3) 8.85 (d)-1H, 8.32 (s)-2H, 8.15 (m)-2H, 8.02 (dd)-1H, 7.76 (m)-2H, 7.37 (dd)-1H, 7.19-7.14 (m)-4H, 6.95 (m)-1H, 6.67 (t)-1H, 6.59 (s)-1H, 1.69 (s)-6H.

Synthesis Example 2-1: Synthesis of Compound Represented by Chemical Structure 2-1 (5-((5-(acridin-10(9H)-yl)selenophen-2-yl)methylene)-1,3-dimethyl-2-thioxodihydropyrimidine-4,6(1H,5H)-dione)

[Chemical Structure 2-1]

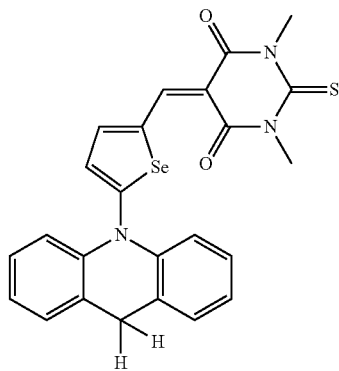

[Reaction Scheme 2-1]

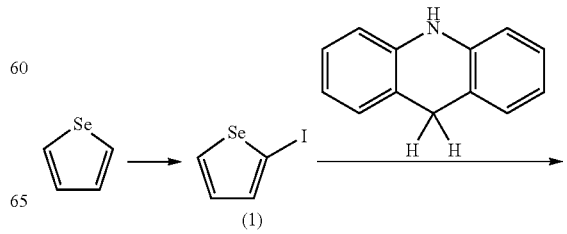

(1)

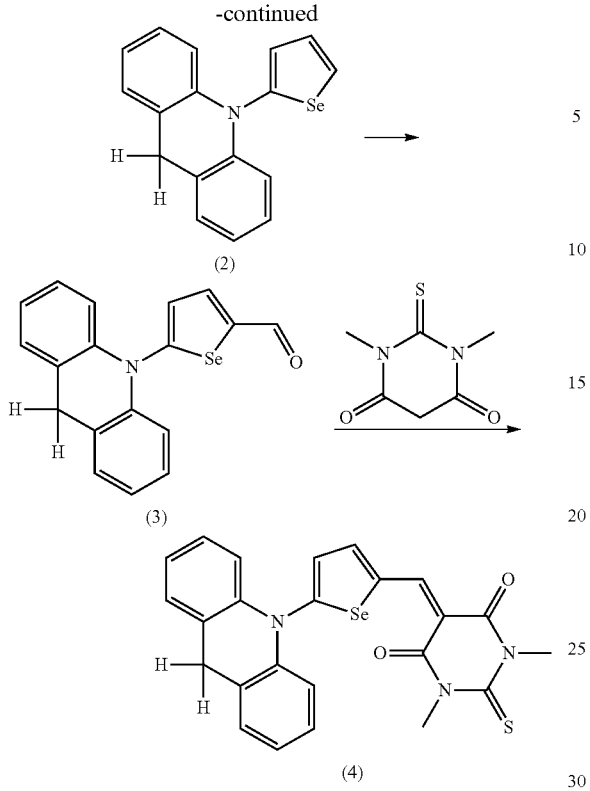

(iv) Synthesis of Compound (4) Represented by Chemical Structure 2-1

0.08 g (0.22 mmol) of Compound (3) is suspended in ethanol, 0.05 g (0.27 mmol) of 1,3-dimethyl-2-thiobarbituric acid synthesized according to J. Pharmacol., 1944, 82, 292, P. 4417 is added thereto, and the mixture is reacted at 50° C. for 2 hours to obtain 0.1 g of a compound represented by Chemical Structure 1-1 (Yield: 96%). The compound is sublimated and purified up to purity of 99.5%.

$^1$H NMR ppm (CDCl3) 8.5 (s)-1H, 7.9 (d)-1H, 7.8 (d)-2H, 7.4 (m)-6H, 7.1 (d)-1H, 3.8 (s)-2H, 3.8 (d)-6H Synthesis Example 2-2: Synthesis of Compound Represented by Chemical Structure 2-2 (2-((5-(acridin-10(9H)-yl)selenophen-2-yl)methylene)-1H-indene-1,3(2H)-dione)

[Chemical Structure 2-2]

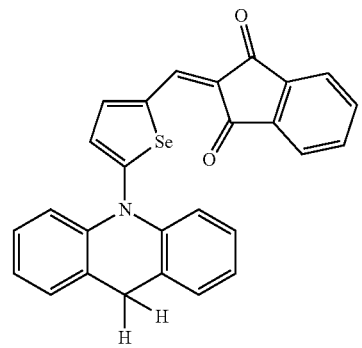

0.04 g of a compound represented by Chemical Structure 2-2 (Yield: 34%) is obtained according to the same method as Synthesis Example 2-1 except for using 1,3-indandione instead of the 1,3-dimethyl-2-thiobarbituric acid.

$^1$H NMR ppm (CDCl3) 7.9 (s)-1H, 7.8 (m)-5H, 7.7 (m)-2H, 7.4 (m)-4H, 7.3 (d)-2H, 7.0 (d)-1H, 3.9 (s)-2H Synthesis Example 2-3: Synthesis of Compound Represented by Chemical Structure 2-3 (2-((5-(acridin-10(9H)-yl)selenophen-2-yl)methylene)-1H-cyclopenta[b]naphthalene-1,3(2H)-dione)

(i) Synthesis of Compound (1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

6.78 g (26.4 mmol) of 2-iodoselenophene and 3.99 g (22 mmol) of 9,-10-dihydroacridine are heated and refluxed for 2 hours in 45 ml of anhydrous toluene under presence of 5 mol % of Pd(dba)$_2$, 5 mol % of P(tBu)$_3$, and 2.33 g (24.2 mmol) of NaOtBu. A product obtained therefrom was separated and purified through silica gel column chromatography (a volume ratio of toluene:hexane=1:4) to obtain 2.57 g of 10-(selenophen-2-yl)-9,10-dihydroacridine (Yield: 38%).

(iii) Synthesis of Compound (3)

1.0 ml of phosphoryl chloride is added in a dropwise fashion to 3.1 ml of N,N-dimethylformamide at −15° C., and the mixture is stirred at room temperature (24° C.) for 2 hours. The resultant is slowly added in a dropwise fashion to a mixture of 60 ml of dichloromethane and 2.57 g of Compound (2) at −15° C., and the obtained mixture is stirred at room temperature (24° C.) for 30 minutes and concentrated under a reduced pressure. Subsequently, 5 ml of water is added thereto, a sodium hydroxide aqueous solution is also added thereto until pH becomes 14, and the mixture is stirred at room temperature (24° C.) for 2 hours. An organic layer extracted with ethyl acetate was washed with a sodium chloride aqueous solution and dried with anhydrous magnesium sulfate. A product obtained therefrom was separated and purified through silica gel column chromatography with hexane and dichloromethane in a volume ratio of 3:2 to obtain 2.01 g of 5-(acridin-10(9H)-yl)selenophene-2-carbaldehyde (Yield: 72%).

[Chemical Structure 2-3]

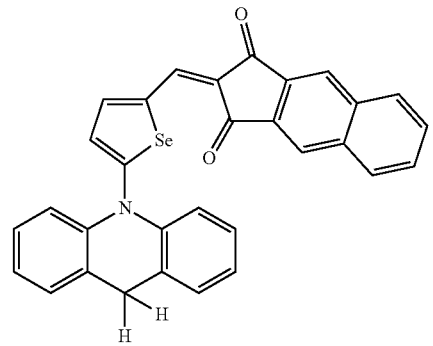

0.1 g of a compound represented by Chemical Structure 2-3 (Yield: 86%) is obtained according to the same method as Synthesis Example 2-1 except for using 2-hydrocyclopenta[b]naphthalen-1,3-dione synthesized according to Chem. Mater., Vol. 18, No. 18, 2006, p. 4261 instead of the 1,3-dimethyl-2-thiobarbituric acid.

$^1$H NMR ppm (CDCl3) 8.3 (d)-2H, 8.0 (m)-3H, 7.8 (m)-3H, 7.6 (m)-2H, 7.4 (m)-4H, 7.3 (d)-2H, 7.0 (d)-1H, 3.9 (s)-2H Synthesis Example 3-1: Synthesis of Compound Represented by Chemical Structure 3-1 (5-((5-(9,9-dimethylacridin-10(9H)-yl)selenophen-2-yl)methylene)-1,3-dimethyl-2-thioxodihydropyrimidine-4,6 (1H,5H)-dione)

[Chemical Structure 3-1]

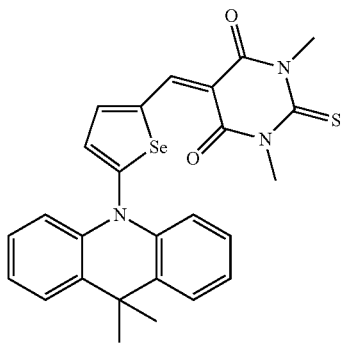

[Reaction Scheme 3-1]

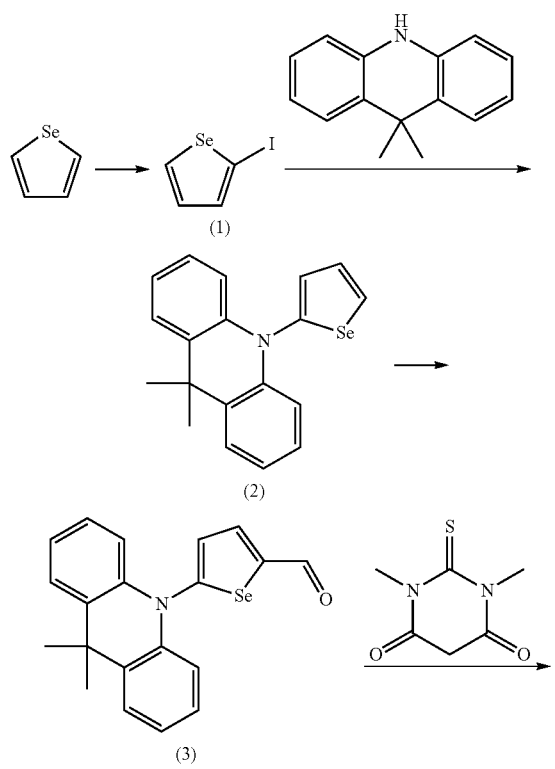

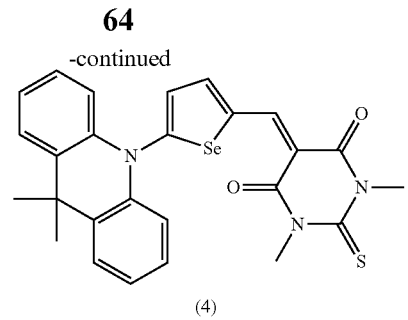

(4)

(i) Synthesis of Compound (1)

2-iodoselenophene is synthesized according to a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

4.8 g (17 mmol) of 2-iodoselenophene and 2.72 g (13 mmol) of 9,10-dihydro-9,9-dimethylacridine) are heated and refluxed for 2 hours in 25 ml of anhydrous toluene under presence of 5 mol % of Pd(dba)$_2$, 5 mol % of P(tBu)$_3$, and 1.37 g (14.3 mmol) of NaOtBu. A product obtained therefrom is separated and purified through silica gel column chromatography (a volume ratio of toluene:hexane=1:4) to obtain 2.5 g of 9,9-dimethyl-10-(selenophen-2-yl)-9,10-dihydroacridine (Yield: 57%).

(iii) Synthesis of Compound (3)

0.85 ml of phosphoryl chloride is added in a dropwise fashion to 2.64 ml of N,N-dimethylformamide at −15° C., and the mixture is stirred at room temperature (24° C.) for 2 hours. The resultant is slowly added to a mixture of 50 ml of dichloromethane and 2.40 g of Compound (2) at −15° C., and the obtained mixture is stirred at room temperature (24° C.) for 30 minutes and concentrated under a reduced pressure. Subsequently, 5 ml of water is added thereto, a sodium hydroxide aqueous solution is added thereto until pH becomes 14, and the mixture is stirred at room temperature (24° C.) for 2 hours. An organic layer extracted with ethyl acetate is washed with a sodium chloride aqueous solution and dried with anhydrous magnesium sulfate. A product obtained therefrom is separated and purified through silica gel column chromatography (a volume ratio of hexane:dichloromethane=3:2) to obtain 1.48 g of 5-(9,9-dimethylacridin-10(9H)-yl)selenophene-2-carbaldehyde) (Yield: 57%).

(iv) Synthesis of Compound (4) Represented by Chemical Structure 3-1

0.09 g (0.25 mmol) of Compound (3) is suspended in ethanol, 0.05 g (0.29 mmol) of 1,3-dimethyl-2-thiobarbituric acid synthesized in a method described in J. Pharmacol., 1944, 82, 292, p. 4417 is added thereto, and the mixture is reacted at 50° C. for 2 hours to obtain 0.1 g of a compound represented by Chemical Structure 1-1 (Yield: 99%). The compound is sublimated and purified up to purity of 99.5%.

$^1$H NMR ppm (CDCl3) 8.5 (s)-1H, 7.9 (d)-1H, 7.8 (d)-2H, 7.6 (d)-2H, 7.4 (m)-4H, 7.1 (d)-1H, 3.8 (d)-6H, 1.6 (s)-6H Synthesis Example 3-2: Synthesis of Compound Represented by Chemical Structure 3-2 (2-((5-(9,9-dimethylacridin-10(9H)-yl)selenophen-2-yl)methylene)-1H-indene-1,3(2H)-dione)

[Chemical Structure 3-2]

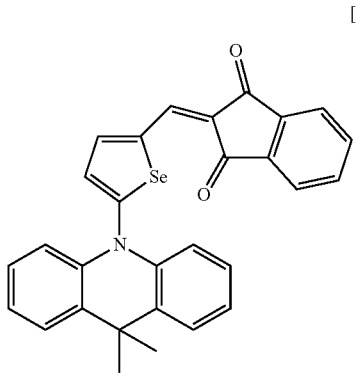

0.1 g of a compound represented by Chemical Structure 3-2 (Yield: 91%) is obtained according to the same method as the method of synthesizing the compound represented by Synthesis Example 3-1 by using 1,3-indandione instead of the 1,3-dimethyl-2-thiobarbituric acid.

$^1$H NMR ppm (CDCl3) 7.9 (s)-1H, 7.8 (m)-5H, 7.7 (m)-2H, 7.6 (d)-2H, 7.4 (m)-4H, 7.0 (d)-1H, 1.6 (s)-6H Synthesis Example 3-3: Synthesis of Compound Represented by Chemical Structure 3-3 (2-((5-(9,9-dimethylacridin-10(9H)-yl)selenophen-2-yl)methylene)-1H-cyclopenta[b]naphthalene-1,3(2H)-dione)

[Chemical Structure 3-3]

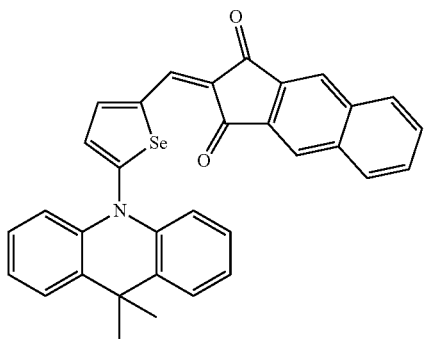

0.1 g of a compound represented by Chemical Structure 3-3 (Yield: 74%) is obtained according to the same method as used in Synthesis Example 3-1 except for using 2-hydrocyclopenta[b]naphthalen-1,3-dione synthesizing in a method described in Chem. Mater., Vol. 18, No. 18, 2006, 4261 instead of the 1,3-dimethyl-2-thiobarbituric acid.

$^1$H NMR ppm (CDCl3) 8.3 (d)-2H, 8.0 (m)-3H, 7.9 (m)-3H, 7.6 (m)-2H, 7.5 (d)-2H, 7.4 (m)-4H, 7.0 (d)-1H, 1.6 (s)-6H Synthesis Example 4-1: Synthesis of Compound Represented by Chemical Structure 4-1 (2-((5-(10H-phenoxazin-10-yl)selenophen-2-yl)methylene)-1H-indene-1,3(2H)-dione)

[Chemical Structure 4-1]

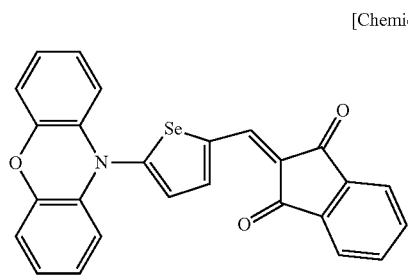

[Reaction Scheme 4-1]

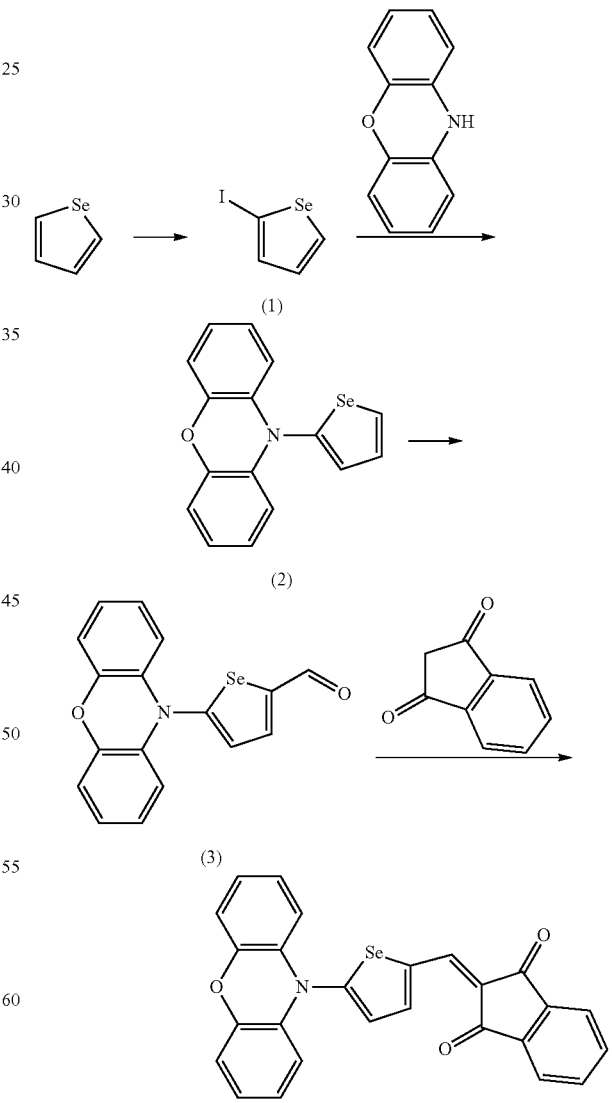

(i) Synthesis of Compound (1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

9.12 g (35.5 mmol) of 2-iodoselenophene and 5.00 g (27.3 mmol) of phenoxazine are heated and refluxed for 2 hours in 55 ml of anhydrous toluene under presence of 5 mol % of Pd(dba)$_2$, 5 mol % of P(tBu)$_3$, and 2.88 g (30.0 mmol) of NaOtBu. A product obtained therefrom is separated and purified through silica gel column chromatography (a volume ratio of toluene:hexane=1:4) to obtain 5.0 g of 10-(selenophen-2-yl)-10H-phenoxazine (Yield=59%).

(iii) Synthesis of Compound (3)

1.91 ml of phosphoryl chloride is added in a dropwise fashion to 5.97 ml of N,N-dimethylformamide at −15° C., and the mixture is stirred at room temperature (24° C.) for 2 hours. The resultant is slowly added to a mixture of 120 ml of dichloromethane and 4.99 g of Compound (2) at −15° C., and the obtained mixture is stirred at room temperature (24° C.) for 30 minutes and concentrated under a reduced pressure. Subsequently, 100 ml of water is added thereto, a sodium hydroxide aqueous solution is added thereto until pH becomes 14, and the mixture is stirred at room temperature (24° C.) for 2 hours. An organic layer extracted with ethyl acetate is washed with a sodium chloride aqueous solution and dried with anhydrous magnesium sulfate. A product obtained therefrom is separated and purified through silica gel column chromatography (a volume ratio of hexane:dichloromethane=3:2) to obtain 3.00 g of 5-(10H-phenoxazin-10-yl)selenophene-2-carbaldehyde (Yield: 55%).

(iv) Synthesis of Compound (4) Represented by Chemical Structure 4-1

1.02 g (3.00 mmol) of Compound (3) is suspended in ethanol, 0.53 g (3.60 mmol) of 1H-indene-1,3(2H)-dione is added thereto, and the mixture is reacted at 50° C. for 2 hours to obtain 0.75 g of a compound represented by Chemical Structure 4-1 (Yield: 53%). The compound is sublimated and purified up to purity of 99.5%.

$^1$H NMR ppm (CDCl3) 8.0 (s)-1H, 7.9 (m)-3H, 7.7 (dd)-2H, 7.3 (m)-2H, 7.1-7.0 (m)-7H Synthesis Example 4-2: Synthesis of Compound Represented by Chemical Structure 4-2 (2-((5-(10H-phenoxazin-10-yl)selenophen-2-yl)methylene)-1H-cyclopenta[b]naphthalene-1,3(2H)-dione)

[Chemical Structure 4-2]

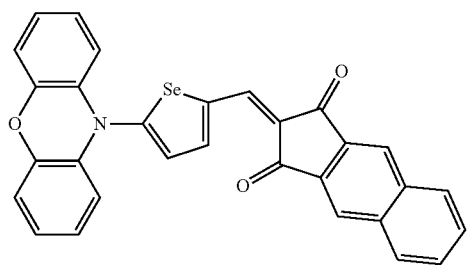

A compound represented by Chemical Structure 4-2 (Yield: 62%) is obtained according to the same method as used in Synthesis Example 4-1 except for using 1H-cyclopenta[b]naphthalene-1,3(2H)-dione instead of 1H-indene-1,3(2H)-dione in (iv) of Synthesis Example 4-1.

$^1$H NMR ppm (CDCl3) 8.5 (d)-2H, 8.3 (s)-1H, 7.6 (dd)-2H, 8.0 (m)-2H, 7.1-6.8 (m)-7H, 6.6 (m)-3H Synthesis Example 4-3: Synthesis of Compound Represented by Chemical Structure 4-3 (5-((5-(10H-phenoxazin-10-yl)selenophen-2-yl)methylene)-1,3-dimethyl-2-thioxodihydropyrimidine-4,6(1H,5H)-dione)

[Chemical Structure 4-3]

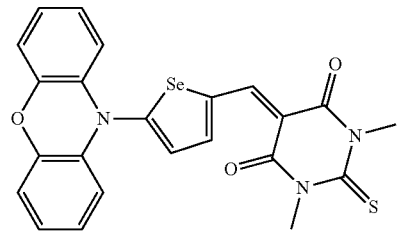

A compound represented by Chemical Structure 4-3 (Yield: 70%) is obtained according to the same method as used in Synthesis Example 4-1 except for using 1,3-dimethyl-2-thiobarbituric acid synthesized in a method described in J. Pharmacol., 1944, 82, 292, p. 4417 instead of the 1H-indene-1,3(2H)-dione in (iv) of Synthesis Example 4-1.

$^1$H NMR ppm (CDCl3) 7.9 (s)-1H, 7.1 (s)-1H, 6.9-6.8 (m)-6H, 6.6 (m)-3H, 6.4 (d)-1H, 3.3 (m)-6H Synthesis Example 4-4: Synthesis of Compound Represented by Chemical Structure 4-4 (5-((5-(10H-phenoxazin-10-yl)selenophen-2-yl)methylene)-1,3-dimethylpyrimidine-2,4,6(1H,3H,5H)-trione)

[Chemical Structure 4-4]

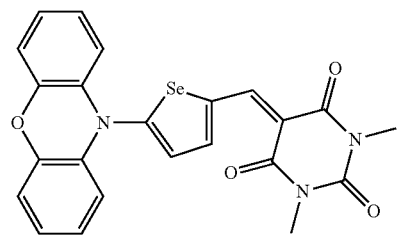

A compound represented by Chemical Structure 4-4 (Yield: 68%) is obtained according to the same method as used in Synthesis Example 4-1 except for using 1,3-dimethyl barbituric acid instead of 1H-indene-1,3(2H)-dione in (iv) of Synthesis Example 4-1.

$^1$H NMR ppm (CDCl3) 7.9 (s)-1H, 7.1 (s)-1H, 6.9-6.8 (m)-6H, 6.6 (m)-3H, 3.2 (m)-6H

Synthesis Example 5-1: Synthesis of Compound Represented by Chemical Structure 5-1 (2-((5-(10H-phenothiazin-10-yl)selenophen-2-yl)methylene)-1H-cyclopenta[b]naphthalene-1,3(2H)-dione)

[Chemical Structure 5-1]

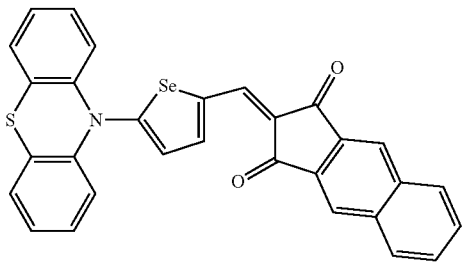

[Reaction Scheme 5-1]

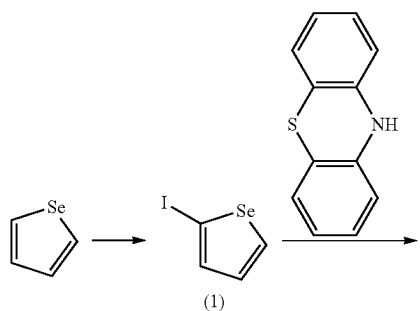

(1)

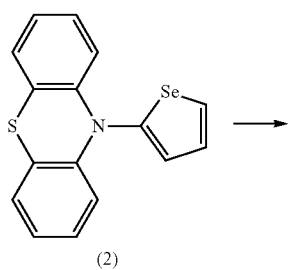

(2)

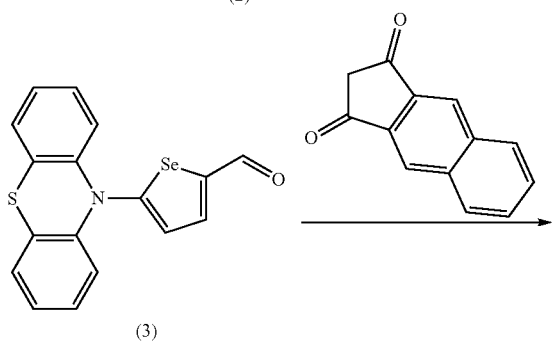

(3)

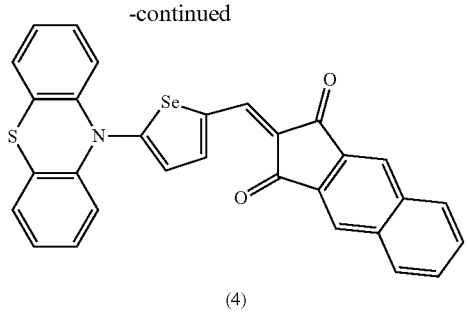

(4)

(i) Synthesis of Compound (1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

4.25 g (16.6 mmol) of 2-iodoselenophene and 3 g (15.1 mmol) of phenothiazine are heated and refluxed for 2 hours in 30 ml of anhydrous toluene under presence of 5 mol % of Pd(dba)$_2$, 5 mol % of P(tBu)$_3$, and 1.6 g (16.6 mmol) of NaOtBu. A product obtained therefrom is separated and purified through silica gel column chromatography (a volume ratio of toluene:hexane=1:4) to obtain 1.7 g of 10-(selenophen-2-yl)-10H-phenothiazine (Yield: 34%).

(iii) Synthesis of Compound (3)

0.16 ml of phosphoryl chloride is added in a dropwise fashion to 0.5 ml of N,N-dimethylformamide at −15° C., and the mixture is stirred at room temperature (24° C.) for 2 hours. The resultant is slowly added in a dropwise fashion to a mixture of 10 ml of dichloromethane and 0.4 g of Compound (2) at −15° C., and the obtained mixture is stirred at room temperature (24° C.) for 30 minutes and concentrated under a reduced pressure. Subsequently, 5 ml of water is added thereto, a sodium hydroxide aqueous solution is added thereto until pH becomes 14, and the mixture is stirred at room temperature (24° C.) for 2 hours. An organic layer extracted with ethyl acetate is washed with a sodium chloride aqueous solution and dried with anhydrous magnesium sulfate. A product obtained therefrom is separated and purified through silica gel column chromatography (a volume ratio of hexane:dichloromethane=3:2) to obtain 0.56 g of 5-(10H-phenothiazin-10-yl)selenophene-2-carbaldehyde) (Yield: 77%).

(iv) Synthesis of Compound (4) Represented by Chemical Structure 1-1

0.1 g (0.28 mmol) of Compound (3) is suspended in ethanol, 0.06 g (0.34 mmol) of 1H-cyclopenta[b]naphthalene-1,3(2H)-dione is added thereto, and the mixture is reacted at 50° C. for 2 hours to obtain 0.1 g of a compound represented by Chemical Structure 1-1 (Yield: 72%). The compound is sublimated and purified up to purity of 99.5%.

$^1$H NMR ppm (CDCl3) 8.4 (d)-2H, 7.9 (s)-1H, 7.7 (m)-2H, 7.3 (m)-2H, 7.2 (dd)-2H, 7.1 (dd)-2H, 7.0 (m)-2H, 6.9 (m)-2H, 6.7 (d)-1H, 6.1 (s)-1H

Synthesis Example 5-2: Synthesis of Compound Represented by Chemical Structure 5-2 (2-((5-(10H-phenothiazin-10-yl)selenophen-2-yl)methylene)-1H-indene-1,3(2H)-dione)

[Chemical Structure 5-2]

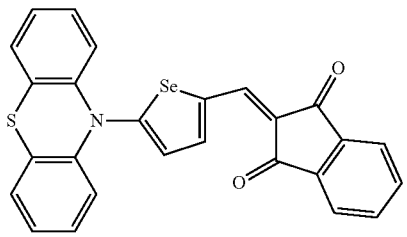

A compound represented by Chemical Structure 5-2 (Yield: 62%) is obtained according to the same method as used in Synthesis Example 5-1 except for using 1H-indene-1,3(2H)-dione instead of the 1H-cyclopenta[b]naphthalene-1,3(2H)-dione in (iv) of Synthesis Example 5-1.

$^1$H NMR ppm (CDCl3) 8.0 (s)-1H, 7.4 (m)-4H, 7.3 (dd)-2H, 7.2 (dd)-2H, 7.1 (m)-2H, 7.0 (m)-2H, 6.7 (d)-1H, 6.1 (s)-1H Synthesis Example 5-3: Synthesis of Compound Represented by Chemical Structure 5-3 (5-((5-(10H-phenothiazin-10-yl)selenophen-2-yl)methylene)-1,3-dimethyl-2-thioxodihydropyrimidine-4,6(1H,5H)-dione)

[Chemical Structure 5-3]

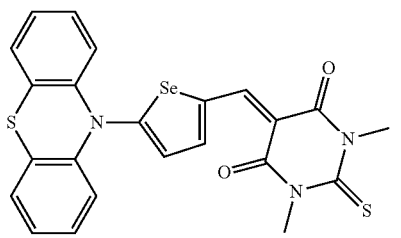

A compound represented by Chemical Structure 5-3 (Yield: 70%) is obtained according to the same method as used in Synthesis Example 5-1 except for using 1,3-dimethyl-2-thiobarbituric acid synthesized in a method described in J. Pharmacol., 1944, 82, 292, p. 4417 instead of the 1H-cyclopenta[b]naphthalene-1,3(2H)-dione in (iv) of Synthesis Example 5-1.

$^1$H NMR ppm (CDCl3) 7.6 (s)-1H, 7.4 (dd)-2H, 7.3 (dd)-2H, 7.2 (dd)-2H, 7.1 (m)-2H, 6.9 (d)-1H, 6.4 (d)-1H, 3.3 (m)-6H

Synthesis Example 5-4: Synthesis of Compound Represented by Chemical Structure Ia 5-4 (5-((5-(10H-phenothiazin-10-yl)selenophen-2-yl)methylene)-1,3-dimethylpyrimidine-2,4,6(1H,3H,5H)-trione)

[Chemical Structure 5-4]

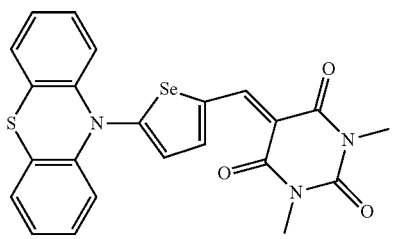

A compound represented by Chemical Structure 5-4 (Yield: 68%) is obtained according to the same method as used in Synthesis Example 5-1 except for using 1,3-dimethyl barbituric acid instead of the 1H-cyclopenta[b]naphthalene-1,3(2H)-dione in (iv) of Synthesis Example 5-1.

$^1$H NMR ppm (CDCl3) 7.6 (s)-1H, 7.4 (dd)-2H, 7.3 (dd)-2H, 7.2 (dd)-2H, 7.1 (m)-2H, 6.9 (d)-1H, 6.4 (d)-1H, 3.2 (m)-6H

Synthesis Example 6-1: Synthesis of Compound Represented by Chemical Structure 6-1

[Chemical Structure 6-1]

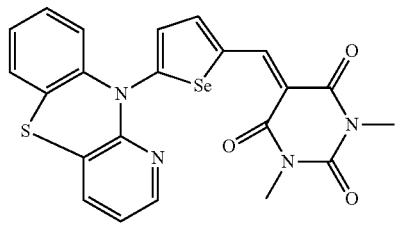

A compound represented by Chemical Structure 6-1 (Yield: 68%) is obtained according to the same method as used in Synthesis Example 5-4 except for using 1,3-dimethyl-2-barbituric acid instead of the 1,3-dimethyl-2-thiobarbituric acid as the final reaction compound.

1H NMR ppm (CDCl3) 7.6 (s)-1H, 7.4 (dd)-2H, 7.3 (dd)-2H, 7.2 (dd)-2H, 7.1 (m)-2H, 6.9 (d)-1H, 6.3 (d)-1H, 3.4 (m)-6H

Synthesis Example 7-1: Synthesis of Compound Represented by Chemical Structure 7-1 (2-((5-(10H-phenoselenazin-10-yl)selenophen-2-yl)methylene)-1H-cyclopenta[b]naphthalene-1,3(2H)-dione)

[Chemical Structure 7-1]

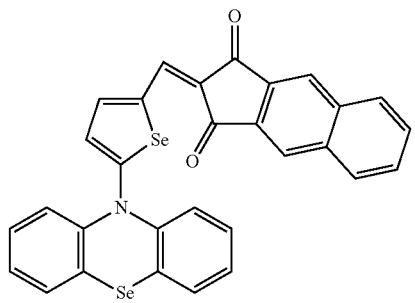

[Reaction Scheme 7-1]

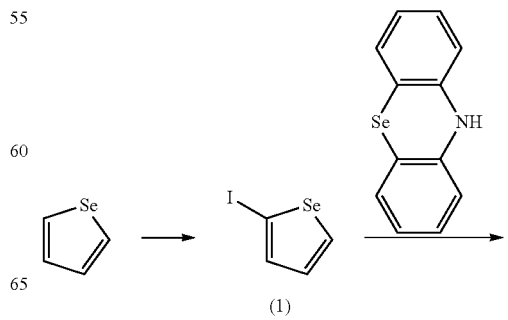

(1)

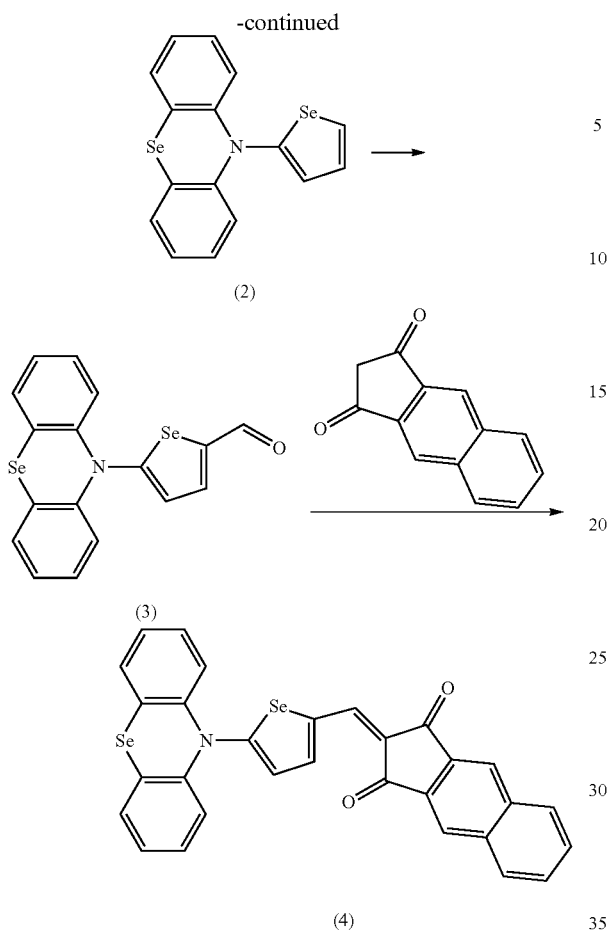

(i) Synthesis of Compound (1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

13.6 g (52.8 mmol) of 2-iodoselenophene and 10.0 g (40.6 mmol) of 10H-phenoselenazine are heated and refluxed for 2 hours in 100 ml of anhydrous toluene under presence of 5 mol % of Pd(dba)$_2$, 5 mol % of P(tBu)$_3$, and 4.29 g (44.7 mmol) of NaOtBu. A product obtained therefrom is separated and purified through silica gel column chromatography (a volume ratio of toluene:hexane=1:4) to obtain 6.89 g of 10-(selenophen-2-yl)-10H-phenoselenazine (Yield: 45.2%).

(iii) Synthesis of Compound (3)

2.2 ml of phosphoryl chloride is added in a dropwise fashion in 6.8 ml of N,N-dimethylformamide at −15° C., and the mixture is stirred at room temperature (24° C.) for 2 hours. The resultant is slowly added in a dropwise fashion to a mixture of 180 ml of dichloromethane and 6.84 g of Compound (2) at −15° C., and the mixture is stirred at room temperature for 30 minutes and concentrated under a reduced pressure. Subsequently, 100 ml of water is added thereto, a sodium hydroxide aqueous solution is added thereto until pH becomes 14, and the obtained mixture is stirred at room temperature (24° C.) for 2 hours. An organic layer extracted with ethyl acetate is washed with a sodium chloride aqueous solution and dried with anhydrous magnesium sulfate. A product obtained therefrom is separated and purified through silica gel column chromatography (a volume ratio of hexane:dichloromethane=3:2) to obtain 5.16 g of 5-(10H-phenoselenazin-10-yl)selenophene-2-carbaldehyde (Yield: 70.4%).

(iv) Synthesis of Compound (4) Represented by Chemical Structure 7-1

2.00 g (4.96 mmol) of Compound (3) is suspended in ethanol, 1.46 g (7.44 mmol) of 1H-cyclopenta[b]naphthalene-1,3(2H)-dione is added thereto, and the mixture is reacted at 50° C. for 2 hours to obtain 2.62 g of a compound represented by Chemical Structure 7-1 (Yield: 72.4%). The compound is sublimated and purified up to purity of 99.8%.

$^1$H NMR ppm (DMSO) 8.34 (s)-1H, 8.32 (s)-1H, 8.27 (s)-1H, 8.24-8.16 (m)-3H, 7.98 (dd)-2H, 7.88 (dd)-2H, 7.71 (m)2H, 7.61 (t)-2H, 7.45 (t)-2H, 6.61 (d)-1H Synthesis Example 7-2: Synthesis of Compound Represented by Chemical Structure 7-2 (2-((5-(10H-phenoselenazin-10-yl)selenophen-2-yl)methylene)-1H-indene-1,3(2H)-dione)

[Chemical Structure 7-2]

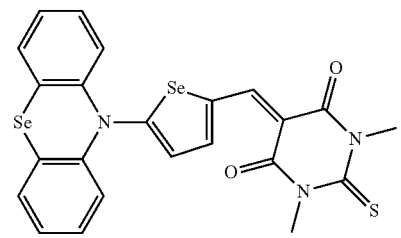

A compound represented by Chemical Structure 7-2 (Yield: 98.6%) is obtained according to the same method as used in Synthesis Example 7-1 except for using 1,3-dimethyl-2-thiobarbituric acid synthesized in a method described in J. Pharmacol., 1944, 82, 292, p. 4417 instead of the 1H-cyclopenta[b]naphthalene-1,3(2H)-dione in (iv).

$^1$H NMR ppm (DMSO) 8.44 (d)-1H, 8.30 (m)-1H, 7.97 (d)-2H, 7.89 (d)-2H, 7.60 (t)-2H, 7.43 (t)-2H, 6.70 (m)-1H, 3.59 (m)-6H Synthesis Example 8-1: Synthesis of Compound Represented by Chemical Structure 8-1

[Chemical Structure 8-1]

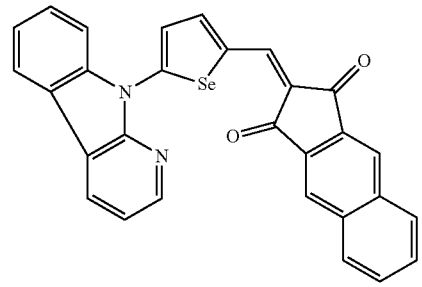

[Reaction Scheme 8-1]

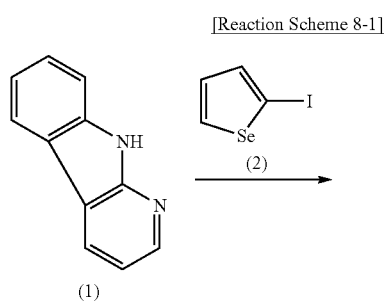

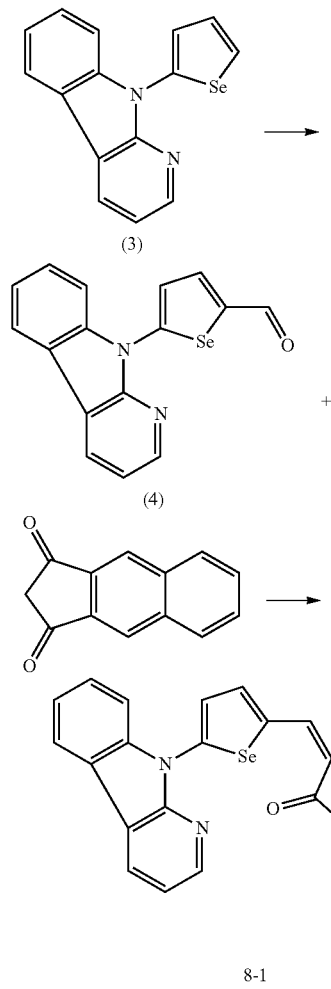

(i) Synthesis of Compound (3)

1 g (3.89 mmol) of 2-iodoselenophene synthesized in Synthesis Example 1-1 (Compound (2)) and 0.60 g (3.54 mmol) of 9H-pyrido[2,3-b]indole (Compound (1)) are heated and refluxed for 2 hours in 6 ml of anhydrous toluene under presence of 5 mol % of Pd(dba)$_2$, 5 mol % of P(tBu)$_3$, and 0.37 g (3.89 mmol) of NaOtBu. A product obtained therefrom is separated and purified through silica gel column chromatography (a volume ratio of toluene:hexane=1:4) to obtain 0.68 g of Compound (3) (Yield: 65%).

(ii) Synthesis of Compound (4)

0.48 g of Compound (4) (Yield: 85%) is obtained according to the same method as in (iv) of Synthesis Example 1-1.

(iii) Synthesis of Compound (5) Represented by Chemical Structure 8-1

0.35 g (1.09 mmol) of Compound (4) is suspended in ethanol, 0.26 g (1.3 mmol) of 1H-cyclopenta[b]naphthalene-1,3(2H)-dione is added thereto, and the mixture is reacted at 50° C. for 2 hours to obtain 0.52 g of a compound represented by Chemical Structure 1-3 (Yield: 95%).

$^1$H NMR ppm (CDCl3) 8.85 (s)-2H, 8.55-8.51 (m)-2H, 8.39-8.32 (d)-2H, 8.15-8.11 (m)-3H, 7.76 (m)-2H, 7.36 (m)-1H, 7.17-7.10 (m)-4H Synthesis Example 8-2: Synthesis of Compound Represented by Chemical Structure 8-2

[Chemical Structure 8-2]

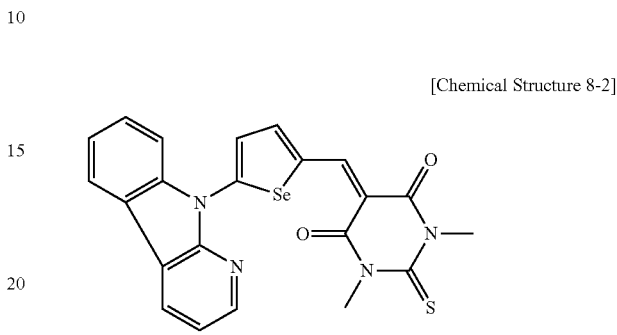

A compound represented by Chemical Structure 8-2 is synthesized in the same synthesis method as used in Synthesis Example 8-1 except for using 1,3-dimethyl-2-thiobarbituric acid instead of the 1H-cyclopenta[b]naphthalene-1,3(2H)-dione as the final reaction compound.

$^1$H NMR ppm (CDCl3) 8.55-8.51 (m)-2H, 8.39 (d)-2H, 8.11 (d)-1H, 7.87 (s)-1H, 7.16-7.10 (m)-4H, 3.52 (s)-6H Comparative Synthesis Example 1: Synthesis of Compound Represented by Chemical Structure 9-1

[Chemical Structure 9-1]

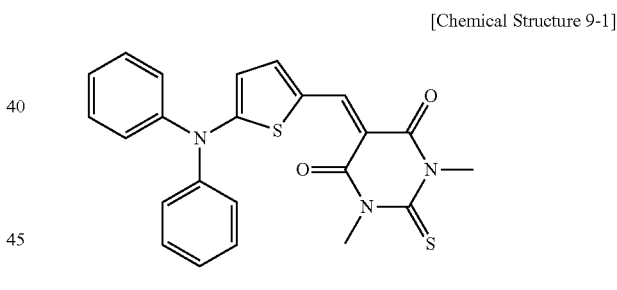

[Reaction Scheme 9-1]

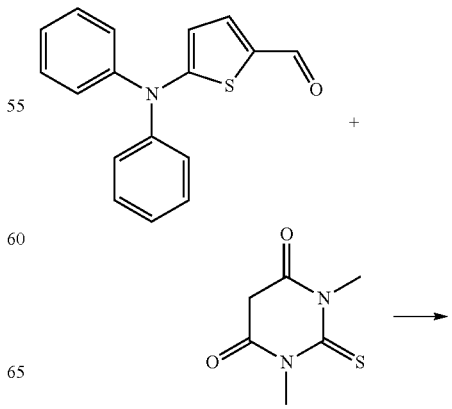

-continued

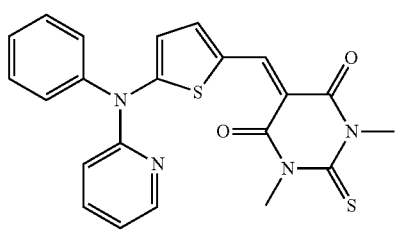

5-(diphenylamino)thiophene-2-carbaldehyde is synthesized in a method described in Dalton Transactions, 443, 1473-1482; 2015 and then, condensation-reacted with 1,3-dimethyl barbituric acid to obtain a compound according to Comparative Synthesis Example 1.

$^1$H NMR ppm (CDCl3) 8.4 (s)-1H, 7.8 (d)-1H, 7.5-7.3 (m)-10H, 6.5 (d)-1H, 3.7 (d)-6H Reference Synthesis Example 1: Synthesis of Compound Represented by Chemical Structure 10-1

[Chemical Structure 10-1]

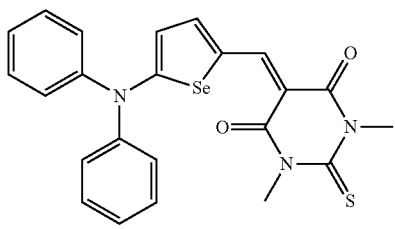

[Reaction Scheme 10-1]

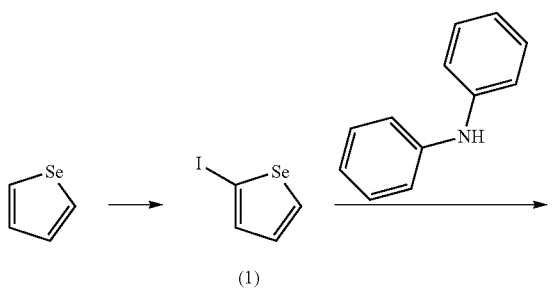

(1)

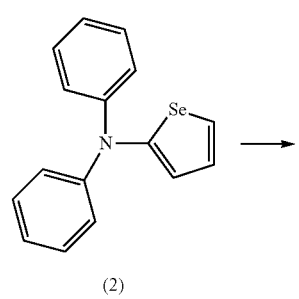

(2)

-continued

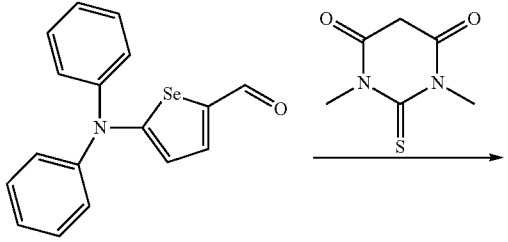

(3)

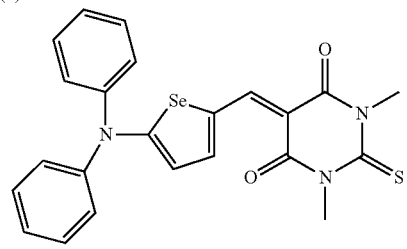

(4)

(i) Synthesis of Compound (3)

1 g (3.89 mmol) of 2-iodoselenophene (Compound (1)) and 0.60 g (3.54 mmol) of diphenylamine are heated and refluxed in 6 ml of anhydrous toluene under presence of 5 mol % of Pd(dba)$_2$, 5 mol % of P(tBu)$_3$, and 0.37 g (3.89 mmol) of NaOtBu for 2 hours. A product obtained therefrom is separated and purified through silica gel column chromatography (a volume ratio of toluene:hexane=1:4) to obtain 0.69 g of Compound (3) (Yield: 65%).

(ii) Synthesis of Compound (4) Represented by Chemical Structure 10-1

0.33 g (1.09 mmol) of Compound (3) is suspended in ethanol, 0.23 g (1.3 mmol) of 1,3-dimethyl-2-thiobarbituric acid synthesized in a method described in J. Pharmacol., 1944, 82, 292, p. 4417 is added thereto, and the mixture is reacted at 50° C. for 2 hours to obtain 0.47 g of a compound represented by Chemical Structure 10-1 (Yield: 90%).

$^1$H NMR ppm (CDCl3) 8.5 (s)-1H, 7.9 (d)-1H, 7.5-7.3 (m)-10H, 6.6 (d)-1H, 3.8 (d)-6H Light Absorption Characteristics of Compounds of Synthesis Examples 1-1 to 8-2, Comparative Synthesis Example 1, and Reference Synthesis Example 1

Light absorption characteristics (an absorption wavelength, absorption intensity, and a full width at half maximum (FWHM)) of the compounds according to Synthesis Examples 1-1 to 8-2, Comparative Synthesis Example 1, and Reference Synthesis Example 1 depending on a wavelength are evaluated.

5 mg of each compound according to Synthesis Examples 1-1 to 8-2, Comparative Synthesis Example 1, and Reference Synthesis Example 1 is dissolved in 250 ml of toluene and then, 10 times diluted. The results are shown in Table 1.

Thermal Stability of Compounds of Synthesis Examples 1-1 to 8-2, Comparative Synthesis Example 1, and Reference Synthesis Example 1

Thermal stability of the compounds according to Synthesis Examples 1-1 to 8-2, Comparative Synthesis Example 1, and Reference Synthesis Example 1 is evaluated by measuring a 10 wt % loss temperature (Ts, a deposition temperature) at 10 Pa. The loss temperature is measured in a thermal gravimetric analysis (TGA) method. The results are shown in Table 1.

TABLE 1

| | Chemical Structure Nos. | Solution $\lambda_{max}$ (nm) | FWHM (nm) | Tm (°C.) | Ts (10 wt %, 10 Pa) (°C.) | T (Tm − Ts) (°C.) | Morphology changes after treating thin films at 160° C. For 3 hr |
|---|---|---|---|---|---|---|---|
| Synthesis Example 1-1 | Chemical Structure 1-1 | 524 | 33 | 310 | 243 | 67 | No crystallization |
| Synthesis Example 1-2 | Chemical Structure 1-2 | 519 | 40 | 297 | 223 | 74 | No crystallization |
| Synthesis Example 2-1 | Chemical Structure 2-1 | 527 | 38 | 278 | 238 | 40 | No crystallization |
| Synthesis Example 2-2 | Chemical Structure 2-2 | 525 | 43 | 270 | 217 | 53 | No crystallization |
| Synthesis Example 2-3 | Chemical Structure 2-3 | 550 | 42 | 277 | 255 | 22 | No crystallization |
| Synthesis Example 3-1 | Chemical Structure 3-1 | 527 | 39 | 329 | 237 | 92 | No crystallization |
| Synthesis Example 3-2 | Chemical Structure 3-2 | 525 | 41 | 299 | 216 | 83 | No crystallization |
| Synthesis Example 3-3 | Chemical Structure 3-3 | 550 | 36 | 309 | 255 | 54 | No crystallization |
| Synthesis Example 4-1 | Chemical Structure 4-1 | 522 | 60 | 272 | 203 | 69 | No crystallization |
| Synthesis Example 4-2 | Chemical Structure 4-2 | 547 | 58 | 273 | 244 | 29 | No crystallization |
| Synthesis Example 4-3 | Chemical Structure 4-3 | 527 | 49 | 300 | 228 | 72 | No crystallization |
| Synthesis Example 4-4 | Chemical Structure 4-4 | 500 | 53 | 307 | 217 | 90 | No crystallization |
| Synthesis Example 5-1 | Chemical Structure 5-1 | 542 | 45 | 330 | 265 | 65 | No crystallization |
| Synthesis Example 5-2 | Chemical Structure 5-2 | 517 | 48 | 306 | 233 | 73 | No crystallization |
| Synthesis Example 5-3 | Chemical Structure 5-3 | 520 | 42 | 322 | 235 | 87 | No crystallization |
| Synthesis Example 8-1 | Chemical Structure 8-1 | 517 | 56 | 330 | 274 | 56 | No crystallization |
| Synthesis Example 8-2 | Chemical Structure 8-2 | 505 | 40 | 356 | 256 | 100 | No crystallization |
| Synthesis Example 7-2 | Chemical Structure 7-2 | 517 | 39 | 301 | 242 | 59 | No crystallization |
| Synthesis Example 7-1 | Chemical Structure 7-1 | 540 | 43 | 349 | 276 | 73 | No crystallization |
| Synthesis Example 6-1 | Chemical Structure 6-1 | 513 | 43 | 334 | 230 | 104 | No crystallization |
| Comparative Synthesis Example 1 | Chemical Structure 9-1 | 522 | 48 | 275 | 238 | 37 | crystallization |
| Reference Synthesis Example 1 | Chemical Structure 10-1 | 524 | 46 | 308 | 232 | 76 | crystallization |

Referring to Table 1, the compounds of Synthesis Examples 1-1 to 8-2 show a maximum absorption wavelength in a green wavelength region (e.g., 500 nm to 550 nm) and a narrower full width at half maximum (FWHM). Accordingly, the compounds according to Synthesis Examples 1-1 to 8-2 show excellent green wavelength selectivity.

In addition, when a compound has a lower melting point than a deposition temperature during the vacuum deposition, the compound may be decomposed and simultaneously gasified and thus fails in being formed into a film. Accordingly, the melting point of a compound should be higher than the deposition temperature. The compounds according to Synthesis Examples 1-1 to 8-2 may have greater than or equal to 22° C. higher melting point than the deposition temperature. Therefore, the compounds according to Synthesis Examples 1-1 to 8-2 have a high difference between melting point and deposition temperature and thus may secure process stability.

Figure 8:
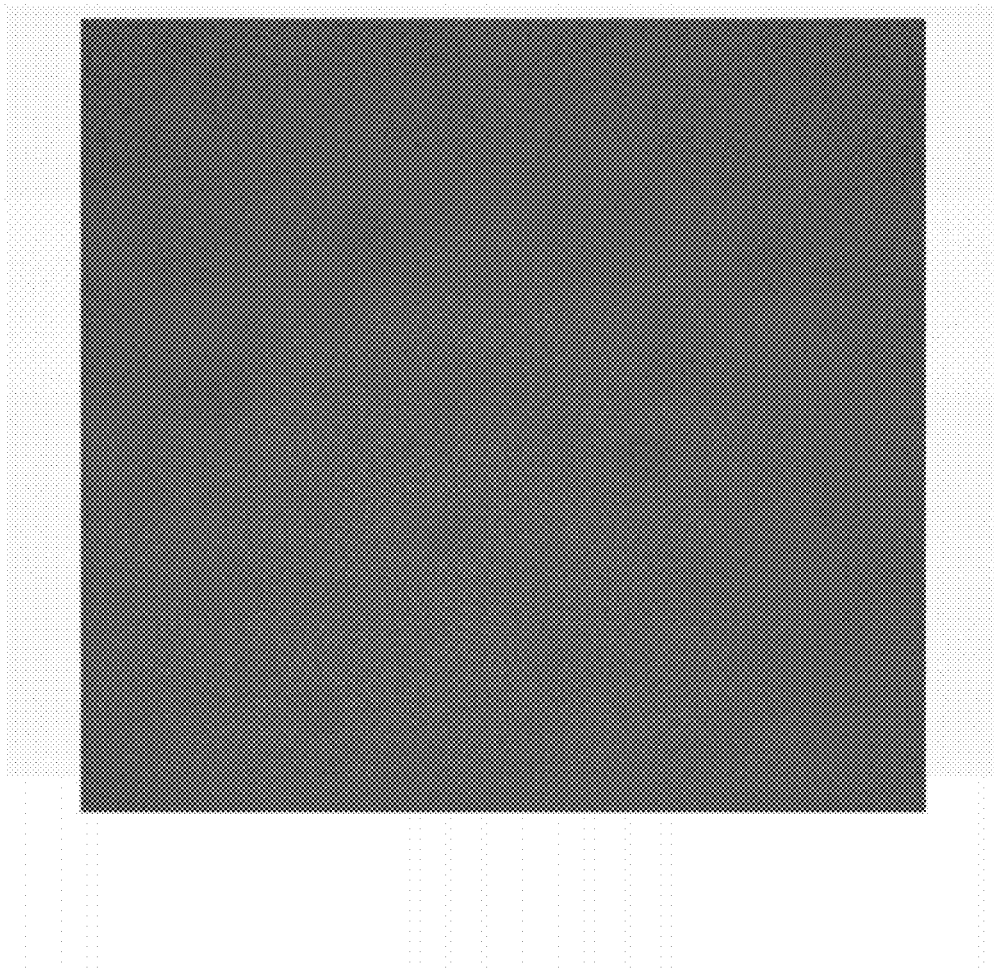
FIG. 8 is a photograph showing the surface of a thin film formed of a compound according to Synthesis Example 1-1 after a heat treatment at 160° C. for 3 hours.
Figure 9:
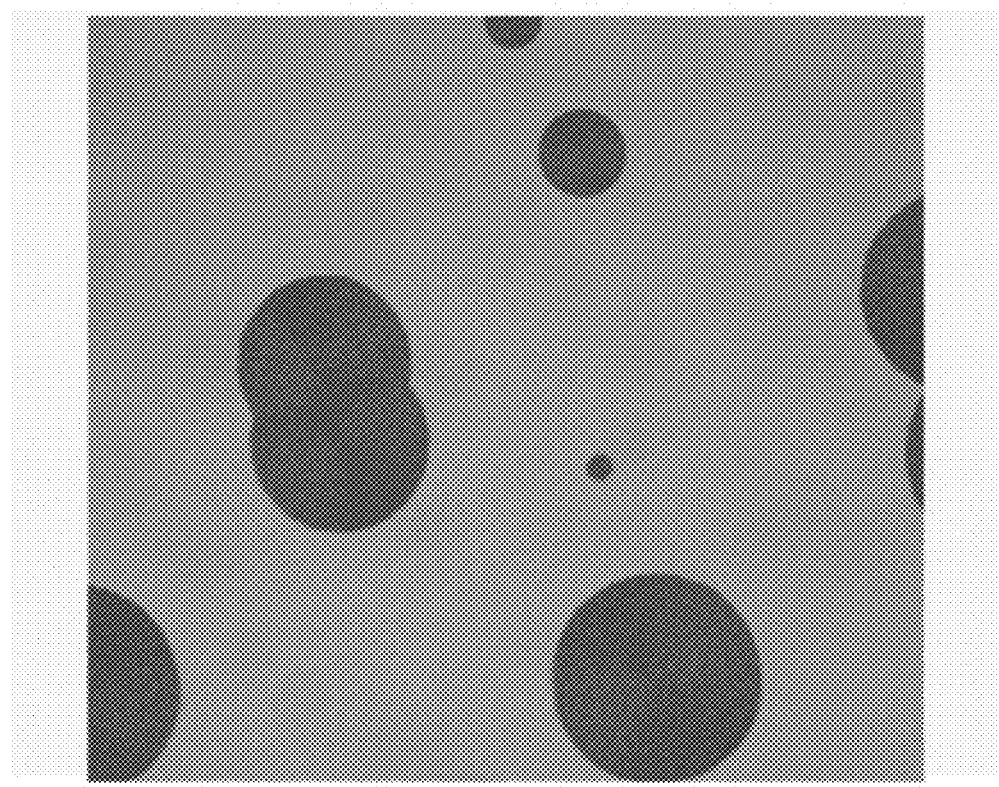
FIG. 9 is a photograph showing the surface of a thin film formed of a compound according to Comparative Synthesis Example 1-1 after allowed to stand at room temperature (24° C.) for 3 hours.
Figure 10:
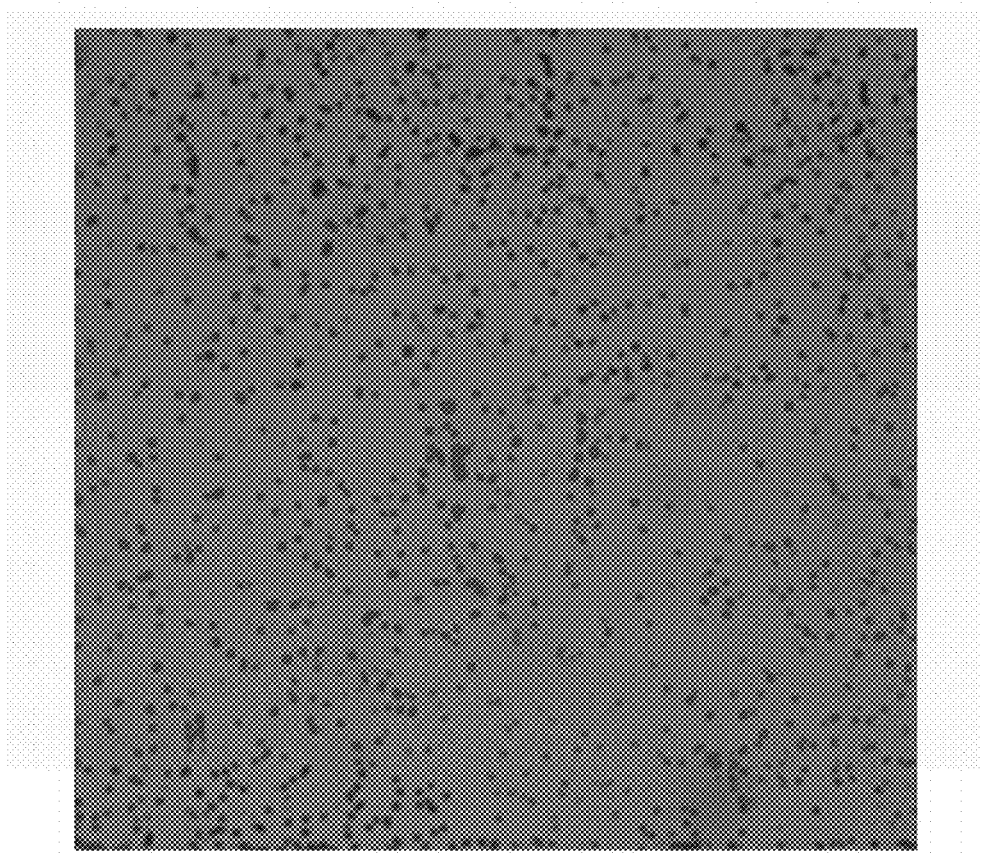
FIG. 10 is a photograph showing the surface of a thin film formed of a compound according to Reference Synthesis Example 1-1 after a heat treatment at 140° C. for 3 hours.

After respectively forming thin films by using the compounds according to Synthesis Examples 1-1 to 8-2, Comparative Synthesis Example 1, and Reference Synthesis Example 1, the thin films are treated at a high temperature and then, examined regarding their morphology changes on the surface. FIGS. 8, 9, and 10 respectively show the surfaces of the thin films formed by respectively depositing the compounds according to Synthesis Example 1-1, Comparative Synthesis Example 1, and Reference Synthesis Example 1. FIG. 8 shows the surface of the thin film coated with the compound according to Synthesis Example 1-1 and heat-treated at 160° C. for 3 hours, FIG. 9 shows the surface of the thin film coated with the compound according to Comparative Synthesis Example 1 and allowed to stand at room temperature (24° C.) for 3 hours, and FIG. 10 shows the surface of the thin film coated with the compound according to Reference Synthesis Example 1 and heat-treated at 140° C. for 3 hours. Referring to FIGS. 8 to 10, the thin film formed of the compound according to Synthesis Example 1-1 shows no morphology change after the heat treatment at 160° C. for 3 hours, but the thin film formed of the compound according to Comparative Synthesis Example 1 shows a surface morphology change after stored at room temperature, and the thin film formed of the compound according to Reference Synthesis Example 1 shows a surface morphology change after the heat treatment at 140° C. for 3 hours.

Example 1-1: Manufacture of Organic Photoelectric Device

An about 150 nm-thick anode is formed by sputtering ITO on a glass substrate, and a 140 nm-thick active layer is formed thereon by codepositing a compound represented by Chemical Structure 1-1 according to Synthesis Example 1-1 (a p-type semiconductor compound) and C60 (a n-type semiconductor compound) in a thickness ratio of 1:1. Subsequently, a 10 nm-thick molybdenum oxide (MoOx, $0<x\leq3$) thin film is formed thereon as a charge auxiliary layer. On the molybdenum oxide thin film, a 7 nm-thick cathode is formed by sputtering ITO, manufacturing an organic photoelectric device.

Examples 1-2 to 8-2: Manufacture of Organic Photoelectric Devices

Organic photoelectric devices according to Examples 1-2 to 8-2 are manufactured according to the same method as Example 1 except for respectively using the compounds according to Synthesis Examples 1-2 to 8-2 instead of the compound according to Synthesis Example 1-1.

Comparative Example 1: Manufacture of Organic Photoelectric Device

An organic photoelectric device according to Comparative Example 1 is manufactured according to the same method as Example 1-1 except for using the compound according to Comparative Synthesis Example 1 instead of the compound according to Synthesis Example 1-1.

Reference Example 1: Manufacture of Organic Photoelectric Device

An organic photoelectric device according to Reference Example 1 is manufactured according to the same method as Example 1-1 except for using the compound according to Reference Synthesis Example 1 instead of the compound according to Synthesis Example 1-1.

External Quantum Efficiency (EQE) of Organic Photoelectric Device

The organic photoelectric devices according to Examples 1-1 to 8-2, Comparative Example 1, and Reference Example 1 are evaluated regarding a maximum absorption wavelength, a full width at half maximum (FWHM), and external quantum efficiency (EQE) depending on a voltage, and external quantum efficiency after allowed to stand at a high temperature.

The external quantum efficiency (EQE) is measured by using an IPCE measurement system (McScience Inc., Korea). The EQE is measured at a wavelength ranging from about 350 to about 750 nm by calibrating IPCE measurement system with the Si photodiode (Hamamatsu Photonics K.K., Japan) and respectively mounting the organic photoelectric devices according to Examples 1-1 to 8-2, Comparative Example 1, and Reference Example 1. The external quantum efficiency after allowed to stand at a high temperature is measured at a wavelength ranging from about 350 to about 750 nm by allowing the organic photoelectric devices to stand at 160° C. for 3 hours. The results are shown in Table 2.

Color Reproducibility (ΔE*ab) and Sensitivity (YSNR10) of Image Sensor

The organic photoelectric devices according to Examples 1-1 to 8-2, Comparative Example 1, and Reference Example 1 are respectively disposed to manufacture image sensors to have the structure of an organic photoelectric device 100 of an image sensor 300 as shown in FIG. 4, YSNR10 and a color difference ΔE*ab from 24 colors of a Macbeth chart are measured by taking a photo of an 18% gray patch of the Macbeth chart under a light source of D-65.

Herein, lens has an F value of 2.8 and transmittance of 80%, and interference-type lens are used for an infrared ray cut filter. A pixel size of the image sensors is 1.4 μm, and a frame rate of the image sensors is 15 fps.

The YSNR10 is obtained in a method described in Juha Alakarhu's "Image Sensors and Image Quality in Mobile Phones" printed in the outline of 2007 International Image Sensor Workshop (Ogunquit Me., USA). The YSNR10 (luminance) is obtained at ΔE*ab=3 by compensating a color with CCM (Color Correction Matrix). After allowing the image sensors to stand at 160° C. for 3 hours, YSNR10 at ΔE*ab=3 is measured. The results are shown in Table 2.

TABLE 2

| Organic photoelectric device | Compounds | $\lambda_{max}$ (nm) | FWHM (nm) | EQE (%) (at −3 V) | EQE (%) (allowed to stand at −3 V, high temperature) | YSN R10 (lux) | YSNR10 (lux, allowed to stand at high temperature) |
|---|---|---|---|---|---|---|---|
| Example 1-1 | Chemical Structure 1-1 | 540 | 113 | 74 | 73 | 77 | 78 |
| Example 1-2 | Chemical Structure 1-2 | 540 | 110 | 70 | 70 | 83 | 83 |
| Example 2-1 | Chemical Structure 2-1 | 545 | 115 | 68 | 67 | 85 | 86 |
| Example 2-2 | Chemical Structure 2-2 | 544 | 120 | 65 | 64 | 86 | 88 |
| Example 2-3 | Chemical Structure 2-3 | 550 | 110 | 67 | 67 | 88 | 88 |
| Example 3-1 | Chemical Structure 3-1 | 540 | 115 | 70 | 70 | 80 | 80 |
| Example 3-2 | Chemical Structure 3-2 | 545 | 111 | 69 | 68 | 80 | 83 |
| Example 3-3 | Chemical Structure 3-3 | 550 | 110 | 65 | 64 | 83 | 85 |

TABLE 2-continued

| Organic photoelectric device | Compounds | $\lambda_{max}$ (nm) | FWHM (nm) | EQE (%) (at −3 V) | EQE (%) (allowed to stand at −3 V, high temperature) | YSN R10 (lux) | YSNR10 (lux, allowed to stand at high temperature) |
|---|---|---|---|---|---|---|---|
| Example 4-1 | Chemical Structure 4-1 | 545 | 111 | 63 | 63 | 95 | 95 |
| Example 4-2 | Chemical Structure 4-2 | 555 | 105 | 64 | 63 | 90 | 94 |
| Example 4-3 | Chemical Structure 4-3 | 545 | 110 | 65 | 63 | 93 | 95 |
| Example 4-4 | Chemical Structure 4-4 | 525 | 112 | 67 | 67 | 81 | 81 |
| Example 5-1 | Chemical Structure 5-1 | 551 | 105 | 64 | 63 | 88 | 90 |
| Example 5-2 | Chemical Structure 5-2 | 540 | 112 | 69 | 68 | 84 | 85 |
| Example 5-3 | Chemical Structure 5-3 | 539 | 105 | 66 | 66 | 80 | 80 |
| Example 8-1 | Chemical Structure 8-1 | 541 | 120 | 74 | 73 | 83 | 84 |
| Example 8-2 | Chemical Structure 8-2 | 530 | 125 | 72 | 72 | 89 | 90 |
| Example 7-2 | Chemical Structure 7-2 | 538 | 110 | 75 | 74 | 75 | 76 |
| Example 7-1 | Chemical Structure 7-1 | 551 | 105 | 70 | 69 | 86 | 89 |
| Example 6-1 | Chemical Structure 6-1 | 535 | 120 | 71 | 70 | 88 | 90 |
| Reference Example 1 | Chemical Structure 9-1 | 535 | 135 | 74 | 55 | 93 | 155 |
| Comparative Example 1 | Chemical Structure 10-1 | 540 | 140 | 65 | 35 | 125 | 190 |

As shown in Table 2, the organic photoelectric devices according to Examples 1-1 to 8-2 show excellent external quantum efficiency compared with the organic photoelectric device according to Comparative Example 1.

In addition, the image sensors respectively including the organic photoelectric devices according to Examples 1-1 to 8-2 have YSNR10 of less than or equal to 100 at ΔE*ab=3 color-compensated with CCM (Color Correction Matrix) and thus may accomplish high sensitivity at high image quality pixels of 1.4 μm.

In addition, the image sensors show no deterioration even after the heat treatment at 160° C. for 3 hours and no EQE and YSNR10 changes. The reason is that morphology is not largely changed by introducing a cross-linking structure into the compounds even after the heat treatment at 160° C. to suppress a movement of molecules.

On the contrary, the organic photoelectric device of Comparative Example 1 shows sufficient EQE of 35% but increased YSNR10 due to a wide full width at half maximum (FWHM) when colors are compensated into ΔE*ab=3 and much deteriorated EQE after the heat treatment at 160° C. for 3 hours and thus may not be applied to an image sensor. Since the compound of Comparative Synthesis Example 1 has no cross-linking structure, heat resistance of the thin film is deteriorated, and the thin film has a morphology change due to the heat treatment at 160° C.

While some example embodiments have been described, one of ordinary skill in the art would understand that variations in form and detail may be made without departing from the spirit and scope of inventive concepts; thus, inventive concepts are not limited to the disclosed embodiments, but, on the contrary, are intended to cover various modifications and equivalent arrangements included within the spirit and scope of the appended claims.

What is claimed is:
1. A compound comprising:
a structure represented by Chemical Formula 1:

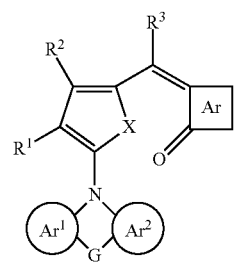

[Chemical Formula 1]

wherein, in Chemical Formula 1,
Ar is one of a substituted or unsubstituted 5-membered aromatic ring, a substituted or unsubstituted 6-membered aromatic ring, or a combination thereof in a condensed ring,
X is one of Se, Te, O, S(=O), S(=O)$_2$, NR$^a$, and SiR$^b$R$^c$ (wherein each of R$^a$, R$^b$, and R$^c$ are independently one of hydrogen or a substituted or unsubstituted C1 to C10 alkyl group),
each of R$^1$ to R$^3$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof,
each of Ar$^1$ and Ar$^2$ are independently one of a substituted or unsubstituted C6 to C30 arylene group, a substituted or unsubstituted C3 to C30 heteroarylene group, a substituted or unsubstituted C6 to C30 arene group, or a substituted or unsubstituted C3 to C30 heteroarene group, and G is one of a direct bond, —(CR$^d$R$^e$)$_n$—, —O—, —S—, —Se—, —N=, —NR$^f$—, —SiR$^g$R$^h$—, —GeR$^i$R$^j$—, or —(C(R$^m$)=C(R$^n$))— (wherein each of R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, or a substituted or unsubstituted C6 to C10 aryl group, and R$^m$ and R$^n$ are linked to each other to provide a fused ring or R$^m$ and R$^n$ are not linked together to provide a fused ring, and n is an integer of 1, or 2).

2. The compound of claim 1, wherein in Chemical Formula 1, at least one of Ar$^1$ and Ar$^2$ include a heteroatom at 1 position, and the heteroatom is one of nitrogen (N), sulfur (S), or selenium (Se).

3. The compound of claim 1, wherein the structure is represented by at least one of Chemical Formula 2-1, Chemical Formula 2-2, Chemical Formula 2-3, Chemical Formula 2-4, or Chemical Formula 2-5:

[Chemical Formula 2-1]

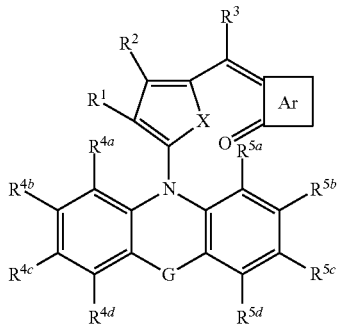

[Chemical Formula 2-2]

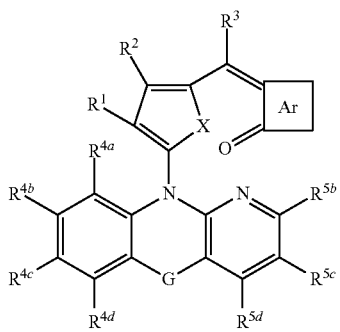

[Chemical Formula 2-3]

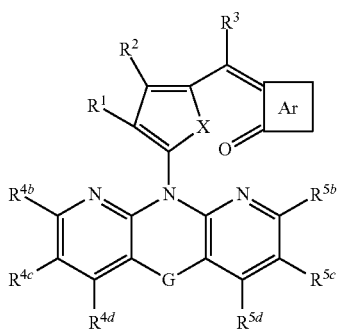

[Chemical Formula 2-4]

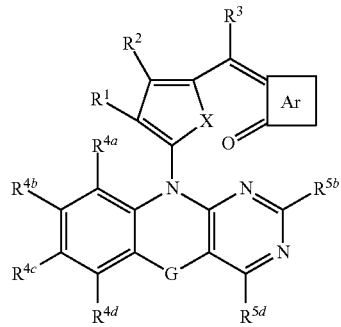

[Chemical Formula 2-5]

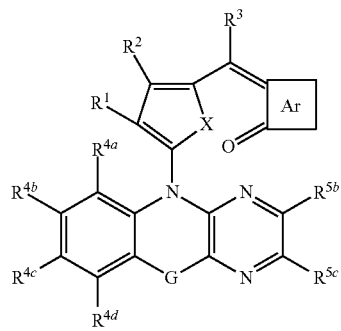

wherein, in Chemical Formula 2-1 to Chemical Formula 2-5,

R$^{4a}$ to R$^{4d}$ and R$^{5a}$ to R$^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{4a}$ to R$^{4d}$ are linked with each other to provide a 5-membered aromatic ring or a 6-membered aromatic ring, or two adjacent groups of R$^{4a}$ to R$^{4d}$ are not linked with each other to provide a 5-membered aromatic ring or a 6-membered aromatic ring, and two adjacent groups of R$^{5a}$ to R$^{5d}$ are linked with each other to provide a 5-membered aromatic ring or a 6-membered aromatic ring or two adjacent groups of R$^{5a}$ to R$^{5d}$ are not linked with each other to provide a 5-membered aromatic ring or a 6-membered aromatic ring.

4. The compound of claim 3, wherein the structure is represented by Chemical Formula 2-2.

5. The compound of claim 3, wherein the structure is represented by Chemical Formula 2-3.

6. The compound of claim 3, wherein the structure is represented by at least one of Chemical Formula 2-4 or Chemical Formula 2-5.

7. The compound of claim 1, wherein in Chemical Formula 1, a ring group represented by Ar and bound to a methine group is represented by Chemical Formula 3:

[Chemical Formula 3]

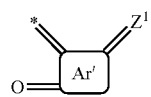

wherein, in Chemical Formula 3,
Ar' is one of a substituted or unsubstituted 5-membered aromatic ring, a substituted or unsubstituted 6-membered aromatic ring, or a combination thereof in a condensed ring, and
$Z^1$ is one of O or $CR^bR^c$, wherein each of $R^b$ and $R^c$ are independently one of hydrogen, a substituted or unsubstituted C1 to C10 alkyl group, a cyano group, or a cyano-containing group, provided that at least one of $R^b$ and $R^c$ is a cyano group or a cyano-containing group.

8. The compound of claim 1, wherein in Chemical Formula 1, a ring group represented by Ar and bound to a methine group is represented by one of Chemical Formula 4-1, Chemical Formula 4-2, Chemical Formula 4-3, or Chemical Formula 4-4:

[Chemical Formula 4-1]

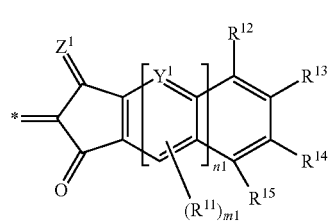

wherein, in Chemical Formula 4-1,
$Z^1$ is O or $CR^bR^c$, wherein each of $R^b$ and $R^c$ are independently one of hydrogen, a substituted or unsubstituted C1 to C10 alkyl group, a cyano group, or a cyano-containing group, provided that at least one of $R^b$ and $R^c$ is a cyano group or a cyano-containing group,
$Y^1$ is one of N and $CR^d$, wherein $R^d$ one of hydrogen and a substituted or unsubstituted C1 to C10 alkyl group,
each of $R^{11}$, $R^{12}$, $R^{13}$, $R^{14}$, and $R^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, or $R^{12}$ and $R^{13}$ are independently linked with each other to provide an aromatic ring or $R^{14}$ and $R^{15}$ are independently linked with each other to provide an aromatic ring,
m1 is 0 or 1,
n1 is 0 or 1, and
indicates a linking position with a methine group,

[Chemical Formula 4-2]

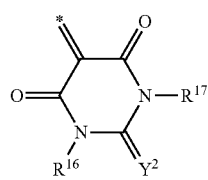

wherein, in Chemical Formula 4-2,
$Y^2$ is one of O, S, Se, Te, and $C(R^e)(CN)$ (wherein $R^e$ is one of hydrogen, a cyano group (—CN), or a C1 to C10 alkyl group),
$R^{16}$ and $R^{17}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
indicates a linking position with a methine group,

[Chemical Formula 4-3]

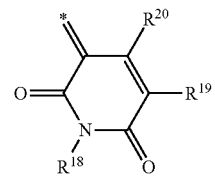

wherein, in Chemical Formula 4-3,
$R^{18}$ to $R^{20}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and
indicates a linking position with a methine group,

[Chemical Formula 4-4]

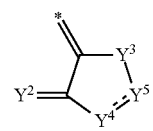

wherein, in Chemical Formula 4-4,
$Y^2$ is one of O, S, Se, Te, and $C(R^e)(CN)$ (wherein $R^e$ is one of hydrogen, a cyano group (—CN), or a C1 to C10 alkyl group),
$Y^3$ is one of O, S, Se, and Te,
$Y^4$ is one of N or $NR^f$,
$Y^5$ is one of $CR^g$, C=O, C=S, C=$(CR^h)(CN)$, and a group represented by Chemical Formula 4-4',
when $Y^2$ is not O, $Y^5$ is C=O and when $Y^5$ is not C=O, $Y^2$ is O,
$R^f$, $R^g$, and $R^h$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and
if $Y^5$ is $CR^g$ or C=$(CR^h)(CN)$, $Y^4$ and $Y^5$ are linked with each other to provide a $Y^4$-$Y^5$-containing fused ring with the ring structure of Chemical Formula 4-4 and bound to the methine group, or $Y^4$ and $Y^5$ are not part of a $Y^4$-$Y^5$-containing fused ring with the ring structure of Chemical Formula 4-4 and bound to the methine group, and
indicates a linking position with a methine group,

[Chemical Formula 4-4']

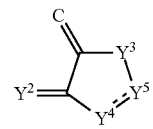

wherein, in Chemical Formula 4-4,
Y², Y³, Y⁴, and Y⁵ are the same as in Chemical Formula 4-4.

9. The compound of claim 1, wherein the structure is represented by one of Chemical 5-1 to 5-4:

[Chemical Formula 5-1]

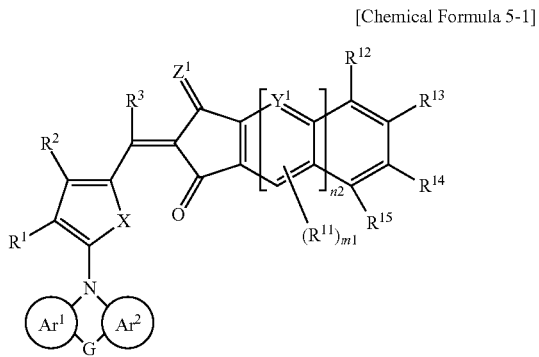

wherein, in Chemical Formula 5-1,
Z¹ is O or CR$^b$R$^c$ (wherein each of R$^b$ and R$^c$ are independently one of hydrogen, a substituted or unsubstituted C1 to C10 alkyl group, a cyano group, or a cyano-containing group, provided that at least one of R$^b$ or R$^c$ is a cyano group or a cyano-containing group),
Y¹ is one of N or CR$^d$, wherein R$^d$ is one of hydrogen and a substituted or unsubstituted C1 to C10 alkyl group,
each of R¹¹, R¹², R¹³, R¹⁴, and R¹⁵ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, or
R¹² and R¹³ are independently linked with each other to provide an aromatic ring, or R¹⁴ and R¹⁵ are independently linked with each other to provide an aromatic ring,
m1 is 0 or 1, and
n2 is 0 or 1,

[Chemical Formula 5-2]

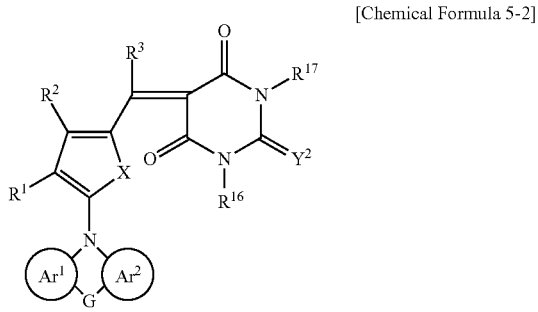

wherein, in Chemical Formula 5-2,
Y² is one of O, S, Se, Te, or C(R$^e$)(CN) (wherein R$^e$ is one of hydrogen, a cyano group (—CN), or a C1 to C10 alkyl group), and
each of R¹⁶ and R¹⁷ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof,

[Chemical Formula 5-3]

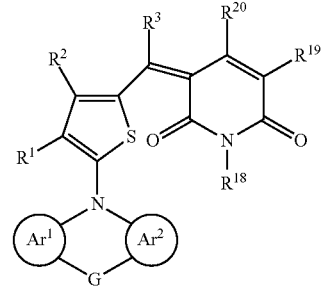

wherein, in Chemical Formula 5-3,
each of R¹⁸, R¹⁹, and R²⁰ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof,

[Chemical Formula 5-4]

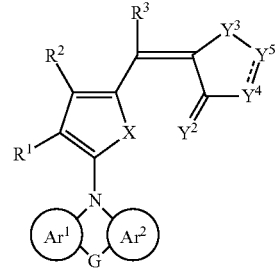

wherein, in Chemical Formula 5-4,
Y² is one of O, S, Se, Te, and C(R$^e$)(CN) (wherein R$^e$ is one of hydrogen, a cyano group (—CN), or a C1 to C10 alkyl group),
Y³ is one of O, S, Se, or Te,
Y⁴ is one of N or NR$^f$,
Y⁵ is one of CR$^g$, C═O, C═S, C═(CR$^h$)(CN), or a group represented by Chemical Formula 4-4',
when Y² is not O, Y⁵ is C═O and when Y⁵ is not C═O, Y² is O,
each of R$^f$, R$^g$, and R$^h$ are independently one of a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and
if Y⁵ is CR$^g$ or C═(CR$^h$)(CN), Y⁴ and Y⁵ are linked with each other to provide a Y⁴-Y⁵-containing fused ring with the ring structure of Chemical Formula 5-4, or Y⁴ and Y⁵ are not part of a Y⁴-Y⁵-containing fused ring with the ring structure of Chemical Formula 5-4,

[Chemical Formula 4-4']

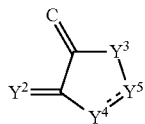

wherein, in Chemical Formula 4-4',
$Y^2$, $Y^3$, $Y^4$, and $Y^5$ are the same as in Chemical Formula 4-4.

10. The compound of claim 1, wherein the compound has a maximum absorption wavelength ($\lambda_{max}$) in a wavelength region of greater than or equal to about 510 nm and less than about 560 nm.

11. The compound of claim 1, wherein the compound has a maximum absorption wavelength ($\lambda_{max}$) in a wavelength region of about 520 nm to about 555 nm.

12. The compound of claim 1, wherein the compound exhibits a light absorption curve having a full width at half maximum (FWHM) of about 50 nm to about 120 nm, in a thin film state.

13. The compound of claim 1, wherein a difference between a melting point of the compound and a deposition temperature at which 10 wt % of an initial weight of the compound is lost may be greater than or equal to about 3° C.

14. A organic photoelectric device, comprising
a first electrode and a second electrode facing each other, and
an active layer between the first electrode and the second electrode,
wherein the active layer includes the compound of claim 1.

15. The organic photoelectric device of claim 14, wherein the active layer has a maximum absorption wavelength ($\lambda_{max}$) in a wavelength region of greater than or equal to about 510 nm and less than about 560 nm.

16. The organic photoelectric device of claim 14, wherein the active layer has a maximum absorption wavelength ($\lambda_{max}$) in a wavelength region of about 520 nm to about 555 nm.

17. The organic photoelectric device of claim 14, wherein the active layer exhibits a light absorption curve having a full width at half maximum (FWHM) of about 50 nm to about 120 nm.

18. An image sensor comprising:
the organic photoelectric device of claim 14.

19. The image sensor of claim 18, further comprising:
a semiconductor substrate integrated with a plurality of first photo-sensing devices for sensing light in a blue wavelength region and a plurality of second photo-sensing devices for sensing light in a red wavelength region, wherein
the organic photoelectric device is on the semiconductor substrate and configured to selectively sense light in a green wavelength region.

20. The image sensor of claim 19, further comprising:
a color filter layer, wherein
the color filter layer includes a blue filter for selectively absorbing light in a blue wavelength region and a red filter for selectively absorbing light in a red wavelength region.

21. The image sensor of claim 19, wherein the plurality of first photo-sensing devices and the plurality of second photo-sensing devices are stacked in a vertical direction in the semiconductor substrate.

22. The image sensor of claim 18, wherein
the image sensor includes a green photoelectric device, a blue photoelectric device for selectively absorbing light in a blue wavelength region, and a red photoelectric device for selectively absorbing light in a red wavelength region that are stacked, and
the organic photoelectric device is the green photoelectric device.

23. An electronic device comprising:
the image sensor of claim 19.

* * * * *